(12) United States Patent
Bojack et al.

(10) Patent No.: US 7,368,437 B1
(45) Date of Patent: May 6, 2008

(54) BICYCLIC HETEROCYCLES, PROCESSES FOR THEIR PREPARATION AND THEIR USE AS HERBICIDES AND PHARMACEUTICAL AGENTS

(75) Inventors: Guido Bojack, Wiesbaden (DE); Stephen Lindell, Kelkheim-Fischbach (DE); Christopher Rosinger, Hofheim (DE); Philip Dudfield, Saffron Walden (GB); Christopher G. Earnshaw, Chesterton (GB)

(73) Assignee: Bayer CropScience AG, Frankfurt am Main (DE)

( * ) Notice: Subject to any disclaimer, the term of this patent is extended or adjusted under 35 U.S.C. 154(b) by 0 days.

(21) Appl. No.: 09/526,348

(22) Filed: Mar. 16, 2000

(30) Foreign Application Priority Data

Mar. 20, 1999 (DE) ............................... 199 12 636

(51) Int. Cl.
 A61K 31/70 (2006.01)
 A61K 31/675 (2006.01)
 A61K 31/52 (2006.01)
 C07H 19/06 (2006.01)
 C07H 15/12 (2006.01)
 C07H 17/00 (2006.01)
 C07D 473/00 (2006.01)

(52) U.S. Cl. .................... 514/45; 514/81; 514/261; 536/26.7; 536/26.71; 536/27.13; 544/264

(58) Field of Classification Search ............ 536/26.7, 536/26.71, 27.13; 544/264; 514/45, 81, 514/261
See application file for complete search history.

(56) References Cited

U.S. PATENT DOCUMENTS 5,045,557 A * 9/1991 Buss et al. ................ 514/398
5,096,915 A * 3/1992 Parsons et al. ............ 514/398
5,786,165 A * 7/1998 Dancer et al. .............. 435/18

FOREIGN PATENT DOCUMENTS

WO    WO 94/18200    9/1994

OTHER PUBLICATIONS

Duffy et al., "The Scope and Mechanism of a Novel Synthesis of 3,4-Fused Isothiazoles," *Journal of the Chemical Society, Chemical Communications*, 1995, (Issue No. 23), 2457-2459 (Dec. 7, 1995).*
Frieden et al., "Adenosine Deaminase and Adenylate Deaminase: Comparative Kinetic Studies with Transition State and Ground State Analogue Inhibitors," *Biochemistry*, 19(23), 5303-5309 (Nov. 11, 1980).*
Gewald et al. (I), "New Synthesis of 4-aminoisothiazoles," *Zeitschrift für Chemie*, 15(1), 18-19 (1975); *Chemical Abstracts*. 82(21), p. 616, Abstract No. 139991k (May 26, 1975); only Abstract supplied.*
Gewald et al. (II), "Synthesis and Reactions of 4-aminoisothiazoles," *Justus Liebigs Annalen der Chemie*, 1979(10), 1534-1546 (Oct. 1979); *Chemical Abstracts*, 92(9), p. 667, Abstract No. 76382w (Mar. 3, 1980).*
Kobe et al., "Use of Distance Geometry Approach for the in vitro Antiviral Activity Evaluation of N-Bridgehead C-Nucleosides," *European Journal of Medicinal Chemistry*, 27(3), 259-266 (1992).*
Kurasawa et al., "Synthesis and Conversions of 3-(4-Amino-5-methyl-4H-1,2,4-triazol-3-ylmethylene-2-oxo-1,2,3,4-tetrahydroquinozaline," *Journal of Heterocyclic Chemistry*, 22(6). 1715-1718 (Nov.-Dec. 1985).*
Poreba et al., "Synthesis and Preliminary Pharmacological Assessment of the Derivatives of Isoxazolo[4,3-d]pyrimidine. II," *Acta Polonica Pharm.*, 51(4-5), 355-358 (1994); *Chemical Abstracts*, 123(11), p. 1264, Abstract No. 143787f (Sep. 11, 1995); only Abstract supplied.*
Poreba et al. (I), "Synthesis and Preliminary Pharmacological Assessment of the Derivatives of Isoxazolo[4,3-d]pyrimidine. II," *Acta Polonica Pharm.- Drug Research*, 51(4-5), 355-358 (1994) @@; *Chemical Abstracts*, 123(11), p. 1264, Abstr. No. 143787f (Sep. 11, 1995).*
Milne et al., "Pyrazolopyrimidine Nucleosides. Part IV. Synthesis and Chemical Reactivity of the C-Nucleoside Selenoformycin B and Derivatives," *Journal Chemical Society, Perkin Tranaactions I*, 1972, pp. 2677-2681.*
Watanabe et al., "The Studies on the Chemical Derivations of Formycin and Formycin B," *The Journal of Antibiotics, Series A*, 19(2), 93-96 (Mar. 1966).*
Long et al., "Pyrazolopyrimidine Nucleosides. Part II. 7-Substituted 3-β-D-Ribofuranosyl[3,4-d]pyrimidines Related to and Derived from the Nucleoside Antibiotics Formycin and Formycin B," *Journal of the Chemical Society* (C), 1971, pp. 2443-2446.*
Ramasamy et al., "Synthesis and Antitumor Activity of Certain 3-β-D-Ribofuranosyl-1,2,4-triazolo[3,4-f]-1,2,4-triazines Related to Formycin Prepared via ring Closure of a 1,2,4-Triazine Precursor," *Journal of Medicinal Chemistry*, 29(11), 2231-2235 (1986).*
Fox et al., "Thiation of Nucleosides. I. Synthesis of 2-Amino-6-mercapto-9-β-D-ribofuranosylpurine ("Thioguanosine") and Related Purine Nucleosides," *Journal of the Amer. Chem. Soc.*, 80(4), 1669-1675 (Apr. 5, 1958).*
Woods et al. "Solvolytic Reactivities of Some 7-Chloronorbornane Derivatives," *Journal of the Amer. Chem. Soc.*, 78, 5653-5657 (Nov. 5, 1956).*
Kawana et al., "Synthesis of 2-Fluoro-9-β-D-Ribofuranosylpurine (2-Fluoronebularine)," *Journal of Medicinal Chemistry*, 15(2), 214-215 (1972).*
Nair et al., "Reductive Deamination of Aminopurine Nucleosides," *Synthesis*, 1984, pp. 401-404 (May 1984).*

(Continued)

*Primary Examiner*—S. Anna Jiang
*Assistant Examiner*—L. E. Crane
(74) *Attorney, Agent, or Firm*—Frommer Lawrence & Haug LLP

(57) ABSTRACT

Methods and compounds for inhibiting the enzymes adenosine monophosphate deaminase or adenosine deaminase are provided. Such methods and compounds are useful in agriculture, horticulture and/or pharmacology as, for example, active compounds for crop protection or pharmaceuticals for humans or animals.

19 Claims, No Drawings

OTHER PUBLICATIONS

Buck et al., "Conversion of Guanosine into Acyclovir and its 6-Deoxy Derivative," *Tetrahedron*, 50(30), 9195-9206 (1994).*

L'abbé et al., "5-Chloropyrazole-4-carboxaldehydes as Synthons for Intramolecular 1,3-Dipolar Cycloadditions," *Journal of the Chem. Soc., Perkin Transactions I*, 1994, pp. 2553-2558.*

Buchanan et al., "C-Nucleoside Studies. Part 19. The Synthesis of the β-D-Xylofuranosyl Analogues for Formycin," *Journal of the Chem. Soc., Perkin Transactions I*, 1986, pp. 1267-1271.*

Lewis et al., "Pyrazolopyrimidine Nucleosides. 13. Synthesis of the Novel C-Nucleoside 5-Amino-3-(β-D-ribofuranosyl)pyrazolo[3,4-d]pyrimidin-7-one, a Guanosine Analogue Related to the Nucleoside Antibiotic Formycin B," *Journal of the Amer. Chem. Soc.*, 104(4), 1073-1077 (1982).*

Hennen et al., "Synthesis of 4-Substituted 5-Amino-2-(β-D-ribofuranosyl)thiazoles and 4-Substituted 5-Amino-2(β-D-ribofuranosyl)selenazoles and Their Respective Conversion into 2-(β-D-ribofuranosyl)thiazolo[5,4-d]pyrimidines and 2-(β-D-ribofuranosyl)selenazolo[5,4-d]pyrimidines. A New Synthesis of Tiazofurin and Selenazofurin," *Journal of Organic Chemistry*, 50, 1741-1746 (1985).*

Ivanovics et al., "The Synthesis of 2-Substituted Derivatives of 5-Amino-1-β-D-ribofuranosylimidazole-4-carboxamide. Ring Opening Reactions of 2-Azapurine Nucleosides," *Journal of Organic Chemistry*, 39(25), 3651-3654 (1974).*

Rayner et al., "Rechereche sur la Nucleosides de Synthese: II Obtention d'Anomeres-α en Series Purinique (French)," *Heterocyclic C hemistry*, 10, 417-418 (Jun. 1973).*

Ellames et al., "The Synthesis of Acycloformycins and 5-Amino-3-(2-hydroxyethoxy)-methylpyrazolo[4,3-d]pyrimidin-7(6H)-one, an Analogue of the Antiviral Acycloguanosine," *Journal of the Chem. Soc., Perkin Transactions I*, 1985, pp. 2087-2091.*

Wierzchowski et al., "Analogues of Formycins A and B: Synthesis and Some Properties of Methyl Derivatives of 7-amino and 7-Keto Pyrazolo[4,3-d]pyrimidines," *Acta Biochimica Polonica*, 27(1), 35-56 (1980).*

Kalvoda, "The Synthesis of Pyrazoles: A Simple Preparative Synthesis of C-Nucleosidic Antibiotics Formycin and Formycin B," *Coll. Czech. Chem. Communications*, 43, 1431-1437 (1978).*

Sims et al., "Elevated Adenosine Monophosphate Deaminase Activity in Alzheimer's Disease Brain," *Neurobiology of Aging*, 19(5), 385-391 (1998).*

Poreba et al. (II), "Synthersis and Pharmacological Screening of Derivatives of Isoxazolo[4,3-d]pyrimidine. I," *Il Farmaco*, 49(7,8), 529-532 (1994).*

El-Maaty et al. (I), "Synthesis of Certain Isothiazolo[4,3-d]pyrimidine Derivatives of Pharmaceutical Interest," *Bull. Fac. Pharm. Cairo Univ.*, 29(2), 41-47 (1991).*

El-Maaty et al. (II), "Synthesis of Certain Isothiazolo[4,3-d]pyrimidine-5,7-(4H,6H)-diones of Pharmaceutical Interest," *Egypt. J. Pharm. Sci.*, 34(4-6), 421-430 (1993).*

Bhattacharya et al., "Synthesis of Certain N- and C-Alkyl Purine Analogs," *Journal of Heterocyclic Chemistry*, 30, 1341-1349 (Oct.-Nov. 1993).*

Rao et al., "Synthesis of Certain Acyclic Nucleoside Analogs of 1,2,4-Triazolo[3,4-f][1,2,4]triazine and Pyrimido[5,4-d]pyrimidine," *Nucleosides & Nucleotides*, 14(7), 1601-1612 (1995).*

Shaban, "The Chemistry of C-Nucleosides and Their Analogs II: C-Nucleosides of Condensed Heterocyclic Bases," *Advances in Heterocyclic Chemistry*, 70, 163-309 (1996); only pp. 163-177 supplied.*

Erion et al., "Discovery of AMP Mimetics that Exhibit High Inhibitory Potency and Specificity for AMP Deaminase," *Journal of the Amer. Chem. Soc.*, 121(2), 308-319 (1999); WEB published on Dec. 31, 1998.*

Dancer et al. (II), "Adenosine-5'-Phosphate Deaminase," *Plant Physiology*, 114, 119-129 (1997).*

Dudfield et al, J. Chem. Soc. Perkin Trans. I (20), (1999), pp. 2937-2942, also referred to as XP 000916905.

Dudfield et al, J. Chem. Soc. Perkin Trans. I (20), (1999), pp. 2929-2936, also referred to as XP 000916904.

Lindell et al, Bioorganic & Medicinal Chemistry Letters, vol. 9, No. 14, (1999), pp. 1985-1990.

Avila et al, Comp. Biochem Physiol., C: Comp. Pharmacol. Toxicol., vol. 83C, No. 2, (1986), pp. 285-289;also reffered as XP 000916769.

J. Antibiot., Ser. A, vol. 20, No. 5, (1967), pp. 297-298; also referred to as XP 000916768, Takeuchi et al.

Milne, G. et al, "Pyrazolopyrimidine Nucleosides. Part IV. Synthesis and Chemical Reactivity of the C-Nucleoside Selenoformycin Band Derivatives," J. Chem. Soc. Perkins Trans I, (1972), pp. 2677-2681.

Watanabe, S. et al, " The Studies on the Chemical Derivations of Formycin and Formycin B," J. Antibiotics Ser. A., vol. 19, No. 2, (1966), pp. 93-96.

Long, R. et al, Pyrazolopyrimidine Nucleosides. Part II., J. Chem. Soc. (C), (1971), pp. 2443-2446.

Ramasamy, K. et al, Synthesis and Antitumor Activity of Certain 3-b-D Ribofuranosyl- 1,2,3- triazolo [3,4-f]- 1,2,4-triazines Related to Formycin Prepared via Ring Closure of a 1,2,4-Triazine Precursor, J. Med. Chem., vol. 29, (1986), pp. 2231-2235.

Fox, J. et al, Thiation of Nucleosides, J. Am. Chem. Soc., vol. 80, (1958), pp. 1669-1675.

Poreba, K. et al, Synthesis and Preliminary Pharmacological Assessment of Derivatives of Isoxazolo [4,3-d] Pyrimidine. II, Acta. Pol. Pharm. Drug Res., vol. 51, No. 4-5, (1994), pp. 355-358.

Woods, W. et al, Solvolytic Reactivities of Some 7-Chloromorbornane Derivatives, J. Am Chem. Soc., vol. 78, (1956), pp. 5653-5657.

Kiefer, E., A Rapid, Convenient Preparative Procedure for Phenethylamines, J. Med. Chem. , vol. 15, No. 2, (1972), pp. 214-216.

Nair, V. and Chamberlain, S, Reductive Deamination of Aminopurine Nucleosides, Synthesis, (1984), pp. 401-404.

Buck, I. et al, Conversion of Guanosine into Acyclovir and its 6-Deoxy Derivative, Tetrahedron, vol. 50, No. 30, (1994), pp. 9195-9206.

L'abbe, G. et al, 5-Chloropyrazole-4-carbaldehydes as Synthons for Intramolecular 1,3-Dipolar Cycloadditions, J. Chem, Soc. Perkin Trans. I, (1994), pp. 2553-2558.

Buchanan, J.G. et al, C-Nucleoside Studies. Part 19., J. Chem. Soc. Perkins Trans. I (1986), pp. 1267-1271.

Lewis, A.F. and Townsend, L.B., Pyrazolopyrimidine Nucleosides. 13., J. Am. Soc., vol. 104, (1982), pp. 1071-1107.

Hennen, W.J. et al, Synthesis of 4-Substituted 5-Amino-2-(b-D-ribofuranosyl) thiazoles and 4-Substituted 5-Amino-2-(beta-D-ribofuranosyl) selenazoles and their Respective Conversion into 2-(beta-D-Ribofuranosyl) thaizolo [5,4-d] pyrimidines and 2-(beta-D-Ribofuranosyl) selenazolo [5,4-d] pyrimidines. A New Systhesis of Tiazofurin and Selenazofurin, J. Org. Chem., vol. 50, (1985), pp. 1741-1746.

Ivanovics, G.A., et al, Synthesis of 2-Substituted Derivatives of 5-Amino-1-beta-D-ribofuranosyl-imidazole-4carboxamide. Ring Opening Reactions of 2-Azapurine Nucleosides, J. Org. Chem., vol. 39, No. 25, (1974), pp. 3651-3654.

Rayner, B. et al, Recherche sur les Nucleosides de Syntheses: II Obtention d'Anomeres a en Serie Purinique, J. Heterocyclic Chem., vol. 10, (1973), pp. 417-418.

Ellames, G.J. et al, The Suntheses of Acycloformycins and 5-Amino-3-(2-hydroxyethoxy)- methylpyrazolo [4,3-d] pyrimidin-7(6H)-one, an Analogue of the Antiviral Acycloguanosine, J. Chem. Soc. Perkin Trans I, (1985), pp. 2087-2091.

Wierzchowski, J. et al, Analogues of Formycins A and B: Synthesis and Some Properties of Methyl Derivatives of 7-Amino and 7-Keto Pyrazolo (4,3-d) Pyrimidines, Acta Biochimica Polonica, vol. 27, No. 1, (1980), pp. 35-36.

Kalvoda, L., The Suntheses of Pyrazoles. A Simple Preparative Synthesis of C-Nucleosidic Antibiotics Formycin B, Coll. Czech. Chem. Commun., vol. 43, (1978), pp. 1431-1437.

Sims, B. et al, Elevated Adenosine Monophosphate Deaminase Activity in Alzheimer's Disease Brain, Neurobiology of Aging, vol. 19, No. 5 (1998), 385-391.

Poreba, K. et al, Synthesis and Pharmacological Screening of Derivatives of Isoxazolo [4,3-d]Pyridimidine. I, II Farmaco, vol. 49, No. 7+8, (1994), 529-532.

El-Maaty, S. et al, Synthesis of Certain Isothiazolo [4,3-d] Pyrimidine Derivatives of Pharmaceutical Interest, Bull. Fac. Pharm. Cairo Univ., vol. 29, No. 2 (1991), pp. 41-47.

El-Maaty, S. et al, Suynthesis of Certain Isothiazolo [4,3-d] Pyrimidine—5,7- (4H, 6H)—Diones of Pharmaceutical Interest, Egypt. J. Pharm. Sci., vol. 34; No. 4-6, (1993), pp. 421-430.

Bhattacharya, B. et al, Synthesis of Certain N- and C-Alkyl Purine Analogs, J. Heterocyclic Chem. , vol. 30, (1993), pp. 1341-1349.

Rao, T., et al, "Synthesis of Certain Acyclic Nucleoside Analogs of 1,2,4-Triazolo[3,4-f][1,2,4]Triazine and Pyrimido[5,4-d]Pyrimidine," 1Nucleosides and Nucleotides, vol. 14, No. 7, (1995), pp. 1601-1612.

Shaban, M., The Chemistry of C-Nucleosides and their Analogs II: C-Nucleosides of Condensed Heterocyclic Bases, Advances in Heterocyclic Chem., vol. 70, (1998), pp. 163-177.

Erion, M. et al, Discovery of AMP Mimetics that Exhibit High Inhibitory Potency and Specificty for AMP Deaminase, J. Am. Chem. Soc., vol. 121, (1999), pp. 308-319.

Dancer, J. et al, Adenosine-5' Phosphate Deaminase, Plant Physiol, vol. 114, (1997), pp. 119-129.

J. Chem. Soc. Perkins Trans 1, (1972), pp. 2677-2681.
J. Antibiotics Ser. A., vol. 19, No. 2, (1966). pp. 93-96.
J. Chem. Soc. (C), (1971), pp. 2443-2446.
J. Med. Chem., vol. 29, (1986), pp. 2231-2235.
J. Am. Chem. Soc. vol. 80. (1958), pp. 1669-1675.
Acta. Pol. Pharm. Drug Res., vol. 51, No. 4-5, (1994), pp. 355-358.
J. Am. Chem. Soc., vol. 78, (1956), pp. 5653-5657.
J. Med. Chem., vol. 15, No. 2, (1972), pp. 214-216.
Synthesis. (1984), pp. 401-404.
Tetrahedron, vol. 50, No. 30, (1994), pp. 9195-9206.
J. Chem. Soc. Perkin Trans. I. (1994), pp. 2553-2558.
J. Chem. Soc. Perkins Trans. I (1986), pp. 1267-1271.
J. Am. Soc., vol. 104, (1982), pp. 1071-1077.
J. Org. Chem., vol. 50, (1985), pp. 1741-1746.
J. Org. Chem., vol. 39, No. 25, (1974), pp. 3651-3654.
J. Heterocyclic Chem., vol. 10, (1973), pp. 417-418.
J. Chem. Soc. Perkin Trans I. (1985), pp. 2087-2091.
Acta Biochimica Polonica, vol. 27, No. 1, (1980), pp. 35-36.
Coll. Czech. Chem. Commun., vol. 43, (1978), pp. 1431-1437.
Neurobiology of Aging. vol. 19, No. 5 (1998), 385-391.
Il Farmaco, vol. 49, No. 7-8, (1994), 529-532.
Bull. Fac. Pharm. Cairo Univ., vol. 29., No. 2 (1991), pp. 41-47.
Egypt J. Pharm. Sci. vol. 34, No. 4-6, (1993), pp. 421-430.
J Heterocyclic Chem., vol. 30, (1993), pp. 1341-1349.
Nucleosides and Nucleotides, vol. 14, No. 7, (1995), pp. 1601-1612.
Advances in Heterocyclic Chem., vol. 70, (1998), pp. 163-177.
J. Am. Chem. Soc., vol. 121, (1999), pp. 308-319.
Plant Physiol, vol. 114 (1997), pp. 119-129.

* cited by examiner

BICYCLIC HETEROCYCLES, PROCESSES FOR THEIR PREPARATION AND THEIR USE AS HERBICIDES AND PHARMACEUTICAL AGENTS

This application claims foreign priority under 35 U.S.C. §111 with DE 199 12 636, filed on 20 Mar. 1999.

The invention relates to active compounds for use in agriculture, horticulture and/or pharmacology, for example as active compounds for crop protection or as pharmaceuticals for use on humans or animals. The invention preferably relates to chemically active compounds for crop protection, such as herbicides or plant growth regulators, for example herbicides for the selective control of harmful plants in crops of useful plants or herbicides for the non-selective use for controlling undesirable vegetation. Moreover, the invention preferably also relates to pharmaceuticals for treating diseases which can be treated by influencing or inhibiting the enzyme adenosine monophosphate deaminase.

Adenosine monophosphate deaminase (AMPDA) is an enzyme which catalyzes the deamination of adenosine monophosphate (AMP) to inosine monophosphate (IMP) in cells. The importance of this enzyme, in particular for the metabolism of higher biological organisms, is the basis upon which, by modulating the enzyme activity, for example using inhibitors, a biological effect can be produced both in plants and in humans and animals. However, differences in the structure of the AMPDA enzymes and in the biological environment of plants and animals can, in principle, lead to different enzyme activities on the one hand and to different effects when using the same enzyme inhibitors in different organisms on the other hand.

Some inhibitors of the enzyme AMPDA are already known. WO-A-96/1326 (U.S. Pat. No. 5,786,165) describes inhibitors of the enzyme AMPDA in plants. The inhibitors can be used as herbicides.

WO-A-94118200 (U.S. Pat. No. 5,731,432) describes inhibitors of AMPDA and their multifarious pharmaceutical applications, for example as agents for diseases which are caused by, inter alia, oxygen deficits in the tissue, for example cardiovascular disorders, inflammations, arthritis.

However, some of the known active compounds of the AMPDA inhibitor type have disadvantages, be it that they have insufficient activity, insufficient stability or that they are difficult to prepare, that they have undesirable side-effects or poor degradability in biological systems. Accordingly, there was a demand for alternative active compounds which can be used as AMPDA inhibitors. These compounds are preferably suitable for use as herbicides or plant growth regulators.

The present invention provides the use of compounds of the formula (I), their tautomers, their salts and their water addition products,

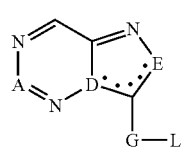

(I)

where in formula (I)

A is a nitrogen atom or a group of the formula C—R, where R is as defined further below, D is a carbon atom or a nitrogen atom, E a) in the case that D is a nitrogen atom, is a nitrogen atom or a group of the formula C—$R^\circ$, where $R^\circ$ is as defined further below, or b) in the case that D is a carbon atom, is a group of the formula N—$R^\circ$, —O—, —S—, —SO— or —$SO_2$—, the line of dots (•••••) from D via an adjacent ring carbon atom to E is a double bond between the ring carbon atom and E if D is a nitrogen atom (case a), or is a double bond between the ring carbon atom and D if D is a carbon atom (case b), R, $R^\circ$ independently of one another are each a hydrogen atom, amino, hydroxyl, mercapto, cyano, halogen, azido, nitro, $SF_5$, unsubstituted or substituted aminosulfonyl, preferably aminosulfonyl or mono- or di($C_1$-$C_4$)alkylaminosulfonyl, or acyl, acylamino, preferably in that case monoacylamino, diacylamino or N-acyl-N—($C_1$-$C_4$)alkylamino, or acyloxy, acylthio, mono- or di($C_1$-$C_4$)alkylamino, mono- or di($C_3$-$C_9$)cycloalkylamino, ($C_1$-$C_4$)alkylthio, ($C_2$-$C_4$)alkenylthio, ($C_2$-$C_4$)alkynylthio, ($C_3$-$C_9$)cycloalkylthio, ($C_5$-$C_9$)cycloalkenylthio, ($C_1$-$C_4$)alkylsulfinyl, ($C_1$-$C_4$)alkylsulfonyl, ($C_1$-$C_4$)alkoxy, ($C_2$-$C_4$)alkenyloxy, ($C_2$-$C_4$)alkynyloxy, ($C_3$-$C_9$)cycloalkoxy, ($C_5$-$C_9$)cycloalkenyloxy, ($C_1$-$C_4$)alkyl, ($C_2$-$C_4$)alkenyl, ($C_2$-$C_4$)alkynyl, ($C_3$-$C_9$)cycloalkyl, ($C_5$-$C_9$)cycloalkenyl, ($C_1$-$C_4$)alkylaminosulfonyl or di[($C_1$-$C_4$)alkyl]aminosulfonyl, where each of the 23 last-mentioned radicals is unsubstituted or substituted in the hydrocarbon moiety by one or more radicals selected from the group consisting of halogen, hydroxyl, amino, nitro, formyl, carboxyl, cyano, thiocyanato, ($C_1$-$C_4$)alkoxy, ($C_3$-$C_9$)cycloalkoxy, ($C_1$-$C_4$)haloalkoxy, ($C_1$-$C_4$)alkylthio, ($C_1$-$C_4$)haloalkylthio, mono($C_1$-$C_4$)alkylamino, di($C_1$-$C_4$)alkylamino, ($C_3$-$C_9$)cycloalkyl, ($C_3$-$C_9$)cycloalkylamino, [($C_1$-$C_4$)alkyl]carbonyl, [($C_1$-$C_4$)alkoxy]carbonyl, aminocarbonyl, mono($C_1$-$C_4$)alkylaminocarbonyl and di($C_1$-$C_4$)alkylaminocarbonyl, G is a divalent straight-chain saturated or unsaturated hydrocarbon bridge having 1 to 24 carbon atoms, preferably 1 to 12 carbon atoms, in particular 1 to 8 carbon atoms, very particularly preferably 4 to 6 carbon atoms, in the chain, in which one or more chain members, in each case independently of one another, can be replaced by O, S, NH, ($C_1$-$C_4$)alkyl-N or acyl-N, preferably by O, S, NH or ($C_1$-$C_4$)alkyl-N, or, in the unsaturated case, one or more CH groups can in each case be replaced by a nitrogen atom, where the bridge in question is unsubstituted or (a) substituted by one or more identical or different radicals selected from the group consisting of halogen, nitro, radicals of the formula $R^1$ which are different from hydrogen, radicals of the formula $R^2R^3C=$ and radicals of the formula L*, where $R^1$, $R^2$, $R^3$ and L* are as defined further below, (b) carries two or four substituents, of which in each case two together with the linking bridge moiety form a carbocyclic or heterocyclic ring having 3 to 7 ring atoms, where in the case of a heterocycle the heteroatoms, preferably 1, 2 or 3 heteroatoms, are selected from the group consisting of N, O and S, in particular an oxygen atom, and where the ring in question may also have fused-on rings and is otherwise unsubstituted or substituted by one or more identical or different radicals selected from the group consisting of halogen, nitro, radicals of the formula $R^1$ which are different from hydrogen, radicals of the formula L* and oxo, where $R^1$ and L* are as defined further below, (c) is linked cyclically with L via a second direct bond or via a heteroatom selected from the group consisting of N, O and S, (d) has two or more substituents from the above groups (a) to (c) together, and where G preferably, including the substituents not indicated by symbols in the formula (I), has from 1 to 30 carbon atoms, in particular from 1 to 20 carbon atoms, very particularly preferably from 1 to 12 carbon atoms, L, L* independently of one another are each $OR^4$, $SR^4$, CN, tetrazolo, $C(OR^5)(OR^6)(OR^7)$, —$Z^1$, —O—$Z^2$, —S—$Z^2$ or —NH—$Z^2$, where $R^4$, $R^5$, $R^6$, $R^7$, $Z^1$ and $Z^2$ are as defined further below and where L may be attached cyclically to the bridge G via a second direct bond or via a heteroatom selected from the group consisting of N, O and S, $Z^1$, $Z^2$ independently of one another are each the radical of an inorganic or organic oxygen acid of the formula $Z^1$-OH or $Z^2$-OH, where the radical is formally formed by removing the hydroxyl group from the acid function, $R^1$ to $R^7$ independently of one another are each a hydrogen atom, $(C_1-C_6)$alkyl, $(C_2-C_6)$alkenyl, $(C_2-C_6)$alkynyl, $(C_3-C_9)$cycloalkyl, $(C_5-C_9)$cycloalkenyl, aryl or heterocyclyl, where each of the last-mentioned radicals is unsubstituted or substituted by one or more radicals selected from the group consisting of amino, hydroxyl, mercapto, cyano, halogen, azido, nitro, $SF_5$, aminosulfonyl, acyl, acylamino, acyloxy, acylthio, $[(C_1-C_4)$alkoxy]carbonyl, mono$(C_1-C_4)$alkylamino, mono$(C_3-C_9)$cycloalkylamino, di$(C_1-C_4)$-alkylamino, $(C_1-C_4)$alkylthio, $(C_2-C_4)$alkenylthio, $(C_2-C_4)$alkynylthio, $(C_3-C_9)$cycloalkylthio, $(C_5-C_9)$cycloalkenylthio, $(C_1-C_4)$alkylsulfinyl, $(C_1-C_4)$alkylsulfonyl, $(C_1-C_4)$alkoxy, $(C_2-C_4)$alkenyloxy, $(C_2-C_4)$alkynyloxy, $(C_3-C_9)$cycloalkoxy, $(C_5-C_9)$cycloalkenyloxy, $(C_3-C_9)$cycloalkyl, $(C_5-C_9)$cycloalkenyl, aryl, substituted aryl, heteroaryl, substituted heteroaryl and, in the case of cyclic radicals, also by $(C_1-C_4)$alkyl, $(C_2-C_4)$alkenyl, $(C_2-C_4)$alkynyl, $(C_1-C_4)$haloalkyl, $(C_2-C_4)$haloalkenyl, $(C_2-C_4)$haloalkynyl, $(C_1-C_4)$hydroxyalkyl and $(C_1-C_4)$alkoxy $(C_1-C_4)$alkyl, where heterocyclyl is a heterocyclic saturated, unsaturated or heteroaromatic ring having preferably 3 to 9 ring atoms and 1 to 3 heteroatoms selected from the group consisting of N, O and S and where heteroaryl is preferably a heteroaromatic ring having preferably 5 to 6 ring atoms and 1 to 3 heteroatoms selected from the group consisting of N, O and S and where the substitutents for substituted aryl or substituted heteroaryl are preferably one or more substituents selected from the group consisting of halogen, nitro, $(C_1-C_4)$alkyl, $(C_1-C_4)$haloalkyl, $(C_1-C_4)$alkoxy, $(C_1-C_4)$haloalkoxy and $(C_1-C_4)$alkylthio, or $R^2$, $R^3$ together with the carbon atom of the group $R^2R^3C=$ are a non-aromatic carbocyclic ring or a heterocyclic ring having 3 to 9 ring atoms and 1 to 4 heteroring atoms selected from the group consisting of N, O and S, which ring is unsubstituted or substituted by one or more radicals selected from the group consisting of halogen, nitro, hydroxyl, oxo, $(C_1-C_4)$alkyl, $(C_1-C_4)$haloalkyl, $(C_1-C_4)$alkoxy, $(C_1-C_4)$haloalkoxy and $(C_1-C_4)$alkylthio, or $R^5$, $R^6$ together with the carbon atom and the adjacent oxygen atoms of the group $C(OR^5)(OR^6)(OR^7)$ are a saturated or unsaturated non-aromatic heterocyclic ring having 4 to 9 ring atoms and 1 to 4 heteroring atoms selected from the group consisting of N, O, P and S, which ring is unsubstituted or substituted by one or more radicals selected from the group consisting of halogen, nitro, hydroxyl, oxo, $(C_1-C_4)$alkyl, $(C_1-C_4)$haloalkyl, $(C_1-C_4)$alkoxy, $(C_1-C_4)$haloalkoxy and $(C_1-C_4)$alkylthio, or the group $C(OR^5)(OR^6)(OR^7)$ together is a bicyclic radical of the formula

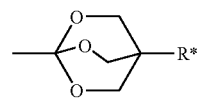

in which

R* is $(C_1-C_4)$alkyl, $(C_1-C_4)$haloalkyl, $(C_1-C_4)$alkoxy, $(C_1-C_4)$haloalkoxy, $(C_1-C_4)$alkylthio or phenyl which is unsubstituted or substituted by one more radicals selected from the group consisting of halogen, nitro, hydroxyl, oxo, $(C_1-C_4)$alkyl, $(C_1-C_4)$haloalkyl, $(C_1-C_4)$alkoxy, $(C_1-C_4)$haloalkoxy and $(C_1-C_4)$alkylthio, for the direct or indirect inhibition of the enzyme adenosine monophosphate deaminase (AMPDA) or adenosine deaminase (ADA), preferably under physiological conditions or analogous aqueous conditions, in particular as herbicides in crop protection or for preparing pharmaceutical compositions for treating diseases which can be treated by inhibiting the enzyme AMPDA or ADA.

The invention also provides all novel compounds of the formula (I) and their salts. Partial structures of the compounds (I) correspond to those of the natural products formycin A (7-amino-3-(β-D-ribofuranosyl)pyrazolo[4,3-d]-pyrimidine) and formycin B (7-oxo-3-(β-D-ribofuranosyl)pyrazolo[4,3-d]-pyrimidine). Already known is deaminoformycin, i.e. the compound of the formula (I), in which A=CH, D=C, E=NH and G—L=β-D-ribofuranosyl; specifically G—L here is a radical of the formula (GL1) where L=hydroxyl

(GL1)

The preparation of deaminoformycin from 7-chloro-3-(β-D-ribofuranosyl)-pyrazolo[4,3-d]pyrimidine is described by G. H. Milne, L. B. Townsend, J. Chem. Soc. Perkin Trans. I, 1972, 2677.

S. Watanabe et al. in J. Antibiotic. Ser. A., 19 (1966) 93 disclosed derivatives of formycin, including, inter alia, deaminoformycin, and they state that they have a fungicidal action against *Xanthomonas oryzae*. The publications mentioned do not describe an inhibition of the enzyme AMPDA or ADA by action of one of the formycin derivatives, nor do they teach their use as herbicides or for pharmaceutical purposes.

Many of the compounds (I) occur in tautomeric forms, i.e. chemical compounds which are formed by rearrangement, preferably by prototrophy (=hydrogen shift) in combination with a migration of double bonds and which are in most cases in an equilibrium with one another. Particular attention should be paid to tautomeric forms of compounds where D=a carbon atom and E=NH, where the hydrogen atom migrates to the other nitrogen atom in the 5-membered ring:

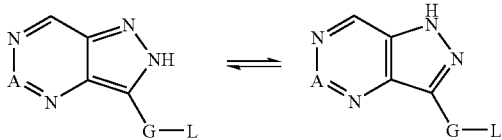

Under acidic to neutral aqueous conditions, the compounds (I) easily add water to form compounds of the formula (I')

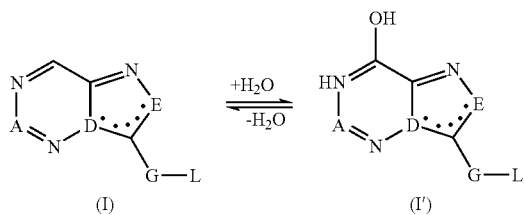

The water addition products (I') also form part of the subject matter of the invention.

The compounds of the formula (I) can form salts by addition of a suitable inorganic or organic acid, such as, for example, HCl, HBr, $H_2SO_4$ or $HNO_3$, but also oxalic acid or sulfonic acids, to a basic group, such as, for example, amino or alkylamino. Suitable substituents which are present in deprotonated form, such as, for example, sulfonic acids or carboxylic acids, can form inner salts with groups which for their part can be protonated, such as amino groups. Salts can also be formed by replacing the hydrogen of suitable substituents, such as, for example, sulfonic acids or carboxylic acids, by an agriculturally suitable cation. These salts are, for example, metal salts, in particular alkali metal salts or alkaline earth metal salts, in particular sodium salts and potassium salts, or else ammonium salts, salts with organic amines or quaternary ammonium salts.

In general, the compounds also occur as a plurality of stereoisomers. Such compounds of the formula (I) contain one or more asymmetric carbon atoms (=asymmetrically substituted carbon atoms) or else double bonds, which are not specifically mentioned in the general formula (I). The possible stereoisomers, which are defined by their specific spatial form, such as enantiomers, diastereomers, Z- and E-isomers, are all embraced by the formula (I).

In principle, the stereoisomers can be obtained by customary methods from mixtures of the stereoisomers or else be prepared by stereoselective reactions in combination with the use of stereochemically pure or enriched starting materials. Compounds (I) which are essentially enantiomerically pure can also be obtained by resolution of racemates by customary methods, for example by crystallization or chiral chromatography.

In the context of the invention, the radicals of the formula G—L which comprise natural sugars are particularly important. Of particular interest are the radicals with the natural sugars and the radicals with the stereochemistry which corresponds to that of the natural sugars.

In the formula (I) and all the formulae hereinbelow, the radicals alkyl, alkoxy, haloalkyl, haloalkoxy, alkylamino and alkylthio and the corresponding unsaturated and/or substituted radicals can in each case be straight-chain or branched in the carbon skeleton. Unless specifically defined otherwise, the lower carbon skeletons, for example having 1 to 6 carbon atoms, in particular 1 to 4 carbon atoms, or, in the case of unsaturated groups, having 2 to 6 carbon atoms, in particular 2 to 4 carbon atoms, are preferred for these radicals. Alkyl radicals, also in the composed meanings, such as alkoxy, haloalkyl, and the like, are, for example, methyl, ethyl, n- or isopropyl, n-, iso-, t- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meaning of the possible unsaturated radicals which correspond to the alkyl radicals and contain at least one double bond and triple bond, respectively, preferably one double bond and triple bond, respectively. Alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Alkylidene, for example in the form $(C_1-C_{10})$alkylidene, is the radical of a straight-chain or branched alkane which is attached via a double bond, the position of the binding site not being fixed. In the case of a branched alkane, the only possible positions are, of course, those where two hydrogen atoms can be replaced by the double bond; examples of radicals are $=CH_2$, $=CH-CH_3$, $=C(CH_3)-CH_3$, $=C(CH_3)-C_2H_5$ or $=C(C_2H_5)-C_2H_5$. This applies correspondingly to cycloalkylidene, such as cyclopentylidene or cyclohexylidene.

Cycloalkyl is a carbocyclic saturated ring system having preferably 3-8 carbon atoms, preferably 3 to 6 carbon atoms, for example cyclopropyl, cyclobutyl, cyclopentyl or cyclohexyl. In the case of substituted cycloalkyl, this includes cyclic systems with substituents, where the substituents are attached to the cycloalkyl radical via a double bond, for example an alkylidene group such as methylidene. Substituted cycloalkyl also includes polycyclic aliphatic systems, such as, for example, bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, adamantan-1-yl and adamantan-2-yl. Cycloalkenyl is a carbocyclic non-aromatic, partially unsaturated ring system having preferably 4-8 carbon atoms, in particular 5 to 7 carbon atoms, for example 1-cyclobutenyl, 2-cyclobutenyl, 1-cyclopentenyl, 2-cyclopentenyl, 3-cyclopentenyl or 1-cyclohexenyl, 2-cyclohexenyl, 3-cyclohexenyl, 1,3-cyclohexadienyl or 1,4-cyclohexadienyl. For substituted cycloalkenyl, the illustrations for substituted cycloalkyl apply correspondingly.

Halogen is, for example, fluorine, chlorine, bromine or iodine. In radical definitions, "halogen" denotes a halogen radical, i.e. a halogen atom. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

A hydrocarbon radical can be straight-chain, branched or cyclic, saturated, unsaturated or aromatic or may contain a combination of identical or different hydrocarbon radicals from those mentioned. "Hydrocarbon radical" embraces, for example, the radicals alkyl, alkenyl, alkynyl, cycloalkyl, cycloalkenyl, cycloalkylalkyl, cycloalkenylalkyl, aryl, such as phenyl or naphthyl, benzyl, phenethyl, etc. A hydrocarbon radical preferably contains 1 to 30 carbon atoms, in particular 1 to 24 carbon atoms.

A heterocyclic radical or ring (heterocyclyl) can be saturated, unsaturated or heteroaromatic; unless defined otherwise, it preferably contains one or more, in particular 1, 2 or 3, heteroatoms in the heterocyclic ring, preferably selected from the group consisting of N, O and S; it is preferably an aliphatic heterocyclyl radical having 3 to 7 ring atoms or a heteroaromatic radical having 5 or 6 ring atoms. The heterocyclic radical can, for example, be a heteroaromatic radical or ring (heteroaryl), such as, for example, a mono-, bi- or polycyclic aromatic system, in which at least one ring contains one or more heteroatoms. It is preferably a heteroaromatic ring having one heteroatom selected from the group consisting of N, O and S, for example pyridyl, pyrrolyl, thienyl or furyl; furthermore preferably, it is a corresponding heteroaromatic ring having 2 or 3 heteroatoms, for example pyrimidinyl, pyridazinyl, pyrazinyl, triazinyl, thiazolyl, thiadiazolyl, oxazolyl, isoxazolyl, pyrazolyl, imidazolyl and triazolyl. Furthermore preferably, it is a partially or fully hydrogenated heterocyclic radical having one heteroatom selected from the group consisting of N, O and S, for example oxiranyl, oxetanyl, oxolanyl (=tetrahydrofuryl), oxanyl, pyrrolinyl, pyrrolidyl or piperidyl. Furthermore preferably, it is a partially or fully hydrogenated heterocyclic radical having 2 heteroatoms selected from the group consisting of N, O and S, for example piperazinyl, dioxolanyl, oxazolinyl, isoxazolinyl, oxazolidinyl, isoxazolidinyl and morpholinyl.

Possible substituents for a substituted heterocyclic radical are the substituents mentioned further below, and additionally also oxo. The oxo group can also be present at the heteroring atoms which can exist in different oxidation states, for example at N and S.

If a skeleton is substituted by "one or more radicals" from a list of radicals (=group) or a generically defined group of radicals, this includes in each case the simultaneous substitution by a plurality of identical and/or structurally different radicals.

Substituted radicals, such as a substituted alkyl, alkenyl, alkynyl, aryl, phenyl, benzyl, heterocyclyl and heteroaryl radical, are, for example, a substituted radical derived from the unsubstituted skeleton, where the substituents are, for example, one or more, preferably 1, 2 or 3, radicals selected from the group consisting of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, alkylsulfonyl and, in the case of cyclic radicals, also alkyl, haloalkyl, alkylthioalkyl, alkoxyalkyl, unsubstituted or substituted mono- and dialkylaminoalkyl and hydroxyalkyl; the term "substituted radicals", such as substituted alkyl etc., includes as substituents, in addition to the saturated hydrocarbon-containing radicals mentioned, corresponding unsaturated aliphatic and aromatic radicals, such as unsubstituted or substituted alkenyl, alkynyl, alkenyloxy, alkynyloxy, phenyl, phenoxy etc. Substituted cyclic radicals having aliphatic moieties in the ring include cyclic systems having substituents which are attached to the ring via a double bond, for example those substituted by an alkylidene group, such as methylidene or ethylidene.

The substituents mentioned by way of example ("first substituent level") can, if they contain hydrocarbon-containing moieties, be, if appropriate, substituted further in these moieties ("second substituent level"), for example by one of the substituents defined for the first substituent level. Further corresponding substituent levels are possible. The term "substituted radical" preferably only embraces one or two substituent levels.

Preferred substituents for the substituent levels are, for example, amino, hydroxyl, halogen, nitro, cyano, mercapto, carboxyl, carboxamide, $SF_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxy-carbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulfinyl, alkylsulfonyl, monoalkyl-aminosulfonyl, dialkylaminosulfonyl, N-alkylaminocarbonyl, N,N-dialkyl-aminocarbonyl, N-alkanoylaminocarbonyl, N-alkanoyl-N-alkylamino-carbonyl, aryl, aryloxy, benzyl, benzyloxy, benzylthio, arylthio, arylamino and benzylamino.

Among the radicals with carbon atoms, preference is given to those having 1 to 6 carbon atoms, preferably 1 to 4 carbon atoms, in particular 1 or 2 carbon atoms. In general, preference is given to substituents selected from the group consisting of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given here to the substituents methyl, methoxy, fluorine and chlorine.

Substituted amino, such as mono- or disubstituted amino, is a radical from the group of the substituted amino radicals which are N-substituted, for example, by one or two identical or different radicals selected from the group consisting of alkyl, alkoxy, acyl and aryl; preferably mono- and dialkylamino, mono- and diarylamino, acylamino, N-alkyl-N-arylamino, N-alkyl-N-acylamino and N-heterocycles; preference is given to alkyl radicals having 1 to 4 carbon atoms; aryl is preferably phenyl or substituted phenyl; for acyl, the definition mentioned further below applies, preferably $(C_1-C_4)$alkanoyl. This applies correspondingly to substituted hydroxylamino or hydrazino.

Unsubstituted or substituted phenyl is preferably phenyl which is unsubstituted or mono- or polysubstituted, preferably up to trisubstituted, by identical or different radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyl, 2-, 3- and 4-chlorophenyl, 2-, 3- and 4-fluorophenyl, 2-, 3- and 4-trichloromethylphenyl, 2-, 3- and 4-trifluorophenyl, 2,4-, 3,5-, 2,5-, 2,6- and 2,3-dichlorophenyl or -difluorophenyl, 2,3,4- or 2,3,5- or 2,4,6- or 2,3,6-trifluoro- and -trichlorophenyl, o-, m- and p-methoxyphenyl.

The radicals $Z^1$ or $Z^2$ of an inorganic or organic oxygen acid which is formally formed by removing a hydroxyl group from the acid function is, for example, the sulfo radical —$SO_3H$, which is derived from sulfuric acid $H_2SO_4$, or the sulfino radical —$SO_2H$, which is derived from sulfurous acid $H_2SO_3$, or, correspondingly, the group $SO_2NH_2$, the phospho radical $-PO(OH)_2$, the group $-PO(NH_2)_2$, $-PO(OH)(NH_2)$, $-PS(OH)_2$, $-PS(NH_2)_2$ or $-PS(OH)(NH_2)$, the carboxyl radical COOH, which is derived from carbonic acid, radicals of the formula $-CO-SH$, $-CS-OH$, $-CS-SH$, $-CO-NH_2$, $-CS-NH_2$, $-C(=NH)-OH$ or $-C(=NH)-NH_2$; also possible are radicals with hydrocarbon radicals or substituted hydrocarbon radicals, i.e. acyl radicals in the widest sense (="acyl").

Acyl is a radical of an organic acid which is formally formed by removing a hydroxyl group from the acid function, where the organic radical in the acid can also be attached to the acid function via a heteroatom. Examples of acyl are the radical $-CO-R$ of a carboxylic acid $HO-CO-R$ and radicals of acids derived therefrom, such as thiocarbonic acid, unsubstituted or N-substituted iminocarboxylic acids or the radicals of carbonic monoesters, N-substituted carbamic acid, sulfonic acids, sulfinic acids, N-substituted sulfonamide acids, phosphonic acids, phosphinic acids.

Acyl is, for example, formyl, alkylcarbonyl, such as $[(C_1-C_4)alkyl]$carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. The radicals can in each case be further substituted in the alkyl or phenyl moiety, for example in the alkyl moiety by one or more radicals selected from the group consisting of halogen, alkoxy, phenyl and phenoxy; examples of substituents in the phenyl moiety are the substituents which have already been mentioned above generally for substituted phenyl. Acyl is preferably an acyl radical in the more restricted sense, i.e. a radical of an organic acid where the acid group is directly attached to the carbon atom of an organic radical, for example formyl, alkylcarbonyl, such as acetyl or $[(C_1-C_4)alkyl]$carbonyl, phenylcarbonyl, alkylsulfonyl, alkylsulfinyl and other radicals of organic acids.

In particular for reasons of better biological activity, preferably herbicidal activity, better selectivity and/or easier preparation, the uses according to the invention of compounds of the formula (I) mentioned or salts thereof which are those in which of particular interest are those in which in the formula (I) individual radicals have one of the preferred meanings already mentioned or mentioned hereinbelow, or, in particular, those in which one or more of the preferred meanings already mentioned or mentioned hereinbelow are combined.

Of particular interest is the use according to the invention of compounds of the formula (I) and their tautomers, their salts and their water addition products (hereinbelow in summary also referred to as "compounds (I)")

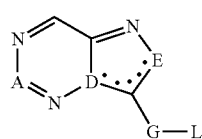

(I)

in which
A is a nitrogen atom or
a group of the formula C—R in which
R is a hydrogen atom, amino, hydroxyl, mercapto, cyano, halogen, azido, nitro, $SF_5$, aminosulfonyl, $(C_1-C_5)$alkanoylamino, $[(C_1-C_4)alkoxy]$-carbonylamino, $(C_1-C_5)$alkanoyl, $[(C_1-C_4)alkoxy]$carbonyl, $(C_1-C_5)$alkanoyloxy, $[(C_1-C_4)alkoxy]$carbonyloxy, mono$(C_1-C_4)$alkyl-amino, mono$(C_3-C_6)$cycloalkylamino, di$(C_1-C_4)$alkylamino, $(C_1-C_4)$alkylthio, $(C_1-C_4)$alkylsulfinyl, $(C_1-C_4)$alkylsulfonyl, $(C_1-C_4)$alkoxy, $(C_3-C_4)$alkenyloxy, $(C_3-C_4)$alkynyloxy, $(C_3-C_6)$cyclo-alkoxy, $(C_5-C_6)$cycloalkenyloxy, $(C_1-C_4)$alkyl, $(C_2-C_4)$alkenyl, $(C_2-C_4)$alkynyl, $(C_3-C_6)$cycloalkyl, $(C_5-C_6)$cycloalkenyl, $(C_1-C_4)$alkyl-aminosulfonyl or di$[(C_1-C_4)alkyl]$aminosulfonyl, where each of the 24 last-mentioned radicals is unsubstituted or substituted in the hydrocarbon moiety by one or more radicals selected from the group consisting of halogen, hydroxyl, amino, nitro, formyl, carboxyl, cyano, thiocyanato, $(C_1-C_4)$alkoxy, $(C_3-C_6)$cycloalkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_6)$cycloalkyl, $(C_3-C_6)$cycloalkylamino, $[(C_1-C_4)alkyl]$carbonyl, $[(C_1-C_4)alkoxy]$-carbonyl, aminocarbonyl, mono$(C_1-C_4)$alkylaminocarbonyl and di$(C_1-C_4)$alkylaminocarbonyl.

A is preferably a nitrogen atom.

Likewise preferably, A is a group of the formula C—R in which R is a hydrogen atom, amino, hydroxyl, mercapto, cyano, halogen, azido, nitro, mono$(C_1-C_4)$alkylamino, di$(C_1-C_4)$alkylamino, $(C_1-C_4)$alkylthio, $(C_1-C_4)$alkoxy, $(C_3-C_4)$alkenyloxy, $(C_3-C_4)$alkynyloxy, $(C_3-C_6)$cycloalkoxy, $(C_1-C_4)$alkyl, where each of the 8 last-mentioned radicals is unsubstituted or substituted in the hydrocarbon moiety by one or more radicals selected from the group consisting of halogen, $(C_1-C_4)$alkoxy, $(C_1-C_4)$haloalkoxy, and $(C_1-C_4)$alkylthio.

R is, in particular, a hydrogen atom, amino, OH, SH, CN, halogen, such as F, Cl, Br or I, $N_3$, $NO_2$, mono$(C_1-C_4)$alkylamino, such as methylamino, di$(C_1-C_4)$alkylamino, such as dimethylamino, or $(C_1-C_3)$alkylthio, such as methylthio, $(C_1-C_3)$alkoxy, such as methoxy, $(C_1-C_3)$alkyl, such as methyl or ethyl, vinyl, ethynyl, $(C_1-C_3)$haloalkyl, such as $CF_3$. Very particularly preferably, R=H.

In the compounds (I) to be used according to the invention,
D is preferably a carbon atom and
E is preferably a group of the formula NH, $(C_1-C_4)$alkyl-N, $-N-OH$, $-N-NH_2$, $-O-$, $-S-$, $-SO-$ or $-SO_2-$, preferably E=NH, in which case the compound is predominantly present as a mixture of the tautomers of the two formulae below:

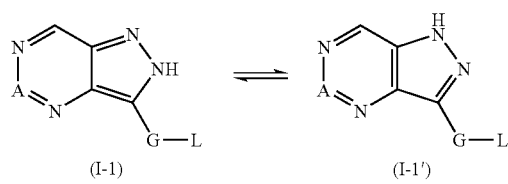

(I-1)    (I-1')

Moreover, preference is given to compounds (I) based on the formulae (I-2), (I-3), (I-4), (I-5) and (I-6):

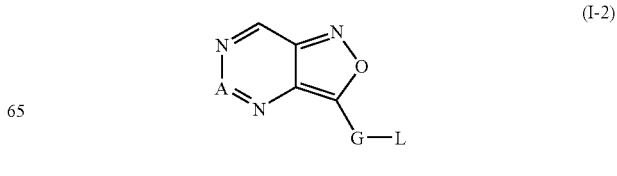

(I-2)

-continued

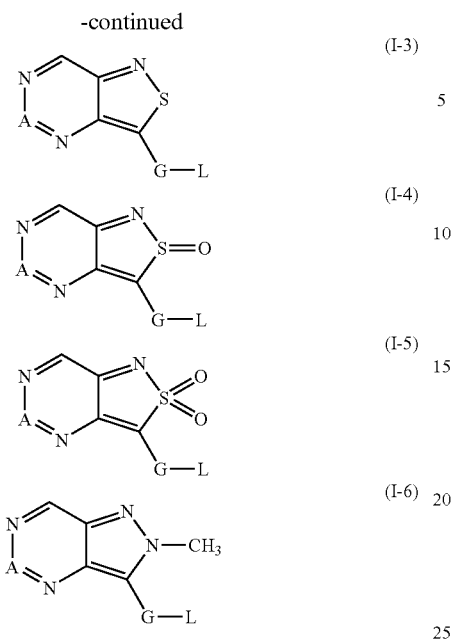

Moreover,

D is preferably a nitrogen atom and

E is preferably a nitrogen atom or a group of the formula C—R°, including compounds (I) based on the formulae (I-7) and (I-8):

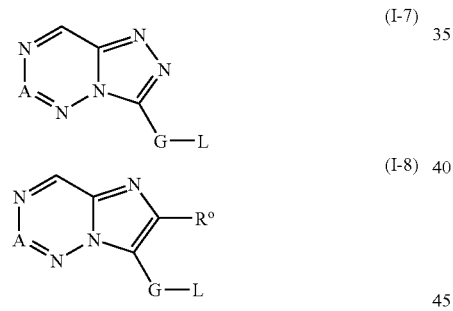

R° is preferably H, OH, $NH_2$, halogen, $GH_3$ or $CF_3$.

In the compounds (I) to be used according to the invention,

G is preferably a divalent straight-chain saturated or unsaturated hydrocarbon bridge having 1 to 8 carbon atoms, preferably 4 to 6 carbon atoms, in the chain, in which one or more $CH_2$ groups, in each case independently of one another, are replaced by O or S, preferably by O, where the bridge in question is unsubstituted or substituted as mentioned above, preferably unsubstituted or (a) substituted by one or more halogen atoms and additionally or alternatively by one or more, preferably 1 to 4, identical or different radicals selected from the group consisting of nitro, radicals of the formula $R^1$ which are different from hydrogen, radicals of the formula $R^2R^3C=$ and radicals of the formula $L^*$, where $R^1$, $R^2$, $R^3$ and $L^*$ are as defined above or as defined further below, (b) carries two or four substituents, in each case two of which together with the linking bridge moiety form a carbocyclic ring having 3 to 6 carbon atoms, preferably 1,2-cyclopentylene, 1,3-cyclopentylene, 1,2-cyclohexylene, 1,3-cyclohexylene, 1,4-cyclohexylene, 1,2-phenylene, 1,3-phenylene or 1,4-phenylene, or a heterocyclic saturated or partially unsaturated ring having 3 to 6 ring atoms or a heteroaromatic ring having 5 or 6 ring atoms, where in the case of a heterocycle the heteroatoms, preferably 1, 2 or 3 heteroatoms, are selected from the group consisting of N, O and S and where the ring in question may also have a fused-on carbocyclic ring having 4 to 6 ring atoms or a fused-on heterocyclic ring having 4 to 6 ring atoms and 1, 2 or 3 heteroatoms selected from the group consisting of N, O and S, the ring being otherwise unsubstituted or substituted by one or more halogen atoms and additionally or alternatively by one or more, preferably 1 to 3, identical or different radicals selected from the group consisting of nitro, radicals of the formula $R^1$ which are different from hydrogen, radicals of the formula $L^*$ and oxo, where $R^1$ and $L^*$ are as defined above or as defined further below, (c) has substituents from the above groups (a) and (b) together.

In the compounds (I) to be used according to the invention,

L, $L^*$ are each preferably, independently of one another, $OR^4$, $SR^4$, CN, tetrazolo, $C(OR^5)(OR^6)(OR^7)$, —$Z^1$, —O—$Z^2$, —S—$Z^2$ or —NH—$Z^2$, where $R^4$, $R^5$, $R^6$, $R^7$, $Z^1$ and $Z^2$ are as defined further below and where L may be attached cyclically to the bridge G via a second direct bond or via a heteroatom selected from the group consisting of N, O and S, preferably O, $Z^1$ is a radical of the formula $COOR^8$, CS—$OR^8$, CO—$SR^8$, CS—$SR^8$ CO—$NR^9$—$SO_2$—$R^8$, CO—$NR^{10}R^{11}$, CS—$NR^{10}R^{11}$, CO—$R^{12}$, CS—$R^{12}$, SO—$R^{12}$, $SO_2R^{12}$, $SO_3R^8$, $SO_2NR^{10}R^{11}$, $SO_2NR^9COR^{12}$, $SO_2NR^9COOR^{12}$, P(=O)($OR^{13}$)($OR^{14}$), P(=S)($OR^{13}$)($OR^{14}$), P(=O)($R^{15}$)($OR^{14}$), P(=O)($OR^{13}$)($NR^{10}R^{11}$), P(=O)($NR^{10}R^{11}$)($NR^{16}R^{17}$), P(=S)($OR^{13}$)($NR^{10}R^{11}$) or P(=S)($NR^{10}R^{11}$)($NR^{16}R^{17}$), preferably a radical of the formula $COOR^8$, CO—$NR^9$—$SO_2$—$R^8$, CO—$NR^{10}R^{11}$, CS—$NR^{10}R^{11}$, $SO_2NR^9COR^{12}$, $SO_2NR^9COOR^{12}$, CO—$R^{12}$, SO—$R^{12}$, $SO_2R^{12}$, $SO_3R^8$, $SO_2NR^{10}R^{11}$, P(=O)($OR^{13}$)($OR^{14}$), P(=S)($OR^{13}$)($OR^{14}$) P(=O)($R^{15}$)($OR^{14}$) P(=O)($OR^{13}$)($NR^{10}R^{11}$), P(=O)($NR^{10}R^{11}$)($NR^{16}R^{17}$), P(=S)($OR^{13}$)($NR^{10}R^{11}$) or P(=S)($NR^{10}R^{11}$)($NR^{16}R^{17}$), in particular a radical of the formula $COOR^8$, CO—$NR^9$—$SO_2$—$R^8$, CO—$NR^{10}R^{11}$, $SO_2NR^9COR^{12}$, $SO_2NR^9COOR^2$, $SO_2NR^{10}R^{11}$, P(=O)($OR^{13}$)($OR^{14}$), P(=S)($OR^{13}$)($OR^{14}$) or P(=O)($OR^{13}$)($NR^{10}R^{11}$)

$Z^2$ is a radical of the formula $COOR^8$, CS—$OR^8$, CO—SR, CS—$SR^8$, CO—$NR^9$—$SO_2$—$R^8$, CO—$NR^{10}R^{11}$, CS—$NR^{10}R^{11}$, CO—$R^{12}$, CS—$R^{12}$, SO—$R^{12}$, $SO_2R^{12}$, $SO_3R^8$, $SO_2NR^{10}R^{11}$, $SO_2NR^9COR^{12}$, $SO_2NR^9COOR^{12}$, P(=O)($OR^{13}$)($OR^{14}$), P(=S)($OR^{13}$)($OR^{14}$), P(=O)($R^{15}$)($OR^{14}$), P(=O)($OR^{13}$)($NR^{10}R^{11}$), P(=O)($NR^{10}R^{11}$)($NR^{16}R^{17}$), P(=S)($OR^{13}$)($NR^{10}R^{11}$) or P(=S)($NR^{10}R^{11}$)($NR^{16}R^{17}$), preferably a radical of the formula CO—$NR^9$—$SO_2$—$R^8$, CO—$NR^{10}R^{11}$, CS—$NR^{10}R^{11}$, $SO_2NR^9COR^{12}$, $SO_2NR^9COOR^{12}$, $CO-R^{12}$, $CS-R^{12}$, $SO-R^{12}$, $SO_2R^{12}$, $P(=O)(OR^{13})(OR^{14})$, $P(=S)(OR^{13})(OR^{14})$, $P(=O)(R^{15})(OR^{14})$ or $P(=O)(OR^{13})(NR^{10}R^{11})$, in particular a radical of the formula $CO-R^{12}$, $CS-R^{12}$, $CO-NR^{10}R^{11}$, $CS-NR^{10}R^{11}$, $P(=O)(OR^{13})(OR^{14})$, $P(=S)(OR^{13})(OR^{14})$, $P(=O)(R^{15})(OR^{14})$ or $P(=O)(OR^{13})(NR^{10}R^{11})$, where $R^8$ to $R^{17}$ are as defined below or further below.

Preferably, $R^1$ to $R^{17}$ independently of one another are each a hydrogen atom, $(C_1-C_6)$alkyl, $(C_2-C_6)$alkenyl, $(C_2-C_6)$alkynyl, $(C_3-C_9)$cycloalkyl, $(C_5-C_9)$cycloalkenyl, aryl or heterocyclyl, where each of the last-mentioned radicals is unsubstituted or substituted by one or more radicals selected from the group consisting of amino, hydroxyl, mercapto, cyano, halogen, azido, nitro, $SF_5$, aminosulfonyl, $(C_1-C_4)$alkanoyl, acylamino, acyloxy, acylthio, $[(C_1-C_4)$alkoxy]-carbonyl, mono$(C_1-C_4)$alkylamino, mono$(C_3-C_9)$cycloalkylamino, di$(C_1-C_4)$alkylamino, $(C_1-C_4)$alkylthio, $(C_2-C_4)$alkenylthio, $(C_2-C_4)$alkynylthio, $(C_3-C_9)$cycloalkylthio, $(C_5-C_9)$cycloalkenylthio, $(C_1-C_4)$alkylsulfinyl, $(C_1-C_4)$alkylsulfonyl, $(C_1-C_4)$alkoxy, $(C_2-C_4)$alkenyloxy, $(C_2-C_4)$alkynyloxy, $(C_3-C_9)$cycloalkoxy, $(C_5-C_9)$cycloalkenyloxy, $(C_3-C_9)$cycloalkyl, $(C_5-C_9)$cycloalkenyl, phenyl, substituted phenyl, heteroaryl, substituted heteroaryl and, in the case of cyclic radicals, also by $(C_1-C_4)$alkyl, $(C_2-C_4)$alkenyl, $(C_2-C_4)$alkynyl, $(C_1-C_4)$haloalkyl, $(C_2-C_4)$haloalkenyl, $(C_2-C_4)$halo-alkynyl, $(C_1-C_4)$hydroxyalkyl and $(C_1-C_4)$alkoxyl$(C_1-C_4)$alkyl, where heterocyclyl is a heterocyclic saturated, unsaturated or heteroaromatic ring having 3 to 6 ring atoms and 1 to 3 heteroatoms selected from the group consisting of N, O and S, where heteroaryl is a heteroaromatic ring having 5 to 6 ring atoms and 1 to 3 heteroatoms selected from the group consisting of N, O and S and where the substituents for substituted phenyl or substituted heteroaryl are preferably one or more radicals selected from the group consisting of halogen, nitro, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$hydroxyalkyl and $(C_1-C_4)$alkoxy$(C_1-C_4)$alkyl, or $R^2$, $R^3$ together with the carbon atom of the group $R^2R^3C=$ are a non-aromatic carbocyclic ring or a heterocyclic ring having 3 to 6 ring atoms and 1 to 3 heteroring atoms selected from the group consisting of N, O and S, which ring is unsubstituted or substituted by one or more radicals selected from the group consisting of halogen, nitro, hydroxyl, oxo, $(C_1-C_4)$alkyl, $(C_1-C_4)$haloalkyl, $(C_1-C_4)$alkoxy, $(C_1-C_4)$haloalkoxy and $(C_1-C_4)$alkylthio, or $R^5$, $R^6$ together with the carbon atom and the adjacent oxygen atoms of the group $C(OR^5)(OR^6)(OR^7)$ are a saturated or unsaturated non-aromatic heterocyclic ring having 3 to 6 ring atoms and 1 to 3 heteroring atoms selected from the group consisting of N, O, P and S, which ring is unsubstituted or substituted by one or more radicals selected from the group consisting of halogen, nitro, hydroxyl, oxo, $(C_1-C_4)$alkyl, $(C_1-C_4)$haloalkyl, $(C_1-C_4)$alkoxy, $(C_1-C_4)$haloalkoxy and $(C_1-C_4)$alkylthio, or $R^8$, $R^9$ or $R^{10}$, $R^{11}$ or $R^{13}$, $R^{14}$ or $R^{14}$, $R^{15}$ or $R^{16}$, $R^{17}$ in each case as a pair and with the atoms of the group defined in each case are a saturated or unsaturated non-aromatic heterocyclic ring having 3 to 9 ring atoms and 1 to 4 heteroring atoms selected from the group consisting of N, O, P and S, which ring is unsubstituted or substituted by one or more radicals selected from the group consisting of halogen, nitro, $(C_1-C_4)$alkyl, $(C_1-C_4)$haloalkyl, $(C_1-C_4)$alkoxy, $(C_1-C_4)$haloalkoxy and $(C_1-C_4)$alkylthio.

Furthermore preferably, in the compounds (I) to be used according to the invention G is a divalent straight-chain saturated or unsaturated hydrocarbon bridge having 1 to 8 carbon atoms, preferably 4 to 6 carbon atoms, in the chain in which one or more $CH_2$ groups, in each case independently of one another, are replaced by O or S, preferably by O, or is a bridge of the formula $-W^1$-cycle-$W^2-$, in which $W^1$, $W^2$ independently of one another are a direct bond, $CH_2$, $CH_2CH_2$, $OCH_2$, $SCH_2$, $CH_2CH_2CH_2$, $CH_2OCH_2$, $CH_2SCH_2$, $OCH_2CH_2$ or $SCH_2CH_2$ and "cycle" is 1,4-cyclohexylene, 1,2-phenylene, 1,3-phenylene, 1,4-phenylene, 1,2-naphthylene, 1,3-naphthylene, 1,4-naphthylene, 1,2-tetrahydronaphthylene, 1,3-tetrahydronaphthylene, 1,4-tetra-hydronaphthylene, 1,2-cyclopentylene, 1,3-cyclopentylene, 1,2-cyclohexylene, 1,3-cyclohexylen, 1,4-cyclohexylene, tetrahydrofuran-2,5-diyl (oxolane), tetrahydrothiophene-2,5-diyl, 2,5-dihydrofuran-2,5-diyl or 2,5-dihydrothiophene-2,5-diyl, where the bridge in question is unsubstituted or substituted by one or more halogen atoms and additionally or alternatively by one or more, preferably 1 to 4, identical or different radicals selected from the group consisting of radicals of the formula $R^1$ which are different from hydrogen, radicals of the formula $R^2R^3C=$ and radicals of the formula L*, where $R^1$, $R^2$, $R^3$ and L* are as defined above or further below, or is additionally or alternatively attached cyclically to L via a second direct bond or via a heteroatom selected from the group consisting of N, O and S.

$R^1$ to $R^{17}$ independently of one another are preferably each a hydrogen atom, $(C_1-C_4)$alkyl, $(C_2-C_4)$alkenyl, $(C_2-C_4)$alkynyl, $(C_3-C_6)$cycloalkyl, $(C_5-C_6)$cycloalkenyl, phenyl or heterocyclyl, where each of the last-mentioned radicals is unsubstituted or substituted by one or more radicals selected from the group consisting of amino, hydroxyl, mercapto, cyano, halogen, azido, nitro, $SF_5$, aminosulfonyl, $(C_1-C_4)$alkanoyl, $(C_1-C_4)$alkanoylamino, benzoylamino, $(C_1-C_4)$alkanoyloxy, $(C_1-C_4)$alkanoylthio, $[(C_1-C_4)$alkoxy]carbonyl, mono$(C_1-C_4)$alkylamino, di$(C_1-C_4)$alkylamino, $(C_1-C_4)$alkylthio, $(C_3-C_4)$alkenylthio, $(C_3-C_4)$alkynylthio, $(C_1-C_4)$alkylsulfinyl, $(C_1-C_4)$alkylsulfonyl, $(C_1-C_4)$alkoxy, $(C_3-C_4)$alkenyloxy, $(C_3-C_4)$alkynyloxy, $(C_3-C_9)$cycloalkoxy, $(C_3-C_9)$cycloalkyl, phenyl, substituted phenyl, heteroaryl, substituted heteroaryl and, in the case of cyclic radicals, also by $(C_1-C_4)$alkyl, $(C_2-C_4)$alkenyl, $(C_2-C_4)$alkynyl, $(C_1-C_4)$haloalkyl, $(C_2-C_4)$haloalkenyl, $(C_2-C_4)$halo-alkynyl, $(C_1-C_4)$hydroxyalkyl and $(C_1-C_4)$alkoxyl$(C_1-C_4)$alkyl, where heterocyclyl is a heterocyclic saturated or unsaturated ring having 3 to 6 ring atoms or a heteroaromatic ring having 5 or 6 ring atoms and in each case 1 to 3 heteroatoms selected from the group consisting of N, O and S and where heteroaryl is preferably a heteroaromatic ring having preferably 5 to 6 ring atoms and 1 to 3 heteroatoms selected from the group consisting of N, O and S and where the substituents for substituted phenyl or substituted heteroaryl are one or more substituents selected from the group consisting of halogen, nitro, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$hydroxy-alkyl and $(C_1-C_4)$alkoxy$(C_1-C_4)$alkyl.

In particular, $R^1$ to $R^4$, $R^8$, $R^{12}$, $R^{13}$, $R^{14}$ and $R^{15}$ independently of one another are each a hydrogen atom, $(C_1-C_4)$alkyl, $(C_2-C_4)$alkenyl, $(C_2-C_4)$alkynyl, $(C_3-C_6)$cycloalkyl or phenyl, where each of the last-mentioned radicals is unsubstituted or substituted by one or more radicals selected from the group consisting of amino, hydroxyl, mercapto, cyano, halogen, azido, nitro, $SF_5$, aminosulfonyl, $(C_1-C_3)$alkanoylamino, benzoylamino, $(C_1-C_4)$alkanoyloxy, $(C_1-C_4)$alkanoylthio, $[(C_1-C_4)$alkoxy]carbonyl, mono$(C_1-C_4)$alkylamino, di$(C_1-C_4)$alkylamino, $(C_1-C_4)$alkylthio, $(C_3-C_4)$alkenylthio, $(C_3-C_4)$alkynylthio, $(C_1-C_4)$alkoxy, $(C_3-C_4)$alkenyloxy, $(C_3-C_4)$alkynyloxy, phenyl, substituted phenyl, heteroaryl, substituted heteroaryl and, in the case of cyclic radicals, also by $(C_1-C_4)$alkyl, $(C_1-C_4)$haloalkyl, $(C_1-C_4)$hydroxyalkyl and $(C_1-C_4)$alkoxyl$(C_1-C_4)$alkyl, where heteroaryl is preferably a heteroaromatic ring having preferably 5 to 6 ring atoms and a heteroatom selected from the group consisting of N, O and S or is heteroaryl from the group consisting of pyrimidinyl, pyridazinyl, pyrazinyl, triazinyl, thiazolyl, thiadiazolyl, oxazolyl, isoxazolyl, pyrazolyl, imidazolyl and triazolyl and where the substituents for substituted phenyl or substituted heteroaryl are preferably one or more radicals selected from the group consisting of halogen, nitro, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$hydroxy-alkyl and $(C_1-C_4)$alkoxy$(C_1-C_4)$alkyl.

Very particularly, $R^1$ to $R^4$, $R^8$, $R^{12}$, $R^{13}$, $R^{14}$ and $R^{15}$ independently of one another are each a hydrogen atom, $(C_1-C_4)$alkyl, such as methyl, ethyl, n- or isopropyl, $(C_1-C_4)$haloalkyl, such as $CF_3$, $(C_1-C_4)$hydroxyalkyl, such as $CH_2OH$, or $CN(C_1-C_4)$alkanoyloxy$(C_1-C_4)$alkyl, such as acetyloxymethyl, di$(C_1-C_4)$alkylamino$(C_1-C_4)$alkyl, such as dimethylaminomethyl, $(C_1-C_4)$alkylthio$(C_1-C_4)$alkyl, such as $CH_3SCH_2$, $(C_1-C_4)$alkoxy$(C_1-C_4)$alkyl, such as methoxymethyl, dimethoxymethyl or ethoxymethyl, or benzyl or phenyl, which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$hydroxyalkyl and $(C_1-C_4)$alkoxy$(C_1-C_4)$alkyl.

In particular, $R^5$ to $R^7$, $R^{10}$, $R^{11}$, $R^{16}$ and $R^{17}$ independently of one another are each a hydrogen atom, $(C_1-C_4)$alkyl, in particular methyl or ethyl, where each of the last-mentioned radicals is unsubstituted or substituted by one or more radicals selected from the group consisting of halogen.

Preferably,

L is $OR^4$, $SR^4$, CN, tetrazolo, $C(OR^5)(OR^6)(OR^7)$, —$Z^1$, —O—$Z^2$, —S—$Z^2$ or —NH—$Z^2$, in particular $OR^4$, CN, —$Z^1$, —O—$Z^2$ or —NH-$Z^2$, where $R^4$, $R^5$, $R^6$, $R^7$, $Z^1$ and $Z^2$ have one of the preferred meanings mentioned.

In particular,

L is hydroxyl, carboxyl, $[(C_1-C_4)$alkoxy]carbonyl, $CONH_2$, $[(C_1-C_4)$alkylamino]carbonyl, $[(C_1-C_4)$alkylsulfonylamino]carbonyl, such as $CONHSO_2CH_3$ or $CONHSO_2C_2H_5$, or $[(C_1-C_4)$halo-alkylsulfonylamino]carbonyl, [cyano$(C_1-C_4)$alkylsulfonylamino]-carbonyl, $(C_1-C_4)$alkylsulfonylamino, $(C_1-C_4)$haloalkylsulfonylamino, cyano-$(C_1-C_4)$alkylsulfonylamino, $(C_1-C_5)$alkanoyloxy, such as acetyloxy, or benzoyloxy, $[(C_1-C_4)$alkoxy]carbonyloxy, such as methoxycarbonyloxy, or $[(C_1-C_4)$alkylamino]carbonyloxy, $(C_1-C_4)$alkoxy, $(C_1-C_4)$alkylthio, $(C_1-C_4)$hydroxyalkoxy, $SO_2NHCONH_2$, $(C_1-C_5)$alkanoylaminosulfonyl, such as $SO_2NHCOCH_3$ or $SO_2NHCOC_2H_5$, or $[(C_1-C_4)$haloalkyl]carbonylaminosulfonyl, $[(C_1-C_4)$alkoxy]carbonylaminosulfonyl, such as $SO_2NHCOOCH_3$ or $SO_2NHCOOC_2H_5$, or $[(C_1-C_5)$haloalkoxy]-carbonylaminosulfonyl, $SO_2NH_2$, di$[(C_1-C_4)$alkyl]aminosulfonyl, $P(=O)(OH)_2$, $P(=S)(OH)_2$, $P(=O)(OR')_2$ or $P(=O)(OH)(OR')$, where in the two last-mentioned formulae R', in each case independently of other radicals R', is $(C_1-C_4)$alkyl, $(C_1-C_4)$haloalkyl, $(C_1-C_4)$hydroxy-alkyl, $(C_1-C_4)$alkanoyl$(C_1-C_4)$alkyl, $(C_1-C_4)$alkanoyloxy$(C_1-C_4)$alkyl or phenyl.

Very particularly,

L is hydroxyl, carboxyl, $[(C_1-C_4)$alkoxy]carbonyl, such as methoxy-carbonyl or ethoxycarbonyl, $[(C_1-C_4)$alkylsulfonylamino]carbonyl, such as $CONHSO_2CH_3$ or $CONHSO_2C_2H_5$, or $[(C_1-C_4)$haloalkyl-sulfonylamino]carbonyl, $[(C_1-C_4)$alkylamino]carbonyl, $(C_1-C_4)$alkylsulfonylamino, $(C_1-C_4)$haloalkylsulfonylamino, cyanomethylsulfonyl-amino, $(C_1-C_5)$alkanoyloxy, such as acetyloxy, or benzoyloxy, $SO_2NH_2$, $P(=O)(OH)_2$, $P(=S)(OH)_2$, $P(=O)(OR')_2$ or $P(=O)(OH)(OR')$, where R' in the two last-mentioned formulae, in each case independently of other radicals R', is $(C_1-C_4)$alkyl, $(C_1-C_4)$haloalkyl, $(C_1-C_4)$hydroxyalkyl, $(C_1-C_4)$alkanoyl$(C_1-C_4)$alkyl, $(C_1-C_4)$alkanoyloxy$(C_1-C_4)$alkyl or phenyl.

Furthermore preferably,

L is hydroxyl, carboxyl, $[(C_1-C_4)$alkoxy]carbonyl, methoxycarbonyl, ethoxycarbonyl, $CONH_2$, $CONHSO_2CH_3$, $CONHSO_2C_2H_5$, acetoxy or benzoyloxy, $SO_2NH_2$, $P(=O)(OH)_2$, $P(=S)(OH)_2$, $P(=O)(OR')_2$, where R'=methyl, ethyl, n-propyl, isopropyl, n-butyl, isobutyl, sec-butyl, tert-butyl, phenyl or $(C_1-C_4)$alkanoyloxy$(C_1-C_4)$alkyl.

L* is preferably a radical selected from the group of the preferred radicals defined for L, in particular $OR^4$, O—$Z^2$ or —S—$Z^2$, in particular $OR^4$ or —$Z^2$, where $R^4$ and $Z^2$ have one of the preferred meanings mentioned. Particularly preferably, L*=hydroxyl, $(C_1-C_5)$alkanoyloxy, such as acetyloxy or benzoyloxy, $[(C_1-C_4)$alkoxy]carbonyloxy, such as methoxy-carbonyloxy, or $(C_1-C_4)$alkoxy, $(C_1-C_4)$alkylthio or $(C_1-C_4)$hydroxyalkoxy, in particular hydroxyl or acetoxy.

Particularly preferably, the group G—L, including substituents, is a radical of a cyclic sugar molecule, in particular the ribosefuranosyl radical.

Particular preference is also given to the respective salts of the acidic radicals mentioned above as being preferred.

Preference is given to compounds (I) which contain a combination of two or more of the radicals mentioned as being preferred.

Particularly preferably, the radicals in the formula (I) which are defined in a general manner are also the radicals specifically mentioned in the working examples and the examples in the tables, or homologous radicals thereof, or radicals from the corresponding generic group, in particular in the combinations of preferred radicals mentioned in the given examples.

The invention also provides processes for preparing the compounds of the formula (I), their salts, tautomers and water addition compounds, which comprise a) reducing a compound of the formula (II)

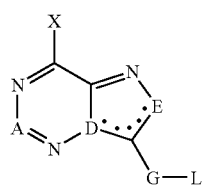

(II)

in which X is a leaving group to the compound of the formula (I) or b) reducing a compound of the formula (III)

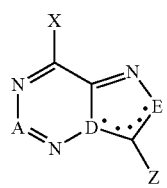

(III)

in which X is a leaving group and Z is a precursor of the radical G—L to the compound of the formula (III')

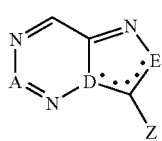

(III')

in which Z is as defined in formula (III), and then modifying the compound (III) at the group Z such that the compound (I) is obtained, c) modifying a compound of the formula (III') in which Z is a precursor of the radical G—L at the group Z such that the compound (I) is obtained, or d) if A is a group of the formula C—R, cyclizing a compound of the formula (III'')

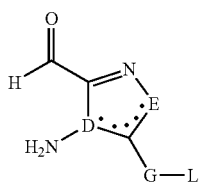

(III'')

with a compound of the formula (III''')

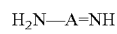

in which A is a group C—R to give the compound of the formula (I), where the symbols A, D, E, G, L and R in the formulae (II), (III), (III'), (III'') and (III''') are as defined in formula (I), unless specifically defined otherwise.

Several methods are suitable for reducing the compound (II) to the compound (I) or the compound (III) to the compound (III'):

In the case of X=halogen, such as chlorine, for example, the chlorine atom can be exchanged reductively for a hydrogen atom under the conditions of a catalytic hydrogenation, for example using $H_2$/Pd; cf. the method of G. H. Milne et al., J. Chem. Soc. Perkin Trans. I (1972) 2677. The compound of the formula (II) mentioned where X=chlorine can be obtained here from the compound (II) where X=OH, which is present in the keto form (II-a),

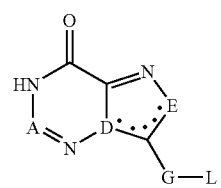

(II-a)

by reaction with $POCl_3$. The corresponding thioketone [=compound (II-a')] can be obtained from the compound (II-a) by reaction with $P_2S_5$, or from the compound (II), X=Cl, by reaction with thiourea, and can then be converted into the compound (I) by reduction with Raney-nickel; this applies correspondingly to the preparation of the compound (III), X=Cl, from the ketone (III-a) [=compound as (II-a), but G—L replaced by the radical Z] and its conversion into the corresponding thioketone (III-a');

cf. Methods of J. Chem. Soc. (C) (1971) 2443 and R. Kandasamy et al., J. Med. Chem. 29 (1986) 2231, J. J. Fox et al. J. Am. Chem. Soc. 80 (1958) 1669 and K. Poreba et al., Acta Pol. Pharm. Drug Research 51 (1994) 355-358.

The compounds of the formulae (II) and (III) where X=alkylthio, for example methylthio, can likewise be converted into the compound (I) by reduction with Raney-nickel. The methylthio compound is obtainable from the thioketone (II-a') mentioned by deprotonation, for example using sodium hydride, and alkylation with methyl iodide;

cf. Methods of J. Chem. Soc. (C) (1971) 2443, R. Kandasamy et al., J. Med. Chem. 29 (1986) 2231, A. Hampton et al., J. Am. Chem. Soc. 78 (1956) 5695 and R. J. Rousseau et al., J. Med. Chem. 15 (1972) 214.

Analogously to the methylthio compound, the method employing Raney-nickel also succeeds with the corresponding selenium compounds (II) and (III), $X=SeCH_3$. The latter compound can be prepared from the chloro compound (II), X=Cl, by reaction with selenourea $Se=C(NH_2)_2$, deprotonation with sodium methoxide and alkylation with methyl iodide; cf. J. A. Milne et al., J. Chem. Soc. Perkin Trans. I (1972) 2677.

A further alternative is via the compound (II) or (III) where X=amino, where the amino group can be removed reductively by reaction with butyl nitrite in THF. The amino compound can be obtained from the ketone (II-a) or (III-a)

or from the methylthio compound (II) or (III), in each case X=SCH$_3$, by reaction with NH$_3$; J. Chem. Soc. (C), 1971, 2443, K. Kandasamy et al., J. Med. Chem. 29 (1986) 2231 and V. Nair et al., Synthesis (1984) 401.

A further alternative makes use of the compound (II) or (III) where in each case X=NHNH$_2$, where the hydrazino group can be removed by reaction with mercury oxide. The hydrazino compound can likewise be obtained from the chloro compound (II) or (III), in each case X=Cl, or from the methylthio compound (II) or (III), in each case X=SCH$_3$, by reaction with hydrazine; cf. J. Chem. Soc. (C), 1971, 2443, C. B. Reese et al., Tetrahedron, 30 (1994) 9195 and C. C. Tzeng et al.; J. Chem. Soc. Perkin Trans. I, 1994, 2253.

To prepare the compounds of the formula (I), the compounds of the formula (III'), in which Z is a precursor of the radical G—L, are modified at the group To prepare the compounds of the formula (I), the compounds of the formula (III'), in which Z is a precursor of the radical G—L, are modified at the group Z such that the compound (I) with the desired group G—L is obtained. For the derivatization reactions, a broad spectrum of generally known or customary methods is available to persons skilled in the art.

Of particular interest are groups of the formula Z from which the radical G—L is obtained by removal of protective groups on hydroxyl groups or amino groups and/or by acylation with an organic acid or reaction with an inorganic acid or an acid derivative thereof.

One example is the removal of one or more tri(alkyl/phenyl) silyl groups from the corresponding compounds (III') in which Z contains one or more tri(alkyl/phenyl) silyloxy groups, to give compounds (I) in which L contains a hydroxyl group and/or G contains further hydroxyl groups. Removal is effected by customary methods, for example in many cases using tetrabutylammonium fluoride in an organic solvent. The resulting compound (I) can subsequently be modified further, for example by phosphorylation or acylation, to give compounds (I) in which L is a phosphate ester group or an acyloxy group.

Further suitable protecting groups are 1,3-dioxolanes, benzyl ethers, acylates, ethers, tetrahydropyran ethers, preferably protective groups which are known or customary in sugar chemistry; cf. J. Falbe, M. Regitz (Ed.), Römpp Chemie Lexikon, 9th edition, vol. 5 (1992), section "Schutzgruppen" [Protective groups] and literature cited therein.

Z is preferably a radical of a natural sugar, in particular a ribosyl radical, which is further modified on one or more hydroxyl groups by protective groups.

A further synthesis possibility for compounds (I) in which A is a group of the formula C—R is to construct the heterocyclic six-membered ring starting from a compound of the formula (III") which is reacted with a compound of the formula (III''') (H$_2$N—A=NH where A is CR) under condensing conditions to give a bicycle. If appropriate, the reaction is carried out in the presence of an acidic or basic catalyst, employing means for removing or for trapping the water of reaction and one molar equivalent of ammonia.

Water addition compounds based on the compounds of the formula (I) can be obtained by addition of water under aqueous acidic to neutral conditions.

The following acids are suitable for preparing the acid addition salts of the compounds of the formula (I): hydrohalic acids, such as hydrochloric acid or hydrobromic acid, furthermore phosphoric acid, nitric acid, sulfuric acid, mono- or bifunctional carboxylic acids and hydroxycarboxylic acids, such as acetic acid, maleic acid, succinic acid, fumaric acid, tartaric acid, citric acid, salicylic acid, sorbic acid or lactic acid, and sulfonic acids, such as p-toluenesulfonic acid or 1,5-naphthalenedisulfonic acid. The acid addition compounds of the formula (I) can be obtained in a simple manner by customary methods for forming salts, for example by dissolving a compound of the formula (I) in water or in a suitable organic solvent, such as, for example, methanol, acetone, methylene chloride or petroleum ether or corresponding aqueous-organic solvents, and adding the acid at temperatures from 0 to 100° C. Isoation and purification succeeds in a known or customary manner, for example in a simple manner by filtering off and, if appropriate, washing with an inert organic solvent.

The base addition salts of the compounds of the formula (I) are preferably prepared in inert polar solvents, such as, for example, water, methanol or acetone, at temperatures from 0 to 100° C. Suitable bases for preparing the salts according to the invention are, for example, alkali metal carbonates, such as potassium carbonate, alkali metal and alkaline earth metal hydroxides, for example NaOH or KOH, alkali metal and alkaline earth metal hydrides, for example NaH, alkali metal and alkaline earth metal alkoxides, for example sodium methoxide, potassium tert-butoxide, or ammonia or ethanolamine.

Intermediates of the formula (II), (II-a), (III) or (III-a) where in each case D=C and E=N can be obtained as follows, according to scheme 1, scheme 2, scheme 3 or scheme 4:

Scheme 1

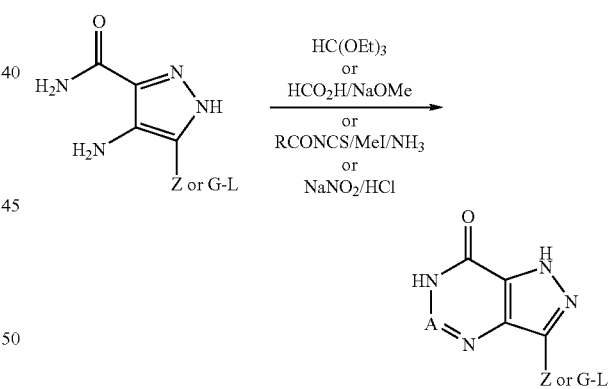

Me=methyl, Et=ethyl

The reactions shown in scheme 1 are known or can be carried out analogously to the known reactions; cf. J. G. Buchanan et al., J. Chem. Soc. Perkin Trans. I, (1986) 1267; A. F. Lewis et al., J. Am. Chem. Soc. 104 (1982) 1073; J. W. Hennen et al., J. Org. Chem., 50 (1985) 1741; G. A. Ivanovics et al., J. Org. Chem. 39 (1974) 3651 and B. Rayner et al., J. Heterocycl. Chem. 10 (1973) 417 and the literature cited in these publications. Using orthoformate or formic acid, the product in which A=CH is obtained. The variant using R—CO—N=C=S, iodomethane and ammonia affords the product where A=—C—NH$_2$, and the use of sodium nitrite results in a product where A=N.

Scheme 2

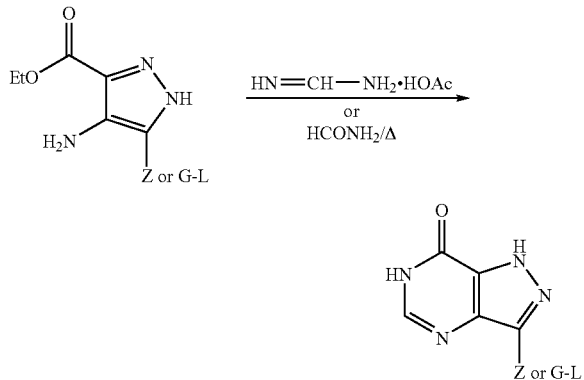

Et=ethyl, Ac=acetyl

The reactions shown in scheme 2 are known or can be carried out analogously to known reactions; cf. G. J. Ellames et al., J. Chem. Soc. Perkin Trans. I, (1985) 2087, J. Wierzchowski et al., J. Chem. Acta Biochemica Polonica 27 (1980) 35 and L. Kalvoda, Coll. Czech. Chem. Commun., 43 (1978) 1431 and the references given therein. Accordingly, the ring closure to give the keto compound of the type (II-a) or (III-a) is possible using formamide or formamidine/acetic acid.

Scheme 3

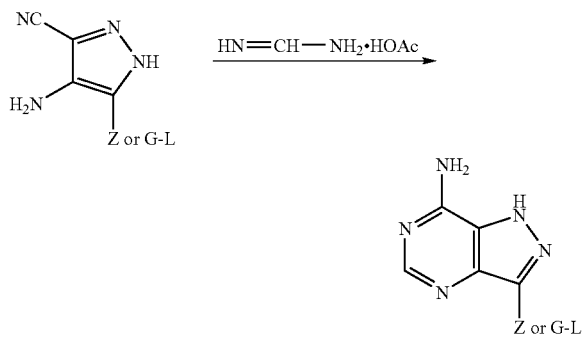

The reaction according to scheme 3 to give the amino compounds of the type (II) and (III) is described, for example, in J. W. Hennen et al., J. Org. Chem., 50 (1985) 1741 and G. J. Ellames et al., J. Chem. Soc. Perkin Trans. I, (11985) 2087 and the literature quoted therein.

Scheme 4

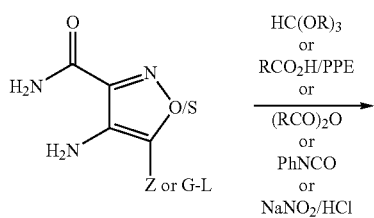

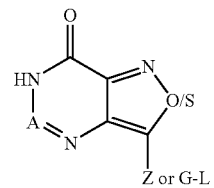

Scheme 4 summarizes several alternatives for preparing the compounds of the type (II-a) and (III-a), in which E=O or S. For the preparation with trialkyl orthoformate (A=CH) or carboxylic acids RCOOH in combination with ethyl polyphosphate ester (PPE) where in the product A=CR see, for example, K. Poreba et al., II Farmaco 49 (1994) 529.

Compounds having a thiazole ring are for instance prepared by the trialkyl orthoformate method or using phenyl isocyanate PhNCO, as described in S. A. El Maaty et al., Bull. Fac. Pharm. Cairo Univ. 29 (1991) 41 and S. A. El Maaty et al., Egypt J. Pharm. Sci. 34 (1993) 421, respectively. The sodium nitrite method has already been mentioned in scheme 1 and gives compounds where A=N.

Intermediates of the formula (II-a), (II), (III) or (III-a) where in each case D=N and E=N or C—R° can be obtained as follows, according to scheme 5, scheme 6 and scheme 7:

Scheme 5

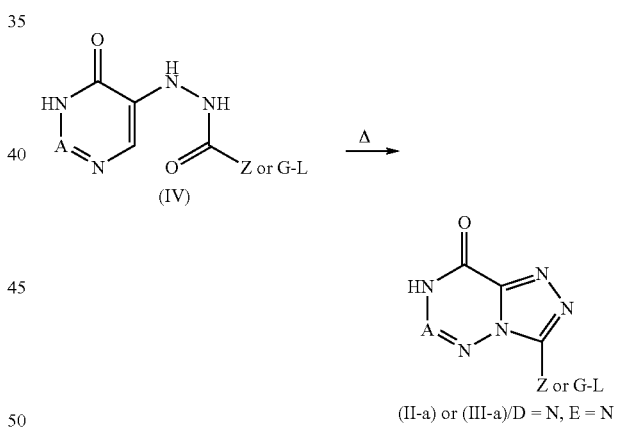

The ring closure according to scheme 5 to give the fused-on triazole ring is effected by heating, for example to up to 200° C., in high-boiling solvents, such as ethylene glycol; see, for example, B. K. Bhattacharya et al., J. Heterocycl. Chem. 30 (1993) 1341, K. Ramasamy et al., J. Med. Chem. 29 (1986) 2231 and T. S. Rao et al., Nucleosides Nucleotides, 14 (1995) 1601.

The corresponding chloro-substituted compounds can be obtained by adding chlorinating agents in the thermal cyclization (see scheme 6). This variant and the chloro compounds of the formulae (II) and (III) where in each case X is chlorine (summarily represented by the formula (V), R*=G—L or Z) are novel and also form part of the subject matter of the invention.

Scheme 6

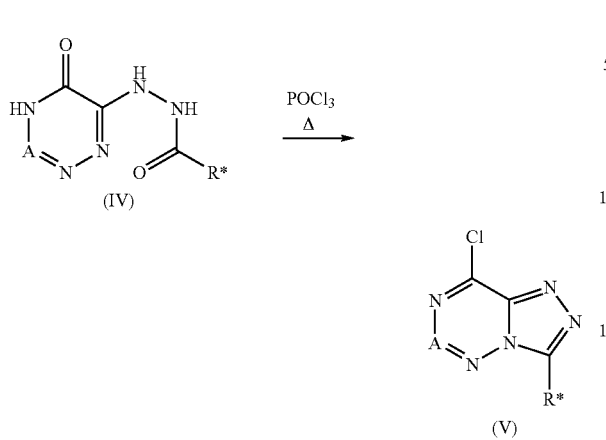

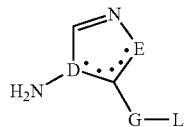

The variant according to scheme 6 is carried out, for example, by heating a solution of the starting material in an inert organic solvent with addition of chlorinating agents, such as $SO_2Cl_2$, $POCl_3$, $PCl_3$, $PCl_5$ etc., or directly without additional solvent in a mixture with preferably liquid chlorinating agents, such as phosphorus oxychloride, at suitable temperatures, for example at from 0 to 200° C., preferably from 50 to 160° C., in particular using $POCl_3$ at reaction temperatures of up to reflux temperature.

Suitable for preparing compounds (II) or (III) where in each case X=alkylthio and with a fused-on imidazole ring, i.e. D=N and E=CH, (both represented by formula (VI), R*=G—L or Z) is the reaction according to scheme 7:

Scheme 7

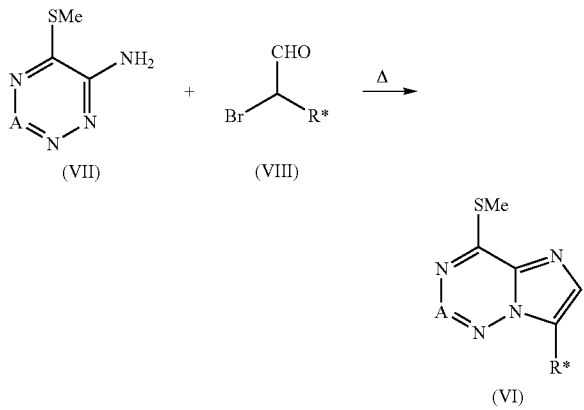

The reaction can be carried out, for example, in an inert organic solvent, such as in optionally halogenated aromatic hydrocarbon, for example toluene or xylene, in the presence of a base, such as potassium carbonate. In the last-mentioned case, the water of reaction can be removed azeotropically. The ring closure reaction according to scheme 7 and its end products are novel and also form part of the subject matter of the invention.

The compounds of the formula (III″) can be obtained from compounds of the formula by formylation. The starting materials are accessible by customary ring synthesis reactions.

The last-mentioned ring synthesis reactions and other synthesis routes to the desired heterocyclic systems are described in M. A. E. Shaban, Advances in Heterocyclic Chemistry 1998, 70, 163. Methods for preparing the radicals of the formulae G—L and Z are given in the publications already mentioned, in U.S. Pat. No. 5,731,432, in M. D. Erion et al, J. Am. Chem. Soc., 1999, 121, 308, and in the Preparation Examples (see further below).

Solvents referred to as "inert solvents" in the above process variants are to be understood as meaning in each case solvents which are inert under the reaction conditions in question, but which need not be inert under any reaction conditions.

Hereinbelow, the compounds of the formula (I) according to the invention, their tautomers, water addition compounds and their salts are collectively referred to a "compounds (I)" or "compounds according to the invention".

Collections of compounds (I) which can be synthesized by the abovementioned process may also be prepared in a parallel manner where the process may be carried out manually, partially automated or fully automated. In this case, it is possible, for example, to automate the procedure of the reaction, the work-up or the purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom, 1997, pages 69 to 77.

A number of commercially available apparatuses as they are offered by, for example, Stem Corporation, Woodrolfe Road, Tollesbury, Essex, CM9 8SE, England, or H+P Labortechnik GmbH, Bruckmannring 28, 85764 Oberschleißheim, Germany may be used for the parallel procedure of the reaction and work-up. For the parallel purification of compounds (I), or of intermediates obtained during the preparation, use may be made, inter alia, of chromatography apparatuses, for example those from ISCO, Inc., 4700 Superior Street, Lincoln, Nebr. 68504, USA. The apparatuses mentioned lead to a modular procedure in which the individual process steps are automated, but manual operations have to be performed between the process steps. This can be avoided by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to the methods described here, compounds (I) may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Verlag Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131-5135), in which products from IRORI, 11149 North Torrey Pines Road, La Jolla, Calif. 92037, USA, are employed, may be partially automated. The automation of solid-phase-supported parallel synthesis is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation methods described here give compounds (I) in the form of collections of substances known as libraries. The present invention also relates to libraries of the compounds (I) which contain at least two compounds (I), and precursors thereof.

The compounds (I) inhibit the activity of the enzyme AMPDA which occurs in higher living organisms, inter alia in humans, animals and plants, directly or at least indirectly under physiological conditions where these compounds, as precursors of directly acting enzyme inhibitors, are converted into the latter. Many compounds (I) also inhibit, after administration under physiological conditions, the enzyme ADA which has been demonstrated to be present in humans and animals. Physiological conditions are understood to include not only in vivo conditions but generally those where phosphorylations and hydrolyses can take place. The substrates adenosine monophosphate and adenosine, respectively, are common to the enzymes of the different organisms. In general, however, the enzymes AMPDA or ADA have, depending on the organisms, variations in the amino acid sequence and thus in the structure. The compounds (I) inhibit, directly or indirectly, the enzymes AMPDA and ADA in different kinds of living organisms. Using standard methods for enzyme tests, inhibitory effects can be observed, for example, on the enzymes AMPDA or ADA originating from rabbit or bovine tissues. Likewise, inhibitory effects are observed on AMPDA obtained from plant species such as peas. Inhibition of 50 percent of the enzyme activity is generally achieved at a concentration ($IC_{50}$) of up to 1000 µmol/l, preferably up to 500 µmol/l, in particular up to 50 µmol/l.

Based on the inhibition of the enzyme and, if appropriate, other properties which are not yet known in detail of the individual compounds (I), biological actions of the compounds (I) are observed in a broad area of applications.

The direct or indirect inhibitory effect (enzyme inhibition) can be employed, for example, for controlling undesirable vegetation or for controlling harmful plants in crops of useful plants which are naturally tolerant to the inhibitor or which have been obtained as tolerant plants by particular measures, such as mutations and selection of the tolerant mutants, or by genetic engineering.

Accordingly, the invention also provides the use of the compounds (I) as herbicides for the non-selective or selective use in agriculture, horticulture or industry. This includes, for example, the use for controlling undesirable vegetation in plantings such as fruit plantings, rubber plantings or oil tree plantings, or on non-crop land, such as paths, squares, gaps between paving stones, railway embankments, etc.

The compounds of the formula (I) according to the invention and their salts have excellent herbicidal activity against a broad spectrum of economically important mono-cotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence.

Specifically, examples may be mentioned of some representatives of the monocotyledonous and dicotyledonous weed flora which can be controlled by the compounds according to the invention, without these being a restriction to certain species.

Examples of weed species on which the active compounds act efficiently are, from amongst the monocotyledons, *Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea*, and also *Cyperus* species predominantly from the annual sector and from amongst the perennial species such as *Agropyron, Cynodon, Imperata* and *Sorghum*, and also perennial *Cyperus* species.

In the case of the dicotyledonous weed species, the spectrum of action extends to species such as, for example, Galium, Viola, Veronica, Lamium, *Stellaria, Amaranthus, Sinapis, Ipomoea, Matricaria, Abutilon* and *Sida* from amongst the annuals, and *Convolvulus, Cirsium, Rumex* and *Artemisia* in the case of the perennial weeds. Moreover, herbicidal activity is observed in connection with dicotyledonous weeds such as *Ambrosia, Anthemis, Carduus, Centaurea, Chenopodium, Cirsium, Convolvulus, Datura, Emex, Galeopsis, Galinsoga, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium*.

The active ingredients according to the invention also effect outstanding control of weeds which occur under the specific conditions of rice growing such as, for example, *Sagittaria, Alisma, Eleocharis, Scirpus* and *Cyperus*.

If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

Although the compounds according to the invention have an excellent herbicidal activity against monocotyledonous and dicotyledonous weeds, crop plants of economically important crops, for example wheat, barley, rye, rice, corn, sugar beet, cotton and soya, are not damaged at all, or only to a negligible extent, with certain compounds. For these reasons, the present compounds are highly suitable for selectively controlling undesired plant growth in plantings of agriculturally useful plants.

In addition, the compounds according to the invention have outstanding growth-regulating properties in crop plants. They engage in the plant metabolism in a regulating manner and can thus be employed for the targeted control of plant constituents and for facilitating harvesting, such as for example by provoking desiccation and stunted growth. Furthermore, they are also suitable for generally regulating and inhibiting undesirable vegetative growth, without destroying the plants in the process. Inhibition of vegetative growth plays an important role in many monocotyledonous and dicotyledonous crops because lodging can be reduced hereby, or prevented completely.

Owing to their herbicidal and plant-growth-regulatory properties, the compounds (I) can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested product are known.

The use of the compounds (I) according to the invention in economically important transgenic crops of useful and ornamental plants, for example of cereal, such as wheat, barley, rye, oats, millet, rice, maniok and corn, or else in crops of sugar beet, cotton, soya, oilseed rape, potato, tomato, peas and other vegetable species is preferred.

The compounds (I) can preferably be used as herbicides in crops of useful plants which are resistant or which have been made resistant by genetic engineering toward the phytotoxic effects of the herbicides.

Conventional ways of preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of

- genetically engineered changes in crop plants in order to modify the starch synthesized in the plants (for example WO 92/111376, WO 92/14827 and WO 91/19806),
- transgenic crop plants which are resistant to certain herbicides of the glufosinate—(cf., for example, EP-A 0 242 236, EP-A 0 242 246) or glyphosate-type (WO 92/00377), or of the sulfonylurea-type (EP-A 0 257 993, U.S. Pat. No. 5,013,659),
- transgenic crop plants, for example cotton, having the ability to produce Bacillus thuringiensis toxins (Bt toxins) which impart resistance to certain pests to the plants (EP-A 0 142 924, EP-A 0 193 259),
- transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423-431. In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end, it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cell. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

The compounds (I) according to the invention can preferably be used in transgenic crops which are resistant to herbicides selected from the group consisting of the sulfonylureas, glufosinate-ammonium or glyphosate-isopropylammonium and analogous active compounds.

When using the active compounds according to the invention in transgenic crops, in addition to the effects against harmful plants which can be observed in other crops, there are frequently effects which are specific to the application in the respective transgenic crop, for example a modified or specifically broadened spectrum of weeds which can be controlled, modified application rates which can be used for the application, preferably good combinability with the herbicides to which the transgenic crop is resistant, and an effect on the growth and the yield of the transgenic crop plants.

The invention therefore also provides for the use of the compounds (I) according to the invention as herbicides for controlling harmful plants in transgenic crop plants.

The compounds according to the invention can be applied in the customary formulations in the form of wettable powders, emulsifiable concentrates, sprayable solutions, dusts or granules. The invention therefore also provides herbicidal and plant-growth-regulating compositions comprising compounds (I).

The compounds (I) can be formulated as agrochemical compositions in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes.

These individual formulation types are known in principle and are described, for example, in Winnacker-Küchler, "Chemische Technologie" [Chemical Technology], Volume 7, C. Hauser Verlag Munich, 4th edition 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation auxiliaries, such as inert materials, surfactants, solvents and other additives, are likewise known and are described, for example, in: Watkins, "Handbook of Insecticide Dust Diluents and Carriers", 2nd ed., Darland Books, Caldwell N. J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th edition 1986.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Wettable powders are preparations which are uniformly dispersible in water and which, in addition to the active compound and as well as a diluent or inert substance, also contain surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane6,6'-disulfonate, sodium dibutylnaphthalenesulfonate or else sodium oleoylmethyltaurinate. To prepare the wettable powders, the herbicidally active compounds are finely ground, for example in customary apparatuses such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethyl-formamide, xylene or else relatively high-boiling aromatics or hydrocarbons or mixtures of the organic solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth.

Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by the customary processes, such as spray-drying, fluidized-bed granulation, disk granulation, mixing using high-speed mixers, and extrusion without solid inert material. For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 1471f; "Perry's Chemical Engineer's Handbook", 5th ed., McGraw-Hill, New York 1973, pp. 8-57.

For further details on the formulation of crop protection products, see for example G. C. Klingman, "Weed Control as a Science", John Wiley and Sons., Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations generally contain from 0.1 to 99% by weight, in particular from 0.1 to 95% by weight, of compound (I) (active compound), or of a mixture of the active compound with other active compounds.

In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules, the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, anti-foams, evaporation inhibitors and pH and viscosity regulators which are customary in each case.

The compounds of the formula (I) or their salts can be used as such or combined in the form of their preparations (formulations) with other pesticidally active compounds, such as, for example, insecticides, acaricides, nematicides, herbicides, fungicides, safeners, fertilizers and/or growth regulators for example as finished formulations or tank mixes. Suitable active compounds which can be combined with the active compounds according to the invention in mixed formulations or in a tank mix are, for example, known active compounds, whose effect is based on an inhibition of the metabolism in plants, for example, acetolactate synthase, acetyl-CoA carboxylase, PS I, PS II, HPPDO, phytoene desaturase, protoporphyrinogen oxidase, glutamine synthetase, cellulose biosynthesis, 5-enolpyruvylshikimate-3-phosphate synthetase in plants. Such compounds, and also other compounds that can be used, with a mechanism of action that is, in some cases, unknown or different, are described, for example, in Weed Research 26, 441-445

(1986), or in "The Pesticide Manual", 11$^{th}$ edition 1997 (hereafter also abbreviated to "PM") and 12$^{th}$ edition 2000, The British Crop Protection Council and the Royal Soc. of Chemistry (publisher), and in the literature cited therein. For example, the following active compounds may be mentioned as herbicides which are known from the literature and which can be combined with the compounds of the formula (I) (note: the compounds are either referred to by the "common name" in accordance with the International Organization for Standardization (ISO) or by the chemical names, if appropriate together with a customary code number):

acetochlor; acifluorfen(-sodium); acionifen; AKH 7088, i.e. [[[1-[5-[2-chloro-4-(trifluoromethyl)phenoxy]-2-nitrophenyl]-2-methoxyethylidene]amino]oxy]-acetic acid and its methyl ester; alachlor; alloxydim(-sodium); ametryn; amicarbazone; amidochlor, amidosulfuron; amitrol; AMS, i.e. ammonium sulfamate; anilofos; asulam; atrazine; azafenidin; azimsulfuron (DPX-A8947); aziprotryn; barban; BAS 516H, i.e. 5-fluoro-2-phenyl-4H-3,1-benzoxazin-4-one; beflubutamide; benazolin(-ethyl); benfluralin; benfuresate; bensulfuron(-methyl); bensulide; bentazone; benzobicyclone; benzofenap; benzofluor; benzoylprop(-ethyl); benzthiazuron; bialaphos; bifenox; bispyribac(-sodium); bromacil; bromobutide; bromofenoxim; bromoxynil; bromuron; buminafos; busoxinone; butachlor; butafenacil; butamifos; butenachlor; buthidazole; butralin; butroxydim; butylate; cafenstrole (CH-900); carbetamide; cafentrazone(-ethyl) (ICI-A0051); caloxydim; CDAA, i.e. 2-chloro-N,N-di-2-propenylacetamide; CDEC, i.e. 2-chloroallyl diethyldithiocarbamate; chlomethoxyfen; chloramben; chlorazifop-butyl; chlormesulon (ICI-A0051); chlorbromuron; chlorbufam; chlorfenac; chlorflurecol-methyl; chloridazon; chlorimuron(-ethyl); chlornitrofen; chlorotoluron; chloroxuron; chlorpropham; chlorsulfuron; chlorthal-dimethyl; chlorthiamid; chlortoluron, cinidon(-ethyl and -methyl); cinmethylin; cinosulfuron; clefoxydim; clethodim; clodinafop and its ester derivatives (for example clodinafop-propargyl); clomazone; clomeprop; cloproxydim; clopyralid; clopyrasulfuron(-methyl); cloransulam(-methyl); cumyluron (JC 940); cyanazine; cycloate; cyclosulfamuron (AC 104); cycloxydim; cycluron; cyhalofop and its ester derivatives (for example cyhalofop-butyl, DEH-112); cyperquat; cyprazine; cyprazole; daimuron; 2,4-D; 2,4-DB; dalapon; desmedipham; desmetryn; di-allate; dicamba; dichlobenil; dichlorprop; diclofop and its esters such as diclofop-methyl; diclosulam, diethatyl(-ethyl); difenoxuron; difenzoquat; diflufenican; diflufenzopyr; dimefuron; dimepiperate; dimethachlor; dimethametryn; dimethenamid (SAN-582H); dimethazone, dimexyflam, dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron(-methyl); ethidimuron; ethiozin; ethofumesate; ethoxyfen and its esters (for example the ethyl ester, HN-252); ethoxysulfuron; etobenzanid (HW 52); F5231, i.e. N-[2-chloro-4-fluoro-5-[4-(3-fluoropropyl)-4,5-dihydro-5-oxo-1H-tetrazol-1-yl]-phenyl]ethanesulfonamide; fenoprop; fenoxan, fenoxaprop and fenoxaprop-P and their esters, for example fenoxaprop-P-ethyl and fenoxaprop-ethyl; fenoxydim; fentrazamide; fenuron; flamprop(-methyl or -isopropyl or -isopropyl-L); flazasulfuron; floazulate, florasulam; fluazifop and fluazifop-P and their esters for example fluazifop-butyl and fluazifop-P-butyl; flucarbazone(-sodium); fluchloralin; flumetsulam; flumeturon; flumiclorac(-pentyl); flumioxazin (S482); flumipropyn; fluometuron; fluorochloridone, fluorodifen; fluoroglycofen(-ethyl); flupoxam (KNW-739); flupropacil (UBIC4243); flupyrsulfuron(-methyl, or -sodium); flurenol (-butyl); fluridone; fluorochloridone; fluoroxypyr(-meptyl); flurprimidol, flurtamone; fluthiacet(-methyl); fluthiamide; fomesafen; foramsulfuron; fosamine; furyloxyfen; glufosinate(-ammonium); glyphosate (-isopropylammonium); halosafen; halosulfuron(-methyl) and its esters (for example the methyl ester, NC-319); haloxyfop and its esters; haloxyfop-P (=R-haloxyfop) and its esters; hexazinone; imazamethabenz(-methyl); imazapyr; imazaquin and salts such as the ammonium salt; imazamethapyr; imazamox; imazapic imazethamethapyr; imazethapyr, imazosulfuron; indanofan; ioxynil; isocarbamid; isopropalin; isoproturon; isouron; isoxaben; isoxachlortole; isoxaflutole; isoxapyrifop; karbutilate; lactofen; lenacil; linuron; MCPA; MCPB; mecoprop; mefenacet; mefluidid; mesosulfuron, mesotrione; metamitron; metazachlor; methabenzthiazuron; metham; methazole; methoxyphenone; methyldymron; metabenzuron, methobenzuron; metobromuron; (alpha-)metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazone; oxasulfuron; oxaziclomefone; oxyfluorfen; paraquat; pebulate; pelargonic acid; pendimethalin; pentoxazone; perfluidone; phenisopham; phenmedipham; picloram; picolinafen; piperophos; piributicarb; pirifenop-butyl; pretilachlor; primisulfuron(-methyl); procarbazone(-sodium); procyazine; prodiamine; profluralin; proglinazine(-ethyl); prometon; prometryn; propachlor; propanil; propaquizafop and its esters; propazine; propham; propisochlor; propyzamide; prosulfalin; prosulfocarb; prosulfuron (CGA-152005); prynachlor; pyraflufen(-ethyl); pyrazolinate; pyrazon; pyrazosulfuron(-ethyl); pyrazoxyfen; pyribenzoxim; pyributicarb; pyridafol; pyridate; pyrimidobac (-methyl); pyrithiobac(-sodium) (KIH-2031); pyroxofop and its esters (for example propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and methyl ester; sulcotrione; sulfentrazone (FMC-97285, F6285); sulfazurone; sulfometuron-(-methyl); sulfosate (ICI-A0224); sulfosulfuron; TCA; tebutam (GCP-5544); tebuthiuron; tepraloxydim; terbacil; terbucarb; terbuchlor; terbumeton; terbuthylazine; terbutryn; TFH 450, i.e. N,N-diethyl-3-[((2-ethyl-6-methylphenyl)sulfonyl]-1H-1,2,4-triazole-1-carboxamide; thenylchlor (NSK-850); thiafluamide; thiazafluoron; thiazopyr (Mon-13200); thidiazimin (SN-24085); thifensulfuron (-methyl); thiobencarb; tiocarbazil; tralkoxydim; tri-allate; triasulfuron; triaziflam; triazofenamide; tribenuron(-methyl); triclopyr; tridiphane; trietazine; trifluralin; triflusulfuron and esters (e.g. the methyl estser, DPX66037); trimeturon; tritosulfuron; tsitodef; vernolate; WL 110547, i.e. 5-phenoxy-1-[3-(trifluoromethyl)phenyl]-1H-tetrazole;

BAY MKH 6561, UBH-509; D-489; LS 82-556; KPP-300; NC-324; NC-330; KH-218; DPX-N8189; SC-0774; DOWCO-535; DK-8910; V-53482; PP600; MBH-001; KIH-9201; ET-751; KIH6127 and KIH-2023.

Of particular interest is the selective control of harmful plants in crops of useful and ornamental plants. Although the compounds (I) according to the invention have very good to satisfactory selectivity in a large number of crops, it is possible in principle that phytoxicity in the crop plants can occur in some crops and, in particular, when the compounds (I) are mixed with other herbicides which are less selective. In this respect, the combinations of the compounds (I) according to the invention which contain the compounds (I), or their combinations with other herbicides or pesticides, and safeners are of particular interest. The safeners, which are employed in such amounts that they act as antidotes, reduce the phytotoxic side effects of the herbicides/pesticides used, for example in economically important crops such as cereals (wheat, barley, rye, maize, rice, millet), sugar beet, sugar cane, seed rape, cotton and soya, preferably cereal. Suitable safeners for the compounds (I) and their combinations with other pesticides are, for example, the following groups of compounds:

a) Compounds of the type of dichlorophenylpyrazoline-3-carboxylic acid, preferably compounds such as ethyl 1-(2,4-dichlorophenyl)-5-(ethoxycarbonyl)-5-methyl-2-pyrazoline-3-carboxylate (S1-1) ("mefenpyr-diethyl", PM, pp. 781-782), and related compounds, as described in WO 91/07874, b) Derivatives of dichlorophenylpyrazole carboxylic acid, preferably compounds such as ethyl 1-(2,4-dichlorophenyl)-5-methylpyrazole-3-carboxylate (S1-2), ethyl 1-(2,4-dichlorophenyl)-5-isopropyl-pyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds as described in EP-A-333 131 and EP-A-269 806.

c) Compounds of the type of the triazolecarboxylic acids, preferably compounds such as fenchlorazole(ethyl ester), i.e. ethyl 1-(2,4-dichlorophenyl)-5-trichloromethyl-(1H)-1,2,4-triazole-3-carboxylate (S14) and related compounds as described in EP-A-174 562 and EP-A-346 620.

d) Compounds of the type of the 5-benzyl- or 5-phenyl-2-isoxazoline-3-carboxylic acid, or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazoline-carboxylate (S1-9) ("isoxadifen-ethyl") or its -n-propyl ester (S1-10) or ethyl 5-(4-fluorophenyl)-5-phenyl-2-isoxazoline-3-carboxylate (S1-11), as described in the German patent application (WO-A-95/07897).

e) Compounds of the type of the 8-quinolineoxyacetic acid (S2), preferably
1-methylhex-1-yl (5-chloro-8-quinolineoxy)acetate (common name "cloquintocet-mexyl" (S2-1) (see PM, pp. 263-264) 1,3-dimethylbut-1-yl (5-chloro-8-quinolineoxy)acetate (S2-2), 4-allyloxybutyl (5-chloro-8-quinolineoxy)acetate (S2-3), 1-allyloxyprop-2-yl (5-chloro-8-quinolineoxy)acetate (S2-4), ethyl (5-chloro-8-quinolineoxy)acetate (S2-5), methyl (5-chloro-8-quinolineoxy)acetate (S2-6), allyl (5-chloro-8-quinolineoxy)acetate (S2-7), 2-(2-propylideneiminoxy)-1-ethyl (5-chloro-8-quinolineoxy)acetate (S2-8), 2-oxoprop-1-yl (5-chloro-8-quinolineoxy)acetate (S2-9) and related compounds, as described in EP-A-86 750, EP-A-94 349 and EP-A-191 736 or EP-A-0 492 366.

f) Compounds of the type of the (5-chloro-8-quinolineoxy)malonic acid, preferably compounds such as diethyl (5-chloro-8-quinolineoxy)-malonate, diallyl (5-chloro-8-quinolineoxy)malonate, methyl ethyl (5-chloro-8-quinolineoxy)malonate and related compounds, as described in EP-A-0 582 198.

g) Active compounds of the type of the phenoxyacetic or -propionic acid derivatives or the aromatic carboxylic acids, such as, for example, 2,4-dichlorophenoxyacetic acid (esters) (2,4-D), 4-chloro-2-methyl-phenoxypropionic esters (Mecoprop), MCPA or 3,6-dichloro-2-methoxybenzoic acid (esters) (Dicamba).

h) Active compounds of the type of the pyrimidines, which are used as soil-acting safeners in rice, such as, for example, "fenclorim" (PM, pp. 512-511) (=4,6-dichloro-2-phenylpyrimidine), which is known as safener for pretilachlor in sown rice, i) Active compounds of the type of the dichloroacetamides, which are frequently used as pre-emergent safeners (soil-acting safeners), such as, for example,
"dichlormid" (PM, pp. 363-364) (=N,N-diallyl-2,2-dichloroacetamide), "R-29148" (=3-dichloroacetyl-2,2,5-trimethyl-1,3-oxazolidine from Stauffer),
"benoxacor" (PM, pp. 102-103) (=4-dichloroacetyl-3,4-dihydro-3-methyl-2H-1,4-benzoxazine),
"PPG-1292" (=N-allyl-N-[(1,3-dioxolan-2-yl)methyl] dichloroacet-amide from PPG Industries),
"DK-24" (=N-allyl-N—[(allylaminocarbonyl)methyl] dichloroacetamide from Sagro-Chem),
"AD-67" or "MON 4660" (=3-dichloroacetyl-1-oxa-3-aza-spiro[4,5]-decane from Nitrokemia or Monsanto),
"diclonon" or "BAS145138" or "LAB145138" (=3-dichloroacetyl-2,5,5-trimethyl-1,3-diazabicyclo [4.3.0]nonane from BASF) and "furilazol" or "MON 13900" (see PM, 637-638) (=(RS)-3-dichloroacetyl-5-(2-furyl)-2,2-dimethyloxazolidine)

j) Active compounds of the type of the dichloroacetone derivatives, such as, for example,
"MG 191" (CAS-Reg. No. 96420-72-3) (=2-dichloromethyl-2-methyl-1,3-dioxolane from Nitrokemia), which is known as safener for maize, k) Active compounds of the type of the oxyimino compounds, which are known as seed dressings, such as, for example,
"oxabetrinil" (PM, pp. 902-903) (=(Z)-1,3-dioxolan-2-ylmethoxy-imino(phenyl)acetonitrile), which is known as seed dressing safener for millet against metolachlor damage,
"fluxofenim" (PM, pp. 613-614) (=1-(4-chlorophenyl)-2,2,2-trifluoro-1-ethanone O-(1,3-dioxolan-2-ylmethyl) oxime), which is known as seed dressing safener for millet against metolachlor damage, and "cyometrinil" or "-CGA-43089" (PM, p. 1304) (=(Z)-cyanomethoxy-imino(phenyl)acetonitrile), which is known as seed dressing safener for millet against metolachlor damage, l) Active compounds of the type of the thiazolecarboxylic esters, which are known as seed dressings, such as, for example, "flurazol" (PM, pp. 590-591) (=benzyl 2-chloro-4-trifluoromethyl-1,3-thiazole-5-carboxylate), which is known as seed dressing safener for millet against alachlor and metolachlor damage, m) Active compounds of the type of the naphthalenedicarboxylic acid derivatives, which are known as seed dressings, such as, for example, "naphthalic anhydride" (PM, p. 1342) (=1,8-naphthalenedicarboxylic anhydride), which is known as seed dressing safener for maize against thiocarbamate herbicide damage, n) Active compounds of the type of the chromanacetic acid derivatives, such as, for example, "CL 304415" (CAS-Reg. No. 31541-57-8) (=2-(4-carboxychroman-4-yl)acetic acid from American Cyanamid), which is known as safener for maize against imidazolinone damage, o) Active compounds which, in addition to a herbicidal action against harmful plants, also have safener action in crop plants such as rice, such as, for example, "dimepiperate" or "MY-93" (PM, pp. 404-405) (=S-1-methyl-1-phenylethyl piperidine-1-thiocarboxylate), which is known as safener for rice against herbicide molinate damage, "daimuron" or "SK 23" (PM, p. 330) (=1-(1-methyl-1-phenylethyl)-3-p-tolylurea), which is known as safener for rice against herbicide imazosulfuron damage, "cumyluron"="JC-940" (=3-(2-chlorophenylmethyl)-1-(1-methyl-1-phenylethyl)urea, see JP-A-60087254), which is known as safener for rice against damage by some herbicides, "methoxyphenon" or "NK 049" (=3,3'-dimethyl-4-methoxy-benzophenone), which is known as safener for rice against damage by some herbicides, "CSB" (=1-bromo-4-(chloromethylsulfonyl)benzene) (CAS-Reg. No. 54091-064 from Kumiai), which is known as safener against damage by some herbicides in rice p) N-Acylsulfonamides of the formula (S3) and salts thereof,

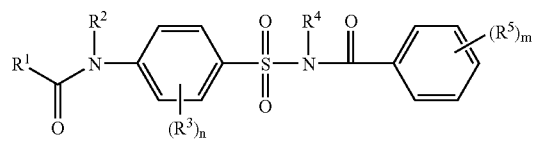

(S3)

as described in WO-A-97/45016, q) Acylsulfamoylbenzoamides of the formula (S4), if appropriate also in salt form,

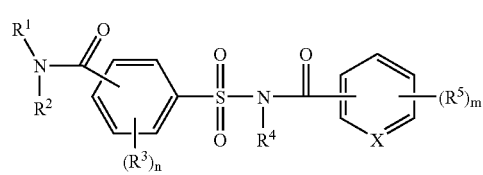

(S4)

as described in the International Application No. PCT/EP98106097, and r) compounds of the formula (S5),

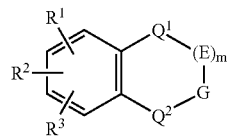

(S5)

as described in WO-A 98/13 361, including the stereoisomers and the salts used in agriculture.

Among the safeners mentioned, (S1-1) and (S1-9) and (S2-1), in particular (S1-1) and (S1-9), are of particular interest.

Some of the safeners are already known as herbicides and consequently show, in addition to the herbicidal action against harmful plants, also protective action in connection with crop plants.

The ratios by weight of herbicide (mixture) to safener generally depend on the application rate of the herbicide and the efficacy of the safener in question and can vary within wide limits, for example in the range from 200:1 to 1:200, preferably 100:1 to 1:100, in particular 20:1 to 1:20. Analogously to the compounds (I) or their mixtures, the safeners can be formulated with other herbicides/pesticides and be provided and used as ready mix or tank mix with the herbicides.

For use, the herbicide or herbicide/safener formulations which are present in commercially available form are, if appropriate, diluted in the customary manner, for example using water in the case of wettable powders, emulsifiable concentrates, dispersions and water-dispersible granules. Preparations in the form of dusts, granules for soil application or broadcasting and sprayable solutions are usually not further diluted with other inert substances prior to use.

The required application rate of the compounds (I) varies with the external conditions, such as temperature, humidity, the nature of the herbicide used and the like. It can vary within wide limits, for example between 0.0005 and 10.0 kg/ha or more of active substance, preferably between 0.001 and 3 kg/ha, in particular from 0.005 to 1 kg/ha.

In addition, the compounds according to the invention also have useful pharmaceutical activity. It is known that adenosine and adneosine monophosphate (AMP) are formed in disorders of the type circulatory disorders or oxygen deficits (ischemia) by degradation of adenosine triphosphate in the ischemic tissues. The further metabolism of AMP by AMPDA to inosine monophosphate or of adenosine by adenosine deaminase (ADA) to inosine leads to a reduced adenosine concentration in the tissue, which is thought to be the cause of other syndromes (cf., for example, WO-A-94/18200 and literature cited therein). Thus, inhibitors of AMPDA or ADA can contribute in reducing excess degradation of adenosine, thus protecting the tissue against damage.

The AMPDA inhibitors according to the invention can be employed for treating a broad range of clinical symptoms in which local elevation of the adenosine concentration in the tissue is helpful. They are, for example, suitable for treating cardiovascular disturbances, for example myocardial infarct, angina pectoris and other cardiovascular disorders. Furthermore, they can be used as analgesics for treating acute or permanent pain caused by arthritis, cancer, neuralgia, multiple sclerosis and general neuropathies.

Moreover, the inhibitors are suitable for treating infections, for example those caused by protozoa or worms.

Use is also appropriate in combination with therapies relating to the metabolism of purines and/or pyrimidines. Such therapies include treatment with antiviral agents, such as acyclovir, azidothymidine, dideoxyinosine, adenosinearabinoside, dideoxyadenosine and ribovirin or agents for treating cancer, such as 5-fluoruracil, azathiopyrine, dacarbazine, cytosinearabinoside, methotrexate, brendinine, tiazafurin, 2'-deoxy-coformycin and 2'-deoxy-2-chloroadenosine.

A further area of indication is the treatment of Alzheimer diseases which are associated with a pathologically increased AMPDA concentration; cf. B. Sims et al., Neurobiol. Aging, 9 (1998) 385.

The directly or indirectly acting inhibitors can be used in a wide dose and concentration range.

If the compounds (I) are salts of compounds of the formula (I), physiologically or toxicologically acceptable salts are particularly suitable for use as pharmaceuticals. Salts suitable for pharmaceutical use which are derived from compounds of the formula (I) having acidic groups are, for example, alkali metal salts, such as sodium salts or potassium salts, alkaline earth metal salts, such as calcium salts or magnesium salts, or ammonium salts based on ammonia or organic amines, such as, for example, ethylamine, ethanolamine, triethanolamine or amino acids. Salts suitable for pharmaceutical use which are derived from compounds of the formula (I) having basic (protonatable) groups are, for example, acid addition salts with physiologically acceptable inorganic or organic acids, such as salts with hydrogen chloride, hydrogen bromide, phopshoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc.

If the compounds of the formula (I) simultaneously contain acidic and basic groups in the molecule, the invention also includes internal salts or betaines (zwitterions), in addition to the salt forms described. The salts can be obtained from the compounds of the formula (I) according to the processes already mentioned above. Physiologically acceptable salts of compounds of the formula (I) are understood as meaning, for example, their organic and inorganic salts, as described in Remington's Pharmaceutical Sciences (17th edition, page 1418 (1985)). Owing to the physical and chemical stability and the solubility, sodium, potassium, calcium and ammonium salts, inter alia, are preferred for acidic groups; for basic groups, preference is given, inter alia, to salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid.

The compounds (I) can be used on animals, preferably on mammals, and in particular on humans as pharmaceuticals per se, as mixtures with one another or in the form of pharmaceutical preparations. The present invention also provides the compounds (I) for use as pharmaceuticals, their use in the therapy and prophylaxis of the syndromes mentioned and their use for the preparation of pharmaceuticals therefor. The present invention furthermore provides pharmaceutical preparations which, as active constituent, contain an effective dose of at least one compound (I), in addition to customary, pharmaceutically innocuous excipients and auxiliaries. The pharmaceutical preparations usually comprise 0.1 to 99 percent by weight, preferably 0.5 to 95 percent by weight, of the compounds (I). The production of the pharmaceutical preparations can be carried out in a manner known per se. To this end, the compounds (I) are brought, together with one or more solid or liquid pharmaceutical excipients and/or auxiliaries and, if desired, in combination with other pharmaceutically active compounds, into a suitable administration form or dose form, which can then be used as a pharmaceutical in human medicine or veterinary medicine.

Pharmaceuticals which comprise a compound (I) can be administered orally, parenterally, intravenously, rectally or by inhalation, the preferred administration being dependent on the particular symptoms of the disorder. The compounds (I) can be used on their own or together with pharmaceutical auxiliaries, both in veterinary and in human medicine.

The person skilled in the art is familiar on the basis of his expert knowledge with the auxiliaries which are suitable for the desired pharmaceutical formulation. In addition to solvents, gel-forming agents, suppository bases, tablet auxiliaries and other active compound excipients, it is possible to use, for example, antioxidants, dispersants, emulsifiers, antifoams, flavor corrigents, preservatives, solubilizers or colorants.

For an oral administration form, the active compounds are mixed with the additives suitable therefor, such as excipients, stabilizers or inert diluents, and brought by the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, glucose or starch, in particular corn starch. The preparation can take place here both as dry and as moist granules. Suitable oily excipients or solvents are, for example, vegetable or animal oils, such as sunflower oil or cod liver oil.

For subcutaneous or intravenous administration, the active compounds are brought into solution, suspension or emulsion, if desired with the substances customary for this purpose, such as solubilizers, emulsifiers or other auxiliaries. Suitable solvents are, for example: water, physiological saline solution or alcohols, for example ethanol, propanol, glycerol, and in addition also sugar solutions, such as glucose or mannitol solutions, or alternatively mixtures of the various solvents mentioned.

Suitable pharmaceutical formulations for administration in the form of aerosols or sprays are, for example, solutions, suspensions or emulsions of the active compound (I) in a pharmaceutically acceptable solvent such as, in particular, ethanol or water, or in a mixture of such solvents.

If required, the formulation can also contain other pharmaceutical auxiliaries such as surfactants, emulsifiers and stabilizers, and also a propellant. Such a preparation usually contains the active compound in a concentration of approximately 0.1 to 10, in particular of approximately 0.3 to 3% by weight.

The dosage of the active compound (I) to be administered and the frequency of administration depends on the potency and duration of action of the compounds used; and furthermore also on the nature and severity of the disease to be treated and on the sex, age, weight and individual responsiveness of the mammal to be treated.

On average, the daily dose of a compound (I) in the case of a patient weighing about 75 kg is preferably 0.001 mg/kg to 50 mg/kg, in particular 0.01 to 10 mg/kg, of body weight. In particular when treating acute cases of the disease, for example immediately after a myocardial infarct, even higher and especially more frequent dosages may be required, for example up to 4 individual doses per day. In particular in the case of i.v. administration, for example for an infarct patient in an intensive care unit, up to 200 mg per day may be required.

Acute treatment of coronary occlusion can be carried out, for example, by infusion of a sterile aqueous solution of the active compound or a solution of the active compound in isotonic saline solution into the carotid or into the coronary arteries if an intracardiac catheter has been applied. In infusions, the rate of administration is, for example, in the range from 1 to 20 nmol of active compound/min/kg, with an infusion volume of 30 ml/h over a plurality of days.

In the examples below, amounts (including percentages) are based on weight, unless specifically stated otherwise.

A. CHEMICAL EXAMPLES

Frequently used abbreviations in the text, in schemes and tables:

| | |
|---|---|
| Ac = | $COCH_3$ = acetyl |
| Bu = | butyl |
| t-Bu = | tertiary butyl |
| Bz = | benzoyl = —CO—$C_6H_5$ |
| Et = | ethyl |
| Me = | methyl |
| Ph = | phenyl |
| Pr = | propyl |
| i-Pr = | isopropyl |
| c-Pr = | cyclopropyl |
| DCC = | dicyclohexylcarbodiimide |
| DCM = | dichloromethane |
| DMAP = | dimethylaminopyridine |
| DMF = | dimethylformamide |
| NBA = | nitrobenzyl alcohol |
| THF = | tetrahydrofuran |
| FAB = | "fast atom bombardment" (ionization technique for mass spectrum) |

Example 1

7-Chloro-3-(2',3',5-tri-O-acetyl-β-D-ribofuranosyl)-1H-pyrazolo[4,3-d]-pyrimidine (II-1)

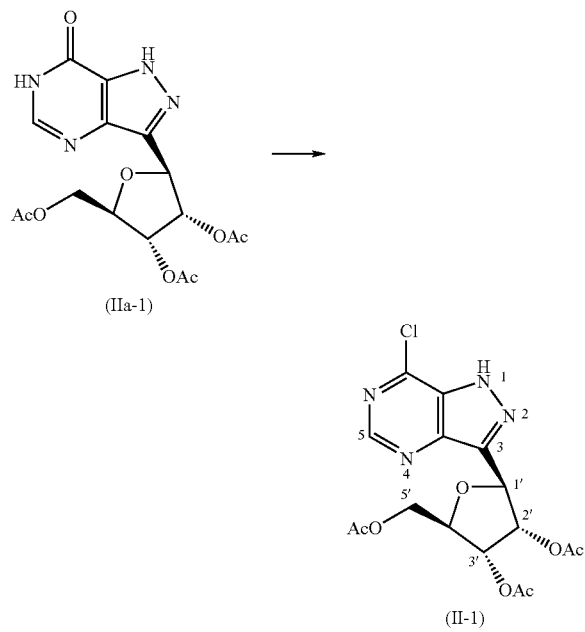

A mixture of the keto compound (IIa-1) (J. Chem. Soc. (C), 1971, 2443) (210 mg, 0.52 mmol) and $POCl_3$ (3 ml) was slowly heated to reflux temperature and kept at this temperature for 30 min. After cooling to room temperature, the solvent was removed under reduced pressure and an ice/water mixture (2 ml) was added to the residue. The mixture was extracted with ethyl acetate (3×2 ml), the extract was dried over $MgSO_4$ and the solvent was removed under reduced pressure, giving a residue which, after chromatography over silica gel (mobile phase 5-10% ethyl acetate in petroleum ether), was obtained as a colorless foam. Yield: 130 mg, 60%;

IR spectrum: $v_{max}$ (NaCl/film/cm$^{-1}$) 3235 bw (NH), 3073w, 1747s (C═O, ester), 1607w, 1540s, 1475w, 1447w, 1375s, 1240s, 1173w, 1146w, 1094s, 1049s, 936s, 918s, 866w, 817w, 733s; $^1$H-NMR: 5H (270 MHz, CDCl$_3$) 8.86 (1H, s, H-5), 5.98 (1H, t, J=5.5 Hz, H-2'), 5.70 (1H, t, J=5.4 Hz, H-3'), 5.57 (1H, d, J=5.6 Hz, H-1), 4.53-4.48 (1H, m, H-5a'), 4.47-4.42 (1H, m, H4'), 4.33-4.28 (1H, m, H-5b'), 2.15 (3H, s, CH$_3$), 2.09 (3H, s, CH$_3$), 2.08 (3H, CH$_3$)

Mass spectrum (FAB, NBA): found MH$^+$, 413.0867, calculated $C_{16}H_{18}ClN_4O_7$, MH, 413.0864

Example 2

3-(2',3',5'-Tri-O-acetyl-β-D-ribofuranosyl)-1H-pyrazolo[4,3-d]pyrimidine (Ia)

Method A

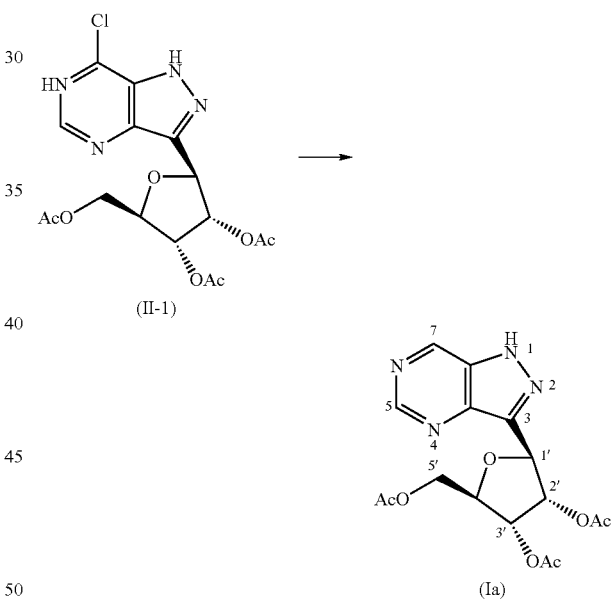

A solution of the chloride (II-1) (72 mg, 0.18 mmol) in dry ethyl acetate was admixed with 5% Pd/C (20 mg) and MgO (18 mg, 0.45 mmol) and, with stirring, covered with hydrogen gas. After the starting material (II-1) had been converted, the mixture was filtered through a short Celite column, eluted with ethyl acetate, the solvent was removed under reduced pressure and the residue was chromatographed over silica gel (mobile phase 3-5% ethyl acetate in petroleum ether). Yield of (Ia): 46 mg, 70% of theory, as a colorless foam.

IR spectrum: $v_{max}$ (NaCl/film)/cm$^{-1}$ 3307 (NH), 3078w, 3035w, 1747s, (C═O, ester), 1660w, 1644w, 1602w, 1557w, 1479w, 1435w, 1376s, 1240s, 1089s, 1049s, 917w, 778w, 733w; NMR spectrum: δ$_H$ (270 MHz, CDCl$_3$): 12.10

(1H, bs, NH), 9.20 (1H, s, H-7), 9.09 (1H, s, H-5), 6.00 (1H, t, J=5.3 Hz, H-2'), 5.70 (1H, t, J=5.5 Hz, H-3'), 5.60 (1H, d, J=5.5 Hz, H-1'), 4.47-4.53 (1H, m, H-5a'), 4.42-4.45 (1H, m, H-4'), 4.24-4.30 (1H, m, H-5b'), 2.13 (3H, s. $CH_3$), 2.07 (3H, s, $CH_3$), 2.03 (3H, s $CH_3$);

Mass spectrum (FAB, NBA): found $MH^+$, 379.1267, calculated: $C_{16}H_{19}N_4O_7$, MH, 379.1254

Method B

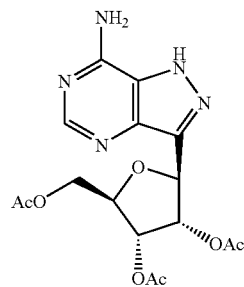
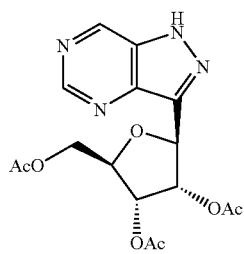

(Ia)

A mixture of 2',3',5'-tri-O-acetyl-formycin A (prepared from formycin A by modification of the method from Synthesis (1989) 401) (1.1 g, 2.8 mmol) and n-butyl nitrite (2.6 ml, 22 mmol) in THF (30 ml) was heated at 50° C. for 25 h. After cooling to room temperature, the solvent was removed under reduced pressure. The mixture was dissolved in EtOH and reconcentrated (in each case twice). Silica gel chromatography using 2% MeOH in DCM gave compound (Ia) (0.49 g, 46%), the analysis of which confirmed the chemical identity with the product from method A.

Example 3

3-β-D-Ribofuranosyl-1H-pyrazolo[4,3-d]pyrimidine (Ib)

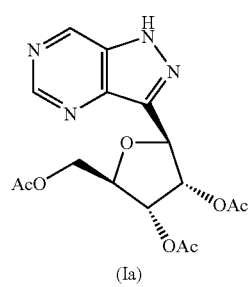

(Ia)

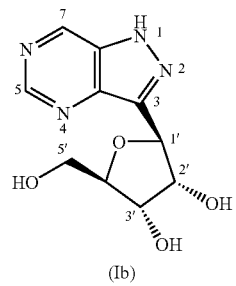

(Ib)

A solution of the triacetate (Ia) (46 mg, 0.12 mmol) in $EtOH/NH_3$ (4 ml, saturated at 0° C.) was stirred at room temperature for 4 days. Concentration and silica gel chromatography (gradient elution using 5 to 10% methanol in DCM) gave the title compound (Ib) as colorless crystals (yield: 30 mg, 98% of theory), melting point 227-228° C. from ethanol; IR spectrum: $v_{max}$ (NaCl/nujol/$cm^{-1}$) 3380bw, 3325bw, 3115bw (NH and OH), 1695w, 1617w, 1551w, 1532w, 1287w, 1266w, 1244w, 1242w, 1125w, 1112w, 1099s, 1049s, 1026s, 984w, 930s, 868w, 826w, 795w;

NMR spectrum: $\delta_H$ (270 MHz, DMSO-$d_6$+$D_2O$) 9.34 (1H, s, H-7), 9.01 (1H, s, H-5), 5.08 (1H, d, J=7.1 Hz, H-1'), 4.58 (1H, dd, J 7.0, 5.3 Hz, H-2'), 4.13 (1H, dd, J 5.0, 3.7 Hz, H-3'), 3.95 (1H, q, J=3.7 Hz, H-4'), 3.65 (1H, AB, J 12.2, 4.1 Hz, H-5a'), 3.52 (1H, AB, J 12.0, 4.4 Hz, H-5b'); mass spectrum: (FAB, NBA): found $MH^+$ 253.0941. Calculated: $C_{10}H_{13}N_4O_4$MH, 253.0937.

Example 4

3-(5'-O-Phosphoryl-β-D-ribofuranosyl)pyrazolo[4,3-d]pyrimidine disodium salt (Ic)

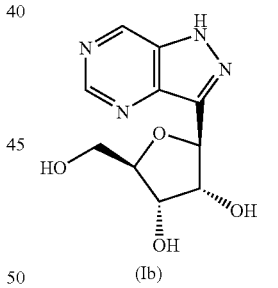

(Ib)

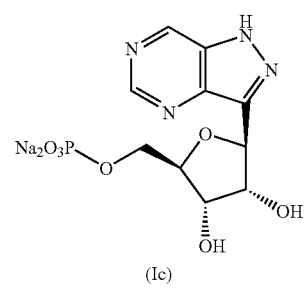

(Ic)

At 0° C., $POCl_3$ (60 μl, 0.66 mmol) was added dropwise under $N_2$ gas to a suspension of deaminoformycin A (15 mg, 0.06 mmol) (Ib) in dry triethyl phosphate (1.5 ml). After 1.5 h, the reaction mixture had formed a clear solution; after 15 h, ice-water (5 ml) was added and the mixture was extracted with DCM and neutralized using saturated sodium bicarbonate solution. Chromatography of the solution over a "reverse-phase" column (elution with water) and removal of the solvent under reduced pressure gave the title product (Ic) as a white solid with a melting point of more than 220° C.;

Mass spectrum (electron spray, positive ions) 377 (MH$^+$).

IR spectrum: $v_{max}$ [cm$^{-1}$] ("Golden-Gate" method) 3370 (bw), 3230 (bw), 1677 (s), 1201 (s), 1110 (s), 975 (m).

$^1$H-NMR (D$_2$O, 270 MHz): δ [ppm]=9.30 (s, 1H, H-7), 8.95 (s, 1H, H-5); 5.36 (d, 1H, J=7.5 Hz, H-1'), 4.76 (m, 1H, H-2'), 4.38 (t, 1H, J=5 Hz, H-3'), 4.12 (q, 1H, J=5 Hz, H-4'), 3.91 (m, 2H, H-5').

Example 5

6,8-Di(methylthio)-3-(5'-O-tert-butyldiphenylsilyl-2',3'-O-isopropylidene-β-ribofuranosyl)imidazo[2,1-f]-1,2,4-triazine (IIIa)

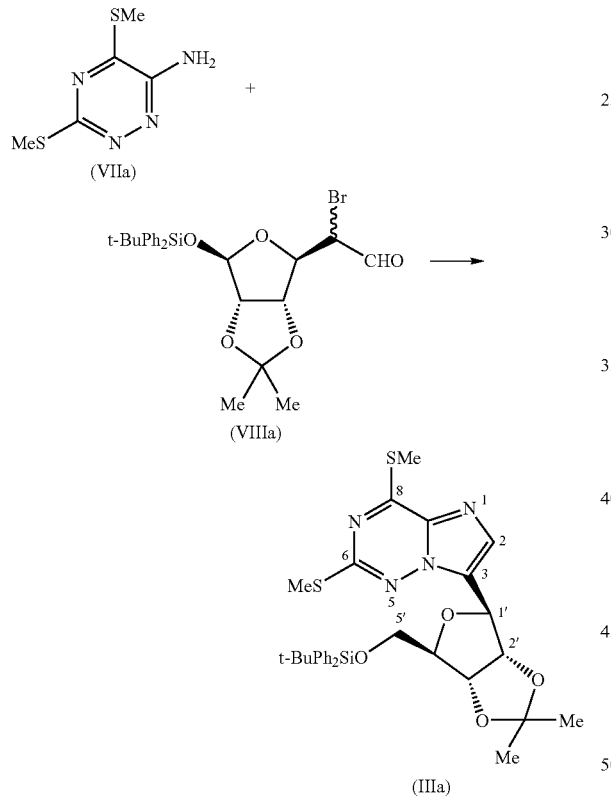

Method A

A mixture of the bromoaldehyde (VIIIa) (prepared by the method of J. Org. Chem. 48 (1983) 3141, but with the Si-containing protective group) (664 mg, 1.25 mmol), the amine (VIIa) (see J. Org. Chem. 48 (1983) 1271) (234 mg, 1.25 mmol) and anhydrous potassium carbonate (208 mg, 1.50 mol) in dry toluene (80 ml) was heated at reflux, and the water formed was removed azeotropically. After 24 h, the mixture was allowed to cool to room temperature, and the solvent was removed under reduced pressure. Silica gel chromatography using 10 to 15% ether in petroleum ether gave 434 mg, 56%.

IR spectrum: $v_{max}$ (NaCl/film/cm$^{-1}$) 3071w, 1694w, 1631w, 1574w, 1516w, 1441s, 1372w, 1352w, 1214w, 1154s, 1114s. $^1$H-NMR spectrum: δ$_H$ (270 MHz, CDCl$_3$) 7.63-7.69 (4H, m, Ar H), 7.60 (1H, s, H-2), 7.32-7.43 (6H, m, Ar H), 5.39 (1H, d, J=4.9 Hz, H-1'), 4.97 (1H, dd, J 6.6, 4.8 Hz, H-2'), 4.82 (1H, dd, J 6.5, 3.7 Hz, H-3"), 4.24-4.27 (1H, m H4'), 3.84-3.86 (2H, m, H-5'), 2.67 (3H, s, SCH$_3$), 2.52 (3H, s, SCH$_3$), 1.37 (3H, s, CH$_3$), 1.37 (3H, s, CH$_3$), 1.05 (9H, s, tert-bu); mass spectrum: found MH$^+$, 623.2182, C$_{31}$H$_{39}$N$_4$O$_4$S$_2$Si calculated MH, 623.2111

Method B

A solution of the aldehyde (VIIIa) (3.40 g, 6.38 mmol) in dry toluene was added to a solution of the amine (VIIa) (1.20 g, 6.38 mmol) in HMPA (6 ml), and the mixture was stirred under nitrogen gas at 100° C. for 18 hours and then cooled to 25° C. The solvent was removed under reduced pressure, the residue was then extracted three times with ethyl acetate and the combined organic phases were washed with water and sodium chloride solution, dried over MgSO$_4$ and concentrated under reduced pressure. Silica gel chromatography using 10 to 15% ether in petroleum ether gave the compound (IIIa) (2.46 g, 62% of theory); analysis as under Method A.

Example 6

8-Hydrazino-6-methylthio-3-(5-O-tert-butyldiphenylsilyl-2',3'-O-iso-propylidene-β-D-ribofuranosyl)imidazo[2,1-f]-1,2,4-triazine (IIIb)

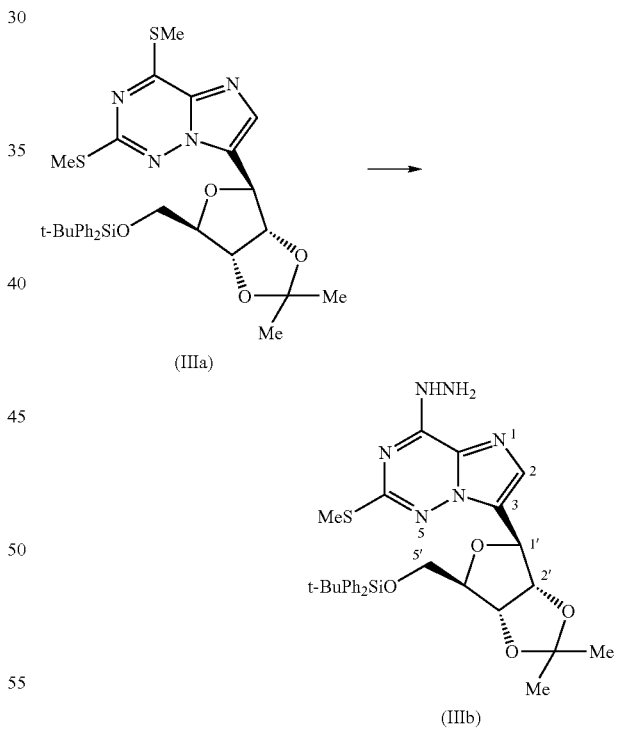

Hydrazine monohydrate (0.02 ml, 0.70 mmol) was added to a solution of the dithioether (IIIa) (50.9 mg, 0.08 mmol) in ethanol (2 ml), and the solution was, with stirring, heated under reflux for 1 hour. After cooling to room temperature, the mixture was concentrated under reduced pressure, the residue was dissolved in DCM (6 ml), the organic phase was washed with water, dried over MgSO$_4$ and concentrated under reduced pressure, and the residue was chromatographed over silica gel (ether). (Yield: 43 mg, 87%).

IR spectrum: $v_{max}$ (NaClifilm/cm$^{-1}$) 3442bs (NH), 2931w, 2858w, 1694s, 1631s, 1603s, 1443s, 1428s, 1353s, 1265s, 1113s, 1079s, 863w, 703s; $^1$H-NMR: $\delta_H$ (270 MHz, CDCl$_3$) 7.63-7.69 (4H, m, Ar H), 7.54 (1H, s, H-2), 7.31-7.40 (6H, m, Ar H), 5.35 (1H, d, J=4.85 Hz, H-1'), 5.02 (1H, dd, J 6.5, 4.8 Hz, H-2'), 4.82 (1H, dd, J 6.5, 3.7, H-3'), 4.24-425 (1H, m, H-4'), 3.84-3.86 (2H, m, H-5'), 2.48 (3H, s, SCH$_3$), 1.62 (3H, s, CH$_3$), 1.37 (3H, s CH$_3$), 1.05 (9H, s, tert-bu);

Mass spectrum (FAB, NBA): found MH$^+$, 607.2537 C$_{30}$H$_{39}$N$_6$O$_4$SSi; calculated: MH, 607.2523.

Example 7

6-Methylthiosulfanyl-3-(5'-O-tert-butyldiphenylsilyl-2',3'-O-isopropylidene-β-D-ribofuranosyl)imidazo[2,1-f]-1,2,4-triazine (IIIc)

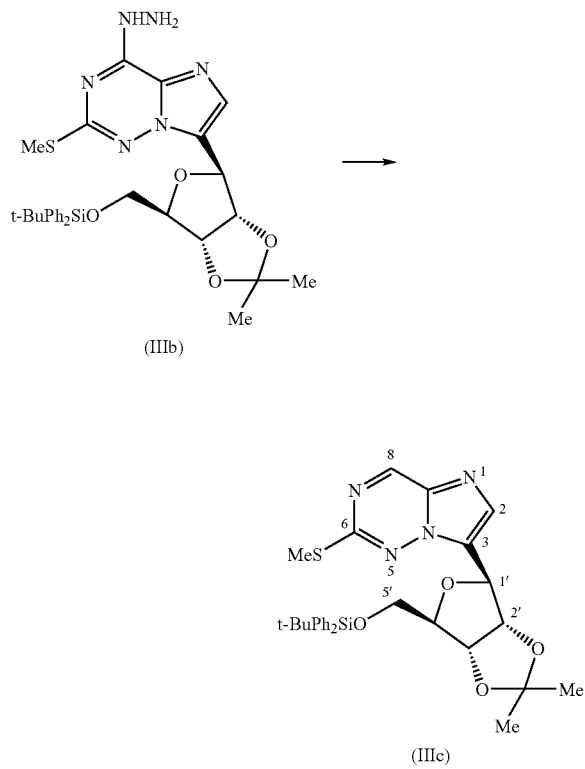

At room temperature, a solution of the hydrazine derivative (IIIb), (1.04 g, 1.72 mmol) in ethanol (60 ml) was admixed with yellow HgO (1.12 g, 5.15 mmol). The mixture was heated at reflux (2 h) and then cooled to 25° C., inorganic components were removed by filtration through Celite, the Celite was washed with ethanol and the organic phase was concentrated under reduced pressure. The resulting yellow foam was chromatographed over silica gel using 5 to 10% ether in petroleum ether, giving the title compound (712 mg, 72%) as a colorless foam;

NMR spectrum $\delta_H$ (300 MHz, CDCl$_3$) 9.00 (1H, s, H-8), 7.80 (1H, s, H-2), 7.64-7.70 (4H, m, Ar H), 7.33-7.44 (6H, m, Ar H), 5.46 (1H, d, J=5.0 Hz, H-1'), 4.98 (1H, dd, J 6.4, 5.1 Hz, H-2'), 4.86 (1H, dd, J 6.1, 3.6 Hz, H-3'), 4.30-4.31 (1H, m, HA4'), 3.87-3.89 (2H, m, H-5'), 2.56 (3H, s, SCH$_3$), 1.65 (3H, s, CH$_3$), 1.39 (3H, s, CH$_3$), 1.07 (9H, s, tert-bu); mass spectrum (FAB, NBA): found MH$^+$, 577.2321 C$_{30}$H$_{37}$N$_4$O$_4$SSi, calculated: MH, 577.2305

Example 8

6-Methylthio-3-(2',3'-O-isopropylidene-β-D-ribofuranosylimidazo[2,1-f]-1,2,4-triazine (Id)

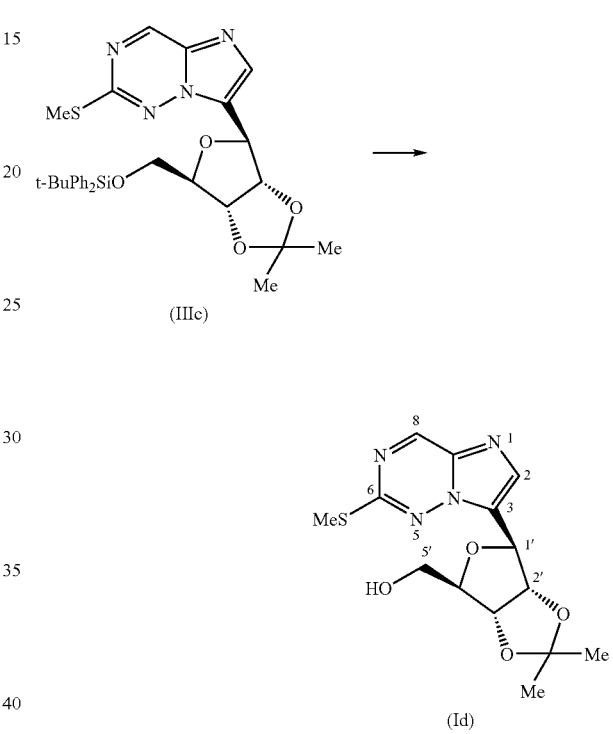

n-BU$_4$NF (TBAF, 0.73 ml, 1M in THF, 0.73 mmol) was added to the solution of the silyl ether (IIIc) (211 mg, 0.37 mmol) in dry tetrahydrofuran (THF) (12 ml), and the mixture was stirred at 25° C. for 30 min. The mixture was diluted with ether, water (20 ml) was added and the organic phase was separated off, washed with sodium chloride solution (10 ml), dried over MgSO$_4$ and concentrated under reduced pressure. Silica gel chromatography using 60 to 70% ether in petroleum ether gave the alcohol (Id) as a white solid (111 mg, 90%) of melting point 92 to 93° C. (from DCM/petroleum ether). IR spectrum: $v_{max}$ ((NaCl-film/cm$^{-1}$) 3441w (OH), 2935w, 2876w, 1694w, 1628w, 1591s, 1531s, 1471s, 1422s, 1382s, 1342s, 1304s, 1274w, 1214s, 1157w, 1122s, 1078s, 921w, 862w, 763w, 735w, 662w; $^1$H-NMR spectrum: $\delta_H$ (270 MHz, CDCl$_3$) 8.99 (1H, s, H-8), 7.82 (1H, s, H-2), 5.31 (1H, d J 5.5 Hz, H-1'), 5.16 (1H, dd, J 6.6, 5.5 Hz, H-2'), 4.96 (1H, dd, J 6.6, 3.7 Hz, H-3'), 4.25-4.27 (1H, m, H-4'), 3.89-3.90 (2H, m, H-5'), 2.91-3.22 (1H, m, OH), 2.62 (3H, s, SCH$_3$), 1.62 (3H, s, CH$_3$), 1.37 (3H, s, CH$_3$), mass spectrum (FAB, NBA): found MH$^+$, 339.1144, C$_{14}$H$_{19}$N$_4$O$_4$S, calculated: MH, 339.1127

Example 9

6-Methylthio-3-β-D-ribofuranosylimidazo[2,1-f]-1,2,4-triazine (Ie)

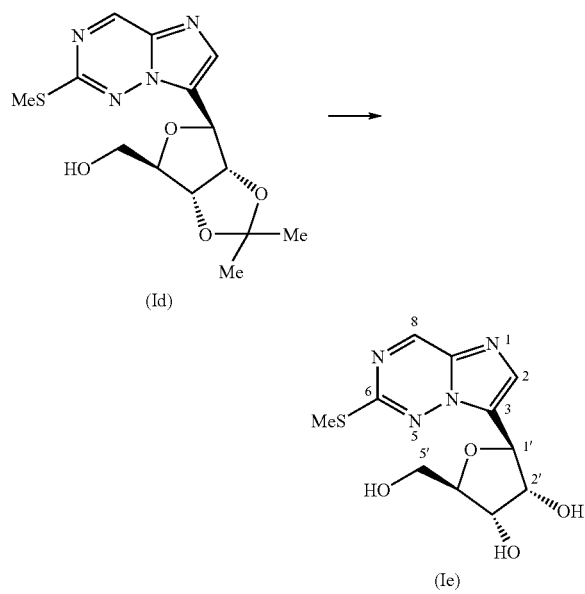

A solution of 1,3-dioxolane (Id) (50.9 mg, 0.15 mmol), glacial acetic acid (2 ml) and water (1 ml) was stirred at 25° C. for 18 hours. The solvent was then removed under reduced pressure. Recrystallization from ethanol gave (Ie) (27 mg, 60%) as white crystals; melting point (227-228° C.) (EtOH); IR spectrum: $v_{max}$ (NaCl/nujol/cm$^{-1}$) 3441 (OH), 3202 (OH), 1693w, 1630w, 1595s, 1529w, 1311s, 1225s, 1172s, 1116s, 1069w, 1040w, 985w, 957w, 931w, 774w; NMR spectrum: $\delta_H$ (270 MHz, DMSO-d$_6$+D$_2$O) 9.14 (1H, s, H-8), 7.97 (1H, s, H-2), 5.16 (1H, d, J=6.2 Hz, H-1'), 4.42 (1H, dd, J 6.0, 5.5 Hz, H-2'), 4.00-4.08 (1H, m, H-3'), 3.90-3.91 (1H, m, H-4'), 3.52-3.58 (2H, m, H-5'), 2.60 (3H, s, SCH$_3$); mass spectrum (FAB, NBA): found MH$^+$, 299.0809 C$_{11}$H$_{15}$N$_4$O$_4$S, calculated MH, 299.0814.

Example 10

6-Bromo-3-dimethylamino-1,2,4-triazine-5(4H)-one (X)

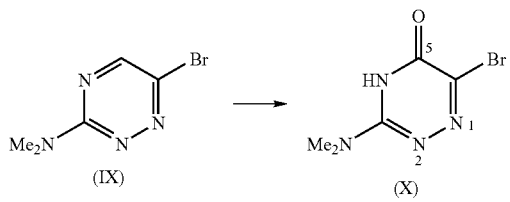

Hydrogen peroxide (27% strength solution in water, 0.53 ml, 4.56 mmol) was added at 5° C. to a solution of 6-bromo-3-dimethylamino-1,2,4-triazine (IX) (J. Org. Chem. 43 (1978) 2514) (500 mg, 2.46 mmol) in glacial acetic acid (4 ml), and the reaction mixture was stirred at 25° C. for 12 hours. The resulting precipitate was collected, washed with water, dried in the air and recrystallized from ethanol. The ketone (X) (368 mg, 68%) was obtained as white crystals of melting point 261-262° C. (ethanol).

IR spectrum: $v_{max}$ (NaCl/nujol/cm$^{-1}$) 3114w, 1608s, 1567s, 1504s, 1435s, 1403s, 1254w, 1211w, 1156w, 1133w, 1076s, 1016s, 908s, 865w, 769s 701w, 646w;

$^1$H-NMR spectrum: $\delta_H$ (270 MHz, DMSO-d$_6$), 3.72 (6H, s, NCH$_3$); mass spectrum:

found M$^+$, 220.9866. C$_5$H$_7$$^{81}$BrN$_4$O, calculated M, 220.9861;

found M$^+$, 218.9885. C$_5$H$_7$$^{79}$BrN$_4$O calculated M, 218.9881

Example 11

3-Dimethylamino-6-hydrazino-1,2,4-triazin-5(4H)-one (XI)

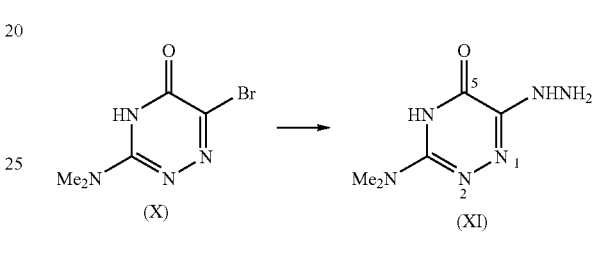

With stirring, hydrazine monohydrate (1.44 ml, 30 mmol) was added at 25° C. to a solution of the bromide (X) (2.20 g, 10 mmol) in water (80 ml). The reaction mixture was heated to reflux, cooled to room temperature and, for crystallization, allowed to stand for several hours. The crystals were filtered off, washed with water and dried in the air, giving the hydrazine (XI) (1.08 g, 63%) as a white solid of melting point 264-266° C. (from ethanol): IR spectrum $v_{max}$ (NaCl/nujol/cm$^{-1}$) 3324s, 3301s, (NH), 1641s (C=O), 1575s, 1516s, 1397s, 1304w, 1260w, 1204w, 1165w, 1133w, 1068w, 1050s, 1005w, 923s, 833w, 786s, 709s, 683s; NMR spectrum: $\delta_H$ (270 MHz, DMSO-d$_6$): 11.25 (2H, bs, NH$_2$), 7.18 (1H, bs, NH), 2.96 (6H, s, NCH$_3$);

mass spectrum: found M$^+$, 170.0933

C$_5$H$_{10}$N$_6$O, calculated M, 170.0916

Example 12

N-[(2',3',5'-Tri-O-benzoyl-β-D-ribofuranosyl)carbonyloxy]succinimide (XIII)

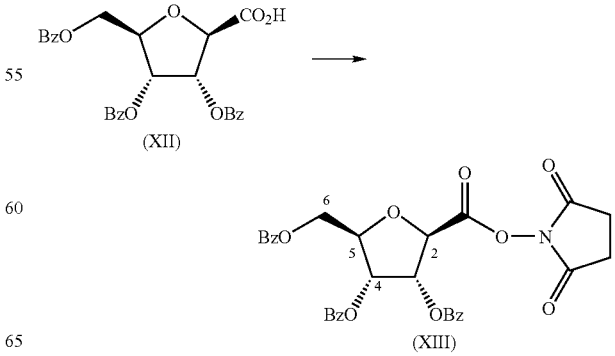

A solution of 2,3,5-tri-O-benzoyl-β-D-ribofuranosylcarboxylic acid (XII) (Collect. Czech. Chem. Comm. 43 (1978) 1431) (1.859 g, 3.77 mmol) in dry 1,2-dichloroethane (32 ml) was mixed with 1,3-dicyclohexylcarbodiimide (57 mg, 4.15 mmol) and N-hydroxysuccinic acid (478 mg, 4.15 mmol). The reaction mixture was stirred at room temperature under $N_2$ gas for 24 hours. The resulting precipitate was filtered off and the filtrate was concentrated under reduced pressure. The crude product of the compound (XIII) (99%) could be used directly for the subsequent reaction (see Example 13).

Example 13

Condensation of the hydrazine (XI) with the activated acid (XIII) to give the hydrazide (IVa)

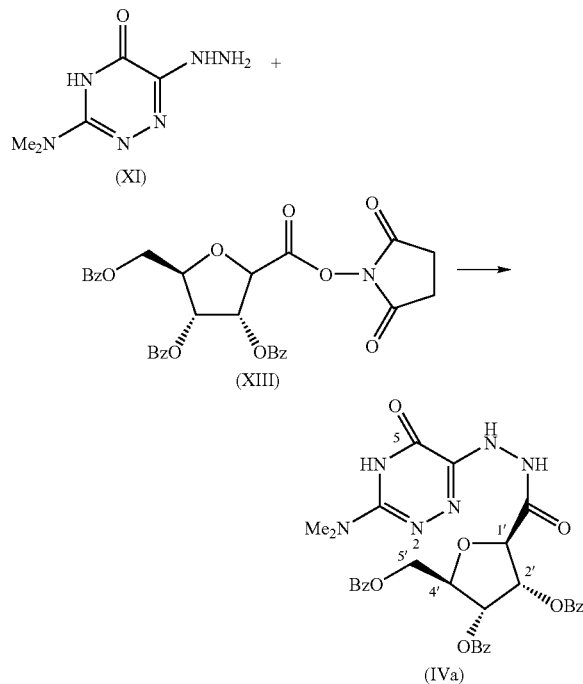

A solution of the hydrazine (XI) (706 mg, 4.15 mmol) in dried DMF (120 ml) was mixed with a solution of the activated acid (XIII) (2.2 g, 3.78 mmol) in dry DMF (20 ml) at room temperature. The mixture was stirred under an atmosphere of nitrogen at 60° C. for 24 hours, and excess solvent was then removed under reduced pressure, and the residue was dissolved in DCM. The organic phase was washed with water and sodium chloride solution and dried over $MgSO_4$. The solvent was stripped off under reduced pressure giving a yellow foam which was chromatographed over silica gel (mobile phase 10% acetone in DCM). Yield: 1.88 g=78% of theory of the compound (IVa) as colorless crystals; melting point 126-128° C.).

IR spectrum: $v_{max}$ (NaCl/film/cm$^{-1}$) 3253bs (NH), 3064w, 3010w, 2978w, 1730s (C=O, ester), 1715s (C=O, amide), 1651s, 1644s, 1634s, 1602s, 1587s, 1557w, 1538w, 1515s, 1505s, 1471w, 1464w, 1454s, 1397w, 1316w, 1271s, 1179s, 1179w, 1097w, 1026w, 931s, 756s, 711s, 687w; NMR spectrum: $\delta_H$ (270 MHz, CDCl$_3$) 9.98 (1H, bs, NH), 8.96 (1H, d, J 3.5, NH), 7.83-7.96 (4H, m Ar H), 7.80 (2H, d, J=1.4 Hz, Ar H), 7.28-7.58 (9H, m, Ar H), 6.16 (1H, dd, J 8.2, 4.6 Hz, H-2'), 6.00 (1H, dd, J 4.8, 2.1 Hz, H-3'), 4.94 (1H, d, J=2.1 Hz, H-1'), 4.81-4.86 (1H, m, H4'), 4.67 (1H, s, NH), 4.62-4.71 (2H, m, H-5'), 3.04 (6H, s, NCH$_3$); mass spectrum (FAB, NBA): found MH$^+$, 643.2222 C$_{32}$H$_{31}$N$_6$O$_9$, calculated MH, 643.2153.

Example 14

6-Dimethylamino-3-(2',3',5'-tri-O-benzoyl-β-ribofuranosyl)-1,2,4-triazolo-[3,4-f]-1,2,4-triazin-8(7H)-one (IIa-2)

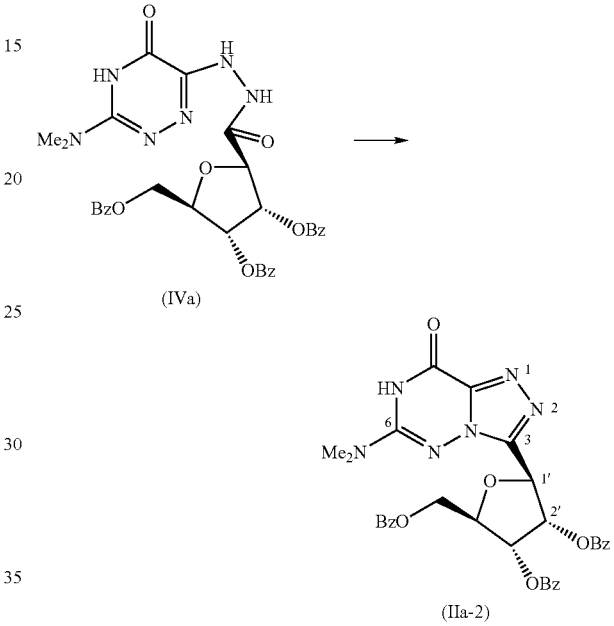

Method A

A solution of the hydrazide (IVa) (200 mg, 0.31 mmol) in dry DMF (40 ml) was heated at reflux under nitrogen gas for 24 hours. The mixture was cooled to room temperature and excess solvent was removed under reduced pressure, and the residue was then dissolved in dichloromethane (DCM). The organic phase was washed with water, dried over MgSO$_4$ and concentrated under reduced pressure, giving a yellowish solid which, after silica gel chromatography using 2 to 5% acetone/DCM, yielded the compound (IIa-2) (113 mg, 58%) of melting point 125-126° C. (petroleum ether/EtOAc): IR spectrum: $v_{max}$ (NaCl/film/cm$^{-1}$) 3200w (NH), 1728w (C=O, ester), 1611s, 1493s, 1452s, 1381s, 1316s, 1270s, 1178w, 1123s, 1071s, 1026w, 912w, 786w, 711s, 648w; NMR spectrum: $\delta_H$ (270 MHz, CDCl$_3$) 7.92-8.11 (6H, m, Ar H), 7.31-7.57 (9H, m, Ar H), 6.44 (1H, dd, J 5.8, 4.4 Hz, H-2'), 6.12 (1H, t, J=6.2 Hz, H-3'), 5.82 (1H, d, J=4.4 Hz, H-1'), 4.64-4.80 (3H, m, H-4' and H-5'), 3.19 (6H, s, NCH$_3$); mass spectrum (FAB, NBA): found MH$^+$, 625.2090 C$_{32}$H$_{29}$N$_6$O$_6$, calculated MH, 625.247.

Method B

A solution of the hydrazide (XI) (100 mg, 0.59 mmol) (see Example 13), the acid (XIII) (318 mg, 0.65 mmol) (see Example 13), DCC (134 mg, 0.65 mmol) and N-hydroxysuccinimide (74.5 mg, 0.65 mmol) in dry DMF was heated under reflux for 24 hours. The mixture was cooled to room temperature, the residue was dissolved in ethyl acetate and the organic phase was washed with water and sodium chloride solution, dried over MgSO$_4$ and concentrated under reduced pressure. The resulting yellowish solid was chromatographed over silica gel using 2 to 5% acetone/DCM, giving the compound (IIa-2) (56.5 mg, 58% of theory) as a white solid of the composition as obtained by Method A.

Example 15

8-Chloro6-dimethylamino-3-(2',3',5'-tri-O-benzoyl-β-D-ribofuranosyl)-1,2,4-triazolo[3,4-f]-1,2,4-triazine (II-2)

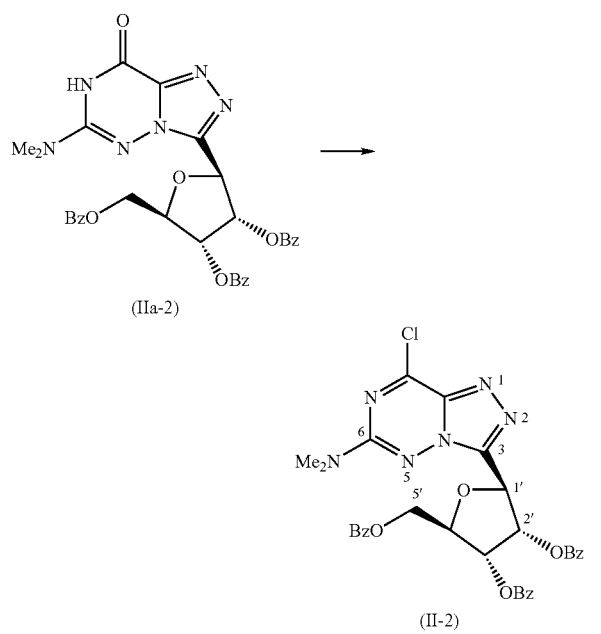

Method A

A mixture of the protected C-nucleoside (IIa-2) (150 mg, 0.24 mmol), N,N-dimethylaniline (1 ml) and phosphorus oxychloride (4 ml) was heated under reflux for 40 min. The mixture was cooled to room temperature and excess solvent was removed under reduced pressure, and the residue was then mixed with an ice/water mixture. The mixture was extracted with ethyl acetate (3×) and the combined organic phase was then dried over MgSO$_4$ and concentrated under reduced pressure. Chromatography of the residue using 30 to 40% ether in petroleum ether gave the chloride (II-2) (93 mg, 60% of theory) as yellow crystals of melting point 88-90° C. (DCM/petroleum ether).

IR spectrum: $v_{max}$ (NaCl/film/cm$^{-1}$) 3065w, 3034w, 3010w, 1729s (C=O, ester), 1596s, 1574s, 1505s, 1486s, 1452s, 1417s, 1382w, 1344w, 1316s, 1270s, 1179w, 1155, 1123s, 1096s, 1071s, 1027w, 958w, 912w, 805w, 785w, 712s, 688w;

NMR spectrum: $\delta_H$ (270 MHz, CDCl$_3$) 7.91-8.00 (6H, m, Ar H), 7.49-7.56 (3H, m, Ar H), 7.31-7.38 (6H, m, Ar H), 6.48 (1H, dd, J 5.7, 4.39 Hz, H-2'), 6.18 (1H, t, J=6.2 Hz, H-3'), 5.88 (1H, d, J=4.4 Hz, H-1'), 4.63-4.82 (2H, ml H4' and H5'), 3.21 (6H, s, NCH$_3$);

Mass spectrum (FBA, NBA): found MH+, 643.1738, C$_{32}$H$_{28}$ClN$_6$O$_7$, calculated: MH, 643.1708

Method B

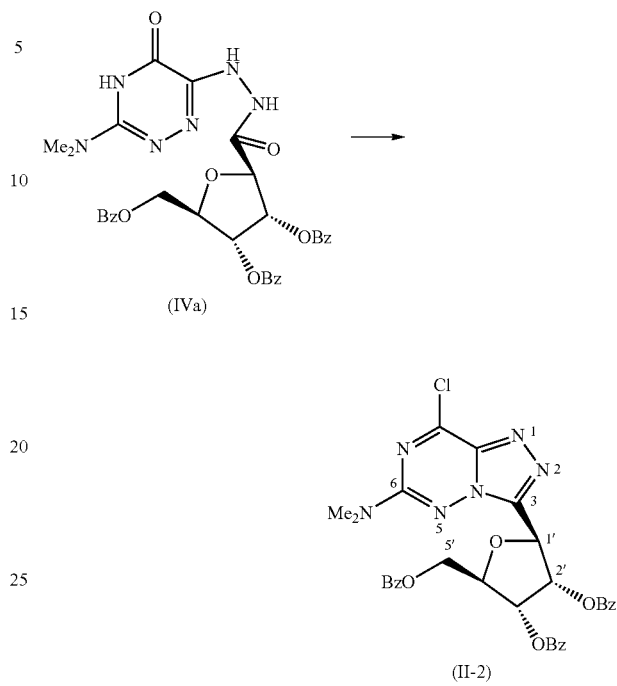

A mixture of the hydrazide (IVa) (100 mg, 0.16 mmol) and phosphorus oxychloride (POCl$_3$) (4 ml) was heated under reflux for 40 min. The mixture was cooled to room temperature and concentrated under reduced pressure, and the residue was mixed with an ice/water mixture. The mixture was extracted with ethyl acetate (3×), the extract was dried over MgSO$_4$ and concentrated under reduced pressure and the residue was then chromatographed over silica gel using 30 to 40% ether in petroleum ether. This gave the chloride (II-2) as yellow crystals (78 mg, 62%), analysis of which confirmed the chemical identity with the product from Method A.

Example 16

6-Dimethylamino-8-hydrazino-3-(2',3',5'-tri-O-benzoyl-β-D-ribofuranosyl)-1,2,4-triazolo[3,4-f]-1,2,4-triazine (II-3)

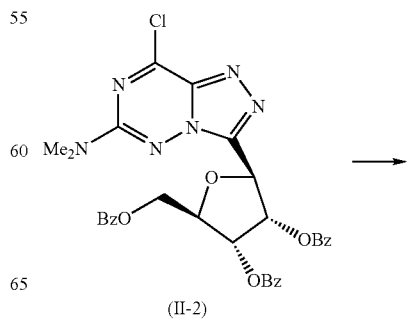

-continued

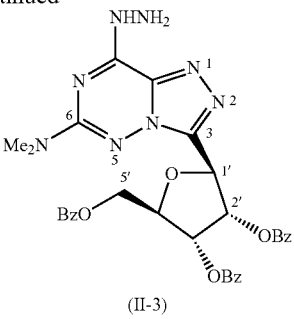

(II-3)

Hydrazine monohydrate (0.007 ml, 0.14 mmol) was added to a solution of the chloride (II-2) (80 mg, 0.13 mmol) in 2 ml of ethyl acetate, and the mixture was stirred at 25° C. for 5 min. This gave a yellow precipitate which was washed with ethyl acetate and recrystallized from ethyl acetate/petroleum ether. This gave compound (II-3) (70 mg, 88%) as yellowish crystals of melting point 78 to 79° C.

IR spectrum: $v_{max}$ (NaCl/film/cm$^{-1}$) 3320w, 3217w (NH), 3061w, 1725s (C=O, ester), 1692w, 1680w, 1659w, 1602s, 1584s, 1574w, 1548s, 1537s, 1514w, 1485w, 1452s, 1409w, 1316s, 1270s, 1124s, 1098s, 1026w, 962w, 711w.

NMR spectrum: $\delta_H$ (270 MHz, CDCl$_3$) 7.92-8.00 (6H, m, Ar H), 7.80 (1H, d, J=1.6 Hz, NH), 7.31-7.57 (9H, m, Ar H), 6.51 (1H, dd, J 5.7, 3.9 Hz, H-2'), 6.27 (1H, dd, J 6.9, 5.8 Hz, H-3'), 5.85 (1H, d, J=3.9 Hz, H-1'), 4.71-4.80 (2H, m, H-4' and H-5a'), 4.64-4.68 (1H, M, H-5b'), 3.18 (6H, s, NCH$_3$).

Mass spectrum (FAB, NBA): found MH$^+$, 639.2366 C$_{32}$H$_{31}$N$_8$O$_7$; calculated MH, 639.2316.

Example 17

6-Dimethylamino-3-(2',3',5'-tri-O-benzoyl-β-ribofuranosyl)-1,2,4-triazolo-[3,4-f]-1,2,4-triazine (If)

Method A

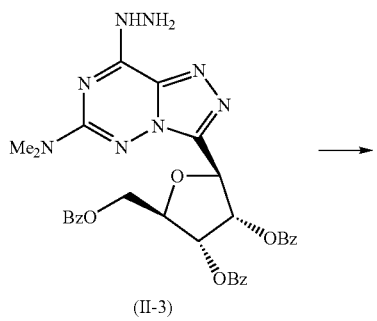

(II-3)

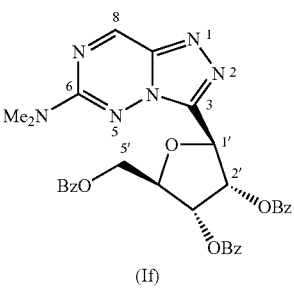

(If)

Yellow HgO (61 mg, 0.28 mmol) was, at 25° C., added to a solution of the hydrazine compound (II-3) (60 mg, 0.09 mmol) in ethanol (4 ml), and the reaction mixture was heated under reflux for 1 hour. The mixture was cooled and filtered through Celite, the Celite was washed with ethanol and the solvent was removed under reduced pressure, giving a yellowish solid which was chromatographed over silica gel using 10 to 20% ether in petroleum ether. Yield: 31 mg=55% of theory of the compound (If) as pale yellow crystals of melting point 79 to 80° C. (from DCM/petroleum ether). IR spectrum: $v_{max}$ (NaCl/film/cm$^{-1}$) 3065w, 3035w, 2929w, 1726s, (C=O, ester), 1682w, 1601s, 1565w, 1515w, 1493w, 1452w, 1416w, 1387w, 1342w, 1316w, 1269s, 1178w, 1122s, 1097s, 1071s, 1026s, 993w, 921w, 875w, 805w, 789w, 761w, 711s, 687w; NMR spectrum: $\delta_H$ (270 MHz, CDCl$_3$) 9.19 (1H, s, H-8), 7.93-8.02 (6H, m, Ar H), 7.50-7.56 (3H, m, Ar H), 7.34-7.40 (6H, m, Ar H), 6.48 (1H, dd, J 5.8, 4.4 Hz, H-2'), 6.21 (1H, t, J=6.2 Hz, H-3'), 5.90 (1H, d, J=4.2 Hz, H-1'), 4.66-4.80 (3H, m, H-4' and H-5'), 3.24 (6H, s, NCH$_3$);

Mass spectrum: found MH$^+$, 609.2113 C$_{32}$H$_{29}$N$_6$O$_7$, calculated MH, 609.2098.

Method B

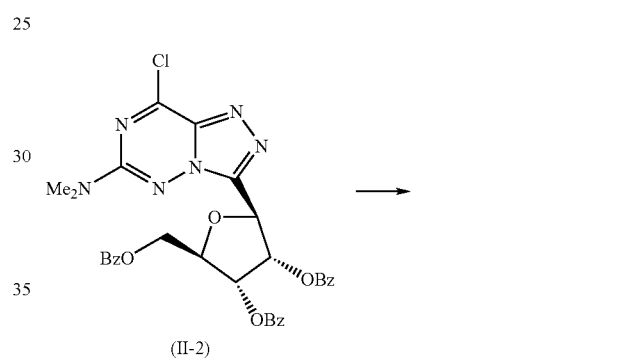

(II-2)

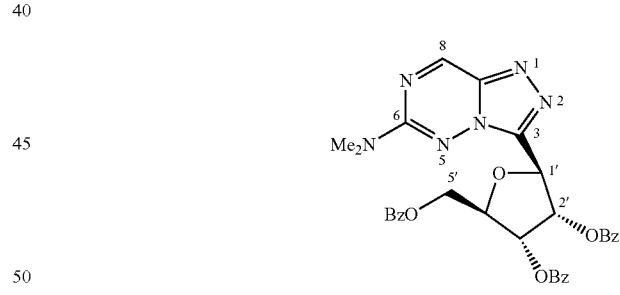

(If)

A solution of the chloro compound (II-2) (100 mg, 0.16 mmol) in dry acetic ester (6 ml) was mixed with 5% palladium/carbon (17 mg) and magnesium oxide (16 mg, 0.41 mmol), and the solution wasp at room temperature, covered for several days with hydrogen gas. The solution was filtered off through Celite, the Celite was washed with ethyl acetate, the solvent was removed under reduced pressure and the residue was then chromatographed over silica gel using 10 to 20% ether in petroleum ether. This gave the compound (If) as yellowish crystals (91 mg, 96%) with analysis data which were identical to those of the product obtained by Method A.

Example 18

6-Dimethylamino-3-β-ribofuranosyl-1,2,4-triazolo[3,4-f]-1,2,4-triazine (Ig)

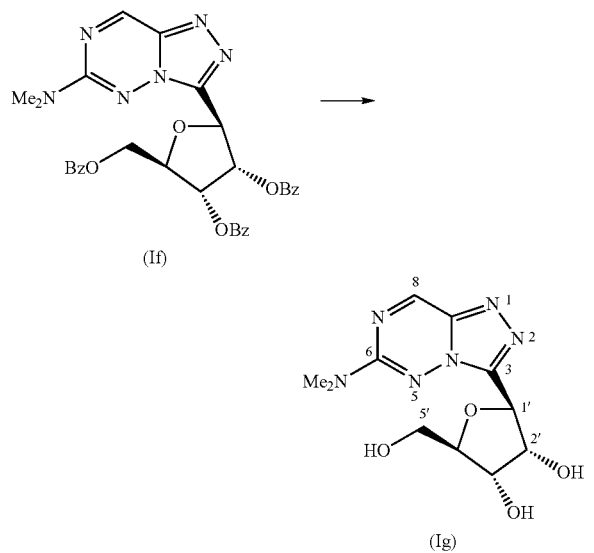

A solution of the protected C-nucleoside (I-f (90 mg, 0.15 mmol) in MeOH/NH$_3$ (5 ml, saturated at 0° C.) was stirred at room temperature for 2 days. The solvent was removed under reduced pressure and the residue was chromatographed over silica gel using 10 to 15% MeOH in DCM, giving the compound (I-g) (38 mg, 86%) as yellowish crystals of melting point 171-173° C. (acetone); IR spectrum: $v_{max}$ (NaCl/film/cm$^{-1}$) 3387bw, 3230bw (OH), 3021w, 1614s, 1573s, 1512w, 1481s, 1466w, 1440s, 1423s, 1384w, 1366s, 1344s, 1285s, 1216s, 1130s, 1100s, 1055s, 1032s, 1004s, 990w, 960s, 853s, 759s; NMR spectrum: $\delta_H$ (270 MHz, DMSO-d$_6$+D$_2$O) 9.35 (1H, s, H-8), 5.16 (1H, d, J 6.24H-1), 4.68 (1H, t, J=5.3 Hz, H-2'), 4.15 (1H, t, J=5.1 Hz, H-3'), 3.88-3.93 (1H, m, H4'), 3.44-3.62 (2H, m, H-5'), 3.12 (6H, s, NCH$_3$); Mass spectrum (FAB, NBA): found MH$^+$, 297.1330 C$_{11}$H$_{17}$N$_6$O$_4$, calculated MH, 297.1311.

Method B

Sodium methoxide (14 mg, 0.26 mmol) was added to a solution of the protected C-nucleoside (I-f) (50 mg, 0.08 mmol) in dry methanol (4 ml). The mixture was stirred at room temperature for 2 h and the reaction was then terminated by addition of 0.1 ml of water, the solvent was removed under reduced pressure and the residue was chromatographed over silica gel, mobile phase 10 to 15% methanol in DCM (gradient elution). This gave the compound (I-g) (21.9 mg, 90%) as yellowish crystals, analysis of which confirmed chemical identity with the product obtained by Method A.

Example 19

Compound (Ib) (see Example 3 above) (8 mg, 0.03 mmol) was, at room temperature, dissovled in 6M aqueous hydrochloric solution (2 ml). After 10 min, the solution was concentrated, giving the water addition product (I'b);
NMR spectrum: $\delta_H$ (300 MHz, D$_2$O) 8.22 (1H, s, H-5), 6.62 (1H, s, H-7'), 5.05 (1H, d, J=7 Hz, H-1'), 4.71 (1H, m, H-2'), 4.25 (1H, m, H-3'), 4.18 (1H, m, H-4'), 3.48 (2H, m, H-5').

Example 20

At room temperature, compound (Ig) (see Example 18 above) was dissovled in deuterium oxide, giving a mixture of the starting material (Ig) and the corresponding water addition product (I'g).
$^1$H-NMR (D$_2$O, 300 MHz) for the water addition product (I'g):
δ[ppm]=6.33 (d, 1H, J=2.8 Hz, H-8), 5.23 (dd, 1H, J=6.2 and 2.8 Hz, H-1'); 4.71 (t, 1H, J=6.0 Hz, H-2'), 4.34 (dt, 1H, J=5.8 and 9.4 Hz, H-3'), 4.17 (m, 1H, H4'), 3.68-3.92 (m, 2H, H-5'), 3.04 (s, 3H, NCH$_3$).

In the tables below, further examples of the Formula (I) are listed which are obtained by the abovementioned preparation examples or analogously to these examples and the processes mentioned in the description.

Explanations for the tables and the tabular examples below:

In the table in question, the definitions of the compound with a number according to Scheme N-1 ("N hyphen one") refer to the Formula (1), where the individual compounds are numbered consecutively using the integer "N", i.e. the first four compounds of the Formula (1) have the numbers 1-1, 2-1, 3-1, 4-1.

Correspondingly, compounds of the Formula (2) are numbered by the Scheme N-2 and compounds of the Formula (3) by the Scheme N-3.

The stereochemnical designations α and β indicate the positions of the bonds at the cyclic radicals relative to one another, i.e. a designation 1-β, 4-β or 1,4-β at a dihydrofuran radical of the Formula

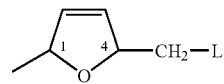

means that the bonds at position 1 and 4 are on the same side, based on the annular plane (cis-orientation). This designation does not indicate anything about the absolute configuration; thus, the formula embraces both enantiomorphous forms of the radical.

To designate an enantiomorphous form of the radical, the D,L-nomenclature, which is customary in sugar chemistry, is used. In the case of a five-membered ring derived from the furanosyl radical, the designation "D" refers to the absolute configuration at the asymmetric carbon atom in ring position 4 of the radical. A radical of the formula

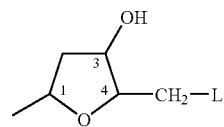

with the additional designation D-1,4-β-3-α (or in more detail 4D-1,4-β-3-α) is equivalent to the stereo formula

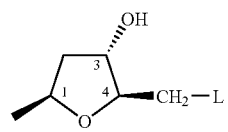

Using the R,S-nomenclature, this corresponds to the configuration 4R at ring position 4, if the priorities are in the following order: 1. Oxygen atom, 2. Carbon atom at position 3, 3. Group CH$_2$-L, 4. Hydrogen atom.

TABLE 1

Compounds of the Formulae (1), (2) and (3)
(see explanations on the nomenclature in the section above)

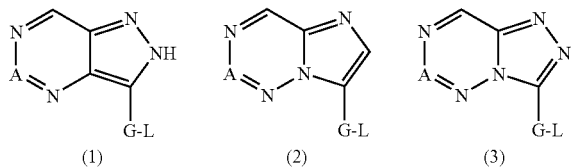

| No. | A | G—L | L | Phys. data |
|---|---|---|---|---|
| 1-1 | CH | —CH₂OCH₂CH₂—L | OH | Oil |
| 1-2 | " | " | " | |
| 1-3 | " | " | " | |
| 2-1 | CH | —CH₂CH₂CH(OH)CH₂—L | OH | |
| 2-2 | " | " | " | |
| 2-3 | " | " | " | |
| 3-1 | CH | —CH₂OCH(CH₂OH)CH₂—L | OH | |
| 3-2 | " | " | " | |
| 3-3 | " | " | " | |
| 4-1 | CH | —CH₂CH₂CH(CH₂OH)CH₂—L | OH | |
| 4-2 | " | " | " | |
| 4-3 | " | " | " | |
| 5-1 | CH | —CH₂CH(CH₂OH)CH₂CH₂—L | OH | |
| 5-2 | " | " | " | |
| 5-3 | " | " | " | |
| 6-1 | CH | —CH₂—C₆H₄—L | OH | |
| 6-2 | " | " | " | |
| 6-3 | " | " | " | |
| 7-1 | CH | —CH₂CH₂—C₆H₄—L | OH | |
| 7-2 | " | " | " | |
| 7-3 | " | " | " | |
| 8-1 | CH | —CH₂CH₂—(naphthyl)—L | OH | |
| 8-2 | " | " | " | |
| 8-3 | " | " | " | |
| 9-1 | CH | (tetrahydrofuran-2,5-diyl)—CH₂—L, 1,4-β | OH | |
| 9-2 | " | " | " | |
| 9-3 | " | " | " | |
| 10-1 | CH | (2,5-dihydrofuran-2,5-diyl)—CH₂—L, 1,4-β | OH | |
| 10-2 | " | " | " | |

TABLE 1-continued
Compounds of the Formulae (1), (2) and (3)
(see explanations on the nomenclature in the section above)
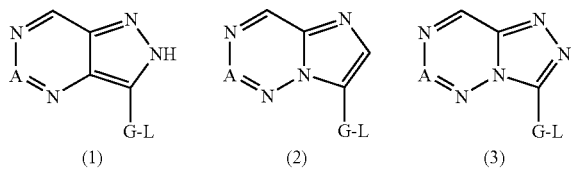
(1)　　　　　(2)　　　　　(3)
| No. | A | G—L | L | Phys. data |
|---|---|---|---|---|
| 10-3 | " | " | " | |
| 11-1 | CH | (4D-1,4-β-3-α) | OH | |
| 11-2 | " | " | " | |
| 11-3 | " | " | " | |
| 12-1 | CH | (4D-1,4-β-2,3-α) | OH | 227-228° C. |
| 12-2 | " | " | " | |
| 12-3 | " | " | " | |
| 13-1 | CH | (1,3-β) | OH | |
| 13-2 | " | " | " | |
| 13-3 | " | " | " | |
| 14-1 | CH | (1,4-β) | OH | |
| 14-2 | " | " | " | |
| 14-3 | " | " | " | |
| 15-1 | CH | (1,4-β-2,3-α) | OH | |
| 15-2 | " | " | " | |
| 15-3 | " | " | " | |
| 16-1 | CH | —CH$_2$CH$_2$CH(OAc)CH$_2$—L | OAc | |
| 16-2 | " | " | " | |
| 16-3 | " | " | " | |

TABLE 1-continued

Compounds of the Formulae (1), (2) and (3)
(see explanations on the nomenclature in the section above)

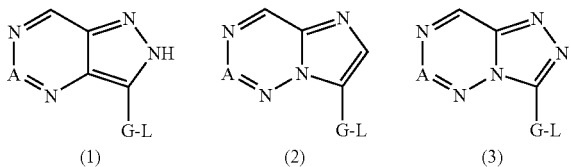

(1)   (2)   (3)

| No. | A | G—L | L | Phys. data |
|---|---|---|---|---|
| 17-1 | CH | AcO, OAc on tetrahydrofuran with CH₂—L; 4D-1,4-β-2,3-α | OAc | Foam |
| 17-2 | " | " | " | |
| 17-3 | " | " | " | |
| 18-1 | CH | AcO, OAc on cyclopentane with CH₂—L; 1,4-β-2,3-α | OAc | |
| 18-2 | " | " | " | |
| 18-3 | " | " | " | |
| 19-1 | $CNH_2$ | —CH$_2$OCH$_2$CH$_2$—L | OH | |
| 19-2 | " | " | " | |
| 19-3 | " | " | " | |
| 20-1 | $CNH_2$ | HO, OH on tetrahydrofuran with CH₂—L; 4D-1,2,3,4-β | OH | |
| 20-2 | " | " | " | |
| 20-3 | " | " | " | |
| 21-1 | $CNMe_2$ | HO, OH on tetrahydrofuran with CH₂—L; 4D-1,4-β-2,3-α | OH | |
| 21-2 | " | " | " | |
| 21-3 | " | " | " | 171-173° C. |
| 22-1 | CSMe | HO, OH on tetrahydrofuran with CH₂—L; 4D-1,4-β-2,3-α | OH | |
| 22-2 | " | " | " | 227-228° C. |
| 22-3 | " | " | " | |

TABLE 1-continued

Compounds of the Formulae (1), (2) and (3)
(see explanations on the nomenclature in the section above)

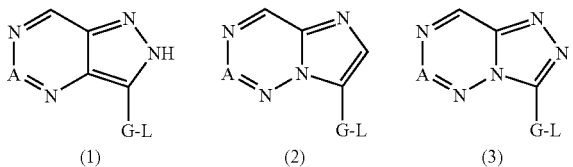

| No. | A | G—L | L | Phys. data |
|---|---|---|---|---|
| 23-1 | CNMe$_2$ | BzO, OBz on sugar, 4D-1,4-β-2,3-α | OBz | |
| 23-2 | " | " | " | |
| 23-3 | " | " | " | 79–80° C. |
| 24-1 | CSMe | Me,Me acetonide sugar, 4D-1,4-β-2,3-α | OH | |
| 24-2 | " | " | " | 92–93° C. |
| 24-3 | " | " | " | |
| 25-1 | N | —CH$_2$OCH$_2$CH$_2$—L | OH | |
| 25-2 | " | " | " | |
| 25-3 | " | " | " | |
| 26-1 | N | OH, OH on sugar, 4D-1,4-β-2,3-α | OH | |
| 26-2 | " | " | " | |
| 26-3 | " | " | " | |
| 27-1 | N | AcO, OAc on sugar, 4D-1,4-β-2,3-α | OAc | |
| 27-2 | " | " | " | |
| 27-3 | " | " | " | |
| 28-1 | CH | —CH$_2$OCH$_2$CH$_2$O—L | PO$_3$Na$_2$ | Solid |
| 28-2 | " | " | " | |
| 28-3 | " | " | " | |
| 29-1 | CH | —CH$_2$CH$_2$CH$_2$CH$_2$CH$_2$—L | PO$_3$H$_2$ | |
| 29-2 | " | " | " | |
| 29-3 | " | " | " | |
| 30-1 | CH | —CH$_2$CH$_2$CH$_2$OCH$_2$—L | PO$_3$H$_2$ | |
| 30-2 | " | " | " | |
| 30-3 | " | " | " | |

TABLE 1-continued

Compounds of the Formulae (1), (2) and (3)
(see explanations on the nomenclature in the section above)

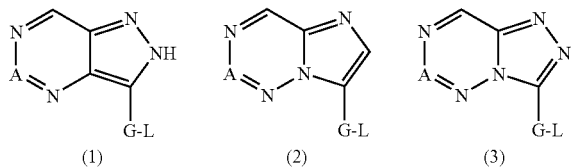

| No. | A | G—L | L | Phys. data |
|---|---|---|---|---|
| 31-1 | CH | —CH$_2$OCH$_2$CH$_2$OCH$_2$—L | PO$_3$H$_2$ | |
| 31-2 | " | " | " | |
| 31-3 | " | " | " | |
| 32-1 | CH | —CH$_2$OCH$_2$OCH$_2$—L | PO$_3$H$_2$ | |
| 32-2 | " | " | " | |
| 32-3 | " | " | " | |
| 33-1 | CH | —CH$_2$CH$_2$OCH$_2$—L | PO$_3$H$_2$ | |
| 33-2 | " | " | " | |
| 33-3 | " | " | " | |
| 34-1 | CH | —CH$_2$CH(Me)OCH$_2$—L | PO$_3$H$_2$ | |
| 34-2 | " | " | " | |
| 34-3 | " | " | " | |
| 35-1 | CH | —CH$_2$OCH(CH$_2$OH)CH$_2$CH$_2$—L | PO$_3$H$_2$ | |
| 35-2 | " | " | " | |
| 35-3 | " | " | " | |
| 36-1 | CH | —CH$_2$CH$_2$CH(CH$_2$OH)OCH$_2$—L | PO$_3$H$_2$ | |
| 36-2 | " | " | " | |
| 36-3 | " | " | " | |
| 37-1 | CH | —CH$_2$CH(CH$_2$OH)OCH$_2$—L | PO$_3$H$_2$ | |
| 37-2 | " | " | " | |
| 37-3 | " | " | " | |
| 38-1 | CH | —CH$_2$CH$_2$C(=CH$_2$)CH$_2$OCH$_2$—L | PO$_3$H$_2$ | |
| 38-2 | " | " | " | |
| 38-3 | " | " | " | |
| 39-1 | CH | —CH$_2$CH$_2$CH$_2$CH$_2$CH(CH$_2$Ph)—L | PO$_3$H$_2$ | |
| 39-2 | " | " | " | |
| 39-3 | " | " | " | |
| 40-1 | CH | —CH$_2$CH$_2$—(m-phenylene)—L | PO$_3$H$_2$ | |
| 40-2 | " | " | " | |
| 40-3 | " | " | " | |
| 41-1 | CH | —CH$_2$CH$_2$—(tetrahydronaphthyl)—L | PO$_3$H$_2$ | |
| 41-2 | " | " | " | |
| 41-3 | " | " | " | |
| 42-1 | CH | (tetrahydrofuran-2-yl)—CH$_2$CH$_2$—L, 1,4-β | PO$_3$H$_2$ | |
| 42-2 | " | " | " | |
| 43-3 | " | " | " | |
| 43-1 | CH | (2,5-dihydrofuran-2-yl)—CH$_2$CH$_2$—L, 1,4-β | PO$_3$H$_2$ | |

TABLE 1-continued

Compounds of the Formulae (1), (2) and (3)
(see explanations on the nomenclature in the section above)

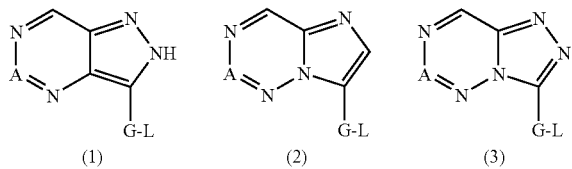

| No. | A | G—L | L | Phys. data |
|---|---|---|---|---|
| 43-2 | " | " | " | |
| 43-3 | " | " | " | |
| 44-1 | CH | OH OH <br> —⟨furanose⟩—CH$_2$O—L <br> 4D-1,4-β-2,3-α | PO$_3$Na$_2$ | >220° C. |
| 44-2 | " | " | " | |
| 44-3 | " | " | " | |
| 45-1 | CH | OH OH <br> —⟨furanose⟩—CH$_2$CH$_2$—L <br> 4D-1,4-β-2,3-α | PO$_3$H$_2$ | |
| 45-2 | " | " | " | |
| 45-3 | " | " | " | |
| 46-1 | CH | —⟨cyclopentane⟩—CH$_2$CH$_2$—L <br> 1,3-β | PO$_3$H$_2$ | |
| 46-2 | " | " | " | |
| 46-3 | " | " | " | |
| 47-1 | CH | —⟨cyclopentene⟩—CH$_2$CH$_2$—L <br> 1,4-β | PO$_3$H$_2$ | |
| 47-2 | " | " | " | |
| 47-3 | " | " | " | |
| 48-1 | CH | OH OH <br> —⟨cyclopentane⟩—CH$_2$CH$_2$—L <br> 1,4-β-2,3-α | PO$_3$H$_2$ | |
| 48-2 | " | " | " | |
| 48-3 | " | " | " | |
| 49-1 | CH | —⟨cyclopentane⟩—OCH$_2$—L <br> 1,3-β | PO$_3$H$_2$ | |

TABLE 1-continued

Compounds of the Formulae (1), (2) and (3)
(see explanations on the nomenclature in the section above)

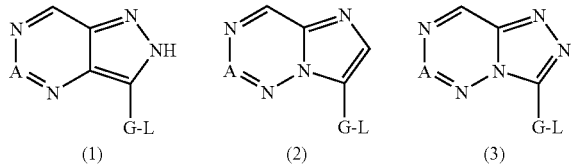

| No. | A | G—L | L | Phys. data |
|---|---|---|---|---|
| 49-2 | " | " | " | |
| 49-3 | " | " | " | |
| 50-1 | CH | (cyclopentenyl-O—CH₂—L), 1,4-β | $PO_3H_2$ | |
| 50-2 | " | " | " | |
| 50-3 | " | " | " | |
| 51-1 | CH | (HO, OH-cyclopentyl-O—CH₂—L), 1,4-β-2,3-α | $PO_3H_2$ | |
| 51-2 | " | " | " | |
| 51-3 | " | " | " | |
| 52-1 | CH | (AcO, OAc-cyclopentyl—CH₂—CH₂—L), 1,4-β-2,3-α | $PO_3Na_2$ | |
| 52-2 | " | " | " | |
| 52-3 | " | " | " | |
| 53-1 | CH | (AcO, OAc-cyclopentyl—OCH₂—L), 1,4-β-2,3-α | $PO_3Na_2$ | |
| 53-2 | " | " | " | |
| 53-3 | " | " | " | |
| 54-1 | CH | (S,O-dioxathiolane—CH₂—L), 1,4-β | $PO_3H_2$ | |
| 54-2 | " | " | " | |
| 54-3 | " | " | " | |
| 55-1 | CH | —CH₂CH₂CH₂OCH₂—L | P(O)(OH)(OEt) | |
| 55-2 | " | " | " | |
| 55-3 | " | " | " | |
| 56-1 | CH | —CH₂OCH(CH₂OH)CH₂CH₂—L | P(O)(OH)(OEt) | |
| 56-2 | " | " | " | |

TABLE 1-continued

Compounds of the Formulae (1), (2) and (3)
(see explanations on the nomenclature in the section above)

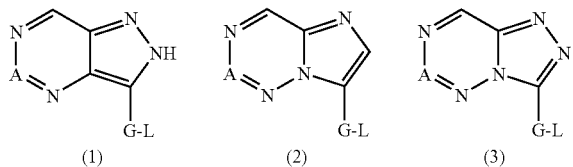

| No. | A | G—L | L | Phys. data |
|-----|---|-----|---|------------|
| 56-3 | " | " | " | |
| 57-1 | CH | ![structure: 1,4-β dioxathiolane-CH₂CH₂—L] | P(O)(OH)(OEt) | |
| 57-2 | " | " | " | |
| 57-3 | " | " | " | |
| 58-1 | CH | ![structure: 4D-1,4-β-2,3-α] | P(O)(OH) | |
| 58-2 | " | " | " | |
| 58-3 | " | " | " | |
| 59-1 | CH | —CH₂CH₂CH₂OCH₂—L | P(O)(OCH₂O—CO—t-Bu)₂ | |
| 59-2 | " | " | " | |
| 59-3 | " | " | " | |
| 60-1 | CH | —CH₂OCH₂CH₂OCH₂—L | P(O)(OCH₂O—CO—t-Bu)₂ | |
| 60-2 | " | " | " | |
| 60-3 | " | " | " | |
| 61-1 | CNH₂ | —CH₂CH₂CH₂OCH₂—L | PO₃H₂ | |
| 61-2 | " | " | " | |
| 61-3 | " | " | " | |
| 62-1 | CNH₂ | ![structure: 4-D-1,4-β-2,3-α] | PO₃H₂ | |
| 62-2 | " | " | " | |
| 62-3 | " | " | " | |
| 63-1 | CNMe₂ | —CH₂CH₂CH₂OCH₂—L | PO₃H₂ | |
| 63-2 | " | " | " | |
| 63-3 | " | " | " | |
| 64-1 | CSMe | —CH₂CH₂CH₂OCH₂—L | PO₃H₂ | |
| 64-2 | " | " | " | |
| 64-3 | " | " | " | |
| 65-1 | N | —CH₂CH₂CH₂OCH₂—L | PO₃H₂ | |
| 65-2 | " | " | " | |
| 65-3 | " | " | " | |
| 66-1 | N | ![structure: 4D-1,4-β-2,3-α] | PO₃H₂ | |

TABLE 1-continued

Compounds of the Formulae (1), (2) and (3)
(see explanations on the nomenclature in the section above)

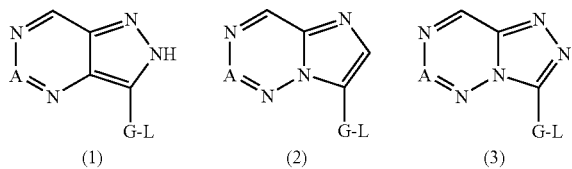

| No. | A | G—L | L | Phys. data |
|---|---|---|---|---|
| 66-2 | " | " | " | |
| 66-3 | " | " | " | |
| 67-1 | CH | —CH$_2$CH$_2$CH$_2$CH$_2$CH$_2$—L | CO$_2$H | |
| 67-2 | " | " | " | |
| 67-3 | " | " | " | |
| 68-1 | CH | —CH$_2$OCH$_2$CH$_2$CH$_2$—L | CO$_2$H | |
| 68-2 | " | " | " | |
| 68-3 | " | " | " | |
| 69-1 | CH | —CH$_2$CH$_2$CH$_2$OCH$_2$—L | CO$_2$H | |
| 69-2 | " | " | " | |
| 69-3 | " | " | " | |
| 70-1 | CH | —CH$_2$OCH$_2$CH$_2$OCH$_2$—L | CO$_2$H | |
| 70-2 | " | " | " | |
| 70-3 | " | " | " | |
| 71-1 | CH | —CH$_2$OCH$_2$OCH$_2$—L | CO$_2$H | |
| 71-2 | " | " | " | |
| 71-3 | " | " | " | |
| 72-1 | CH | —CH$_2$CH$_2$OCH$_2$—L | CO$_2$H | |
| 72-2 | " | " | " | |
| 72-3 | " | " | " | |
| 73-1 | CH | —CH$_2$CH(Me)OCH$_2$—L | CO$_2$H | |
| 73-2 | " | " | " | |
| 73-3 | " | " | " | |
| 74-1 | CH | —CH$_2$OCH(CH$_2$OH)CH$_2$CH$_2$—L | CO$_2$Na | |
| 74-2 | " | " | " | |
| 74-3 | " | " | " | |
| 75-1 | CH | —CH$_2$CH$_2$CH(CH$_2$OH)OCH$_2$—L | CO$_2$Na | |
| 75-2 | " | " | " | |
| 75-3 | " | " | " | |
| 76-1 | CH | —CH$_2$CH(CH$_2$CH)OCH$_2$—L | CO$_2$Na | |
| 76-2 | " | " | " | |
| 76-3 | " | " | " | |
| 77-1 | CH | —CH$_2$CH$_2$C(=CH$_2$)CH$_2$OCH$_2$—L | CO$_2$Na | |
| 77-2 | " | " | " | |
| 77-3 | " | " | " | |
| 78-1 | CH | —CH$_2$CH$_2$CH$_2$CH$_2$CH(CH$_2$Ph)—L | CO$_2$H | |
| 78-2 | " | " | " | |
| 78-3 | " | " | " | |
| 79-1 | CH | 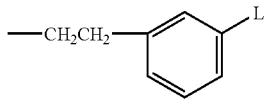 | CO$_2$H | |
| 79-2 | " | " | " | |
| 79-3 | " | " | " | |
| 80-1 | CH | 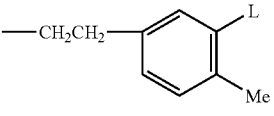 | CO$_2$H | |
| 80-2 | " | " | " | |
| 80-3 | " | " | " | |

TABLE 1-continued

Compounds of the Formulae (1), (2) and (3)
(see explanations on the nomenclature in the section above)

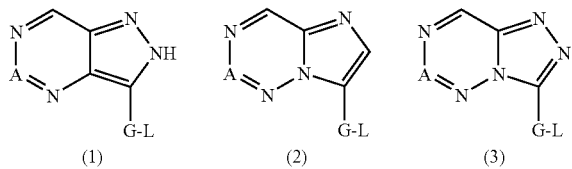

| No. | A | G—L | L | Phys. data |
|---|---|---|---|---|
| 81-1 | CH | —CH₂CH₂—[naphthyl]—L | CO₂H | |
| 81-2 | " | " | " | |
| 81-3 | " | " | " | |
| 82-1 | CH | —CH₂CH₂—[tetrahydronaphthyl-Br]—L | CO₂H | |
| 82-2 | " | " | " | |
| 82-3 | " | " | " | |
| 83-1 | CH | [tetrahydrofuran]—CH₂CH₂—L, 1,4-β | CO₂H | |
| 83-2 | " | " | " | |
| 83-3 | " | " | " | |
| 84-1 | CH | [dihydroxy-tetrahydrofuran]—CH₂CH₂—L, 4D-1,4-β, 2,3-α | CO₂Na | |
| 84-2 | " | " | " | |
| 84-3 | " | " | " | |
| 85-1 | CH | [cyclopentyl]—CH₂CH₂—L, 1,3-β | CO₂H | |
| 85-2 | " | " | " | |
| 85-3 | " | " | " | |
| 86-1 | CH | [cyclopentenyl]—CH₂CH₂—L | CO₂H | |
| 86-2 | " | " | " | |
| 86-3 | " | " | " | |

TABLE 1-continued

Compounds of the Formulae (1), (2) and (3)
(see explanations on the nomenclature in the section above)

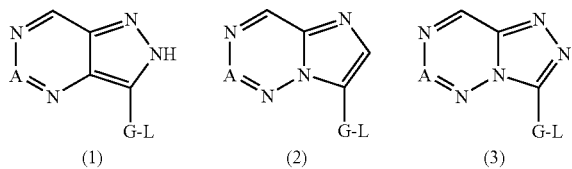

| No. | A | G—L | L | Phys. data |
|---|---|---|---|---|
| 87-1 | CH | (cyclopentane with OH, OH, —CH₂CH₂—L) 4D-β-2,3-α | CO₂Na | |
| 87-2 | " | " | " | |
| 87-3 | " | " | " | |
| 88-1 | CH | (cyclopentane with —OCH₂—L) 1,3-β | CO₂H | |
| 88-2 | " | " | " | |
| 88-3 | " | " | " | |
| 89-1 | CH | (cyclopentene with —O—CH₂—L) 1,4-β | CO₂H | |
| 89-2 | " | " | " | |
| 89-3 | " | " | " | |
| 90-1 | CH | (tetrahydrofuran with HO, OH, —O—CH₂—L) 4D-1,4-β-2,3-α | CO₂Na | |
| 90-2 | " | " | " | |
| 90-3 | " | " | " | |
| 91-1 | CH | (1,3-oxathiolane with —CH₂CH₂—L) 1,4-β | CO₂H | |
| 91-2 | " | " | " | |
| 91-3 | " | " | " | |
| 92-1 | CH | —CH₂CH₂CH₂OCH₂—L | CO₂Me | |
| 92-2 | " | " | " | |
| 92-3 | " | " | " | |
| 93-1 | CH | —CH₂CH₂CH₂CH₂CH(CH₂Ph) | CO₂Me | |
| 93-2 | " | " | " | |
| 93-3 | " | " | " | |

TABLE 1-continued

Compounds of the Formulae (1), (2) and (3)
(see explanations on the nomenclature in the section above)

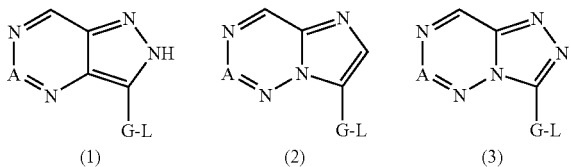

| No. | A | G—L | L | Phys. data |
|---|---|---|---|---|
| 94-1 | CH | —CH$_2$CH$_2$—(phenyl with L at meta) | CO$_2$Me | |
| 94-2 | " | " | " | |
| 94-3 | " | " | " | |
| 95-1 | CH | —CH$_2$CH$_2$—(phenyl with L and Me) | CO$_2$Me | |
| 95-2 | " | " | " | |
| 95-3 | " | " | " | |
| 96-1 | CH | —CH$_2$CH$_2$—(naphthyl with L) | CO$_2$Me | |
| 96-2 | " | " | " | |
| 96-3 | " | " | " | |
| 97-1 | CH | —CH$_2$CH$_2$—(tetrahydronaphthyl with L and Br) | CO$_2$Me | |
| 97-2 | " | " | " | |
| 97-3 | " | " | " | |
| 98-1 | CH | —CH$_2$CH$_2$—(phenyl with L and Me) | CO$_2$Et | |
| 98-2 | " | " | " | |
| 98-3 | " | " | " | |
| 99-1 | CH | —CH$_2$CH$_2$—(naphthyl with L) | CO$_2$Et | |
| 99-2 | " | " | " | |
| 99-3 | " | " | " | |

TABLE 1-continued

Compounds of the Formulae (1), (2) and (3)
(see explanations on the nomenclature in the section above)

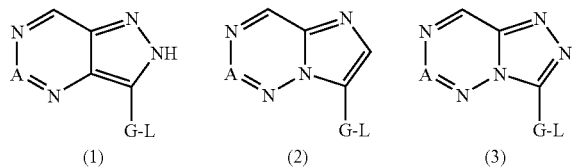

| No. | A | G—L | L | Phys. data |
|---|---|---|---|---|
| 100-1 | CH | —CH₂CH₂— (tetrahydronaphthalene with L, Br substituents) | CO₂Et | |
| 100-2 | " | " | " | |
| 100-3 | " | " | " | |
| 101-1 | CH | (tetrahydrofuran)—CH₂CH₂—L  1,4-β | CO₂Me | |
| 101-2 | " | " | " | |
| 101-3 | " | " | " | |
| 102-1 | CH | AcO, OAc (tetrahydrofuran)—CH₂CH₂—L | CO₂Me | |
| 102-2 | " | " | " | |
| 102-3 | " | " | " | |
| 103-1 | CH | AcO, OAc (cyclopentane)—CH₂CH₂—L  4D-1,4-β-2,3-α | CO₂Me | |
| 103-2 | " | " | " | |
| 103-3 | " | " | " | |
| 104-1 | CH | (1,3-oxathiolane)—CH₂CH₂—L  1,4-β | CO₂Me | |
| 104-2 | " | " | " | |
| 104-3 | " | " | " | |
| 105-1 | CH | HO (furo-pyran with O—L)  4D-1,4-β-2,3-α | CO | |

TABLE 1-continued

Compounds of the Formulae (1), (2) and (3)
(see explanations on the nomenclature in the section above)

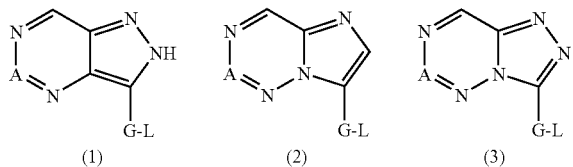

| No. | A | G—L | L | Phys. data |
|---|---|---|---|---|
| 105-2 | " | " | " | |
| 105-3 | " | " | " | |
| 106-1 | CNH$_2$ | CH$_2$CH$_2$CH$_2$OCH$_2$ | CO$_2$H | |
| 106-2 | " | " | " | |
| 106-3 | " | " | " | |
| 107-1 | CNH$_2$ | [4D-1,4-β-2,3-α sugar: HO, OH, —CH$_2$CH$_2$—L] | CO$_2$Na | |
| 107-2 | " | " | " | |
| 107-3 | " | " | " | |
| 108-1 | CNMe$_2$ | —CH$_2$CH$_2$CH$_2$OCH$_2$—L | CO$_2$H | |
| 108-2 | " | " | " | |
| 108-3 | " | " | " | |
| 109-1 | CSMe | —CH$_2$CH$_2$CH$_2$OCH$_2$—L | CO$_2$H | |
| 109-2 | " | " | " | |
| 109-3 | " | " | " | |
| 110-1 | N | —CH$_2$CH$_2$CH$_2$OCH$_2$—L | CO$_2$H | |
| 110-2 | " | " | " | |
| 110-3 | " | " | " | |
| 111-1 | N | [4D-1,4-β-2,3-α sugar: HO, OH, —CH$_2$CH$_2$—L] | CO$_2$Na | |
| 111-2 | " | " | " | |
| 111-3 | " | " | " | |
| 112-1 | N | [1,4-β cyclopentane: —O—CH$_2$—L] | CO$_2$H | |
| 112-2 | " | " | " | |
| 112-3 | " | " | " | |
| 113-1 | C—F | [4D-1,4-β-2,3-α sugar: OH, OH, —CH$_2$—CH$_2$—L] | CO$_2$H | |
| 113-2 | " | " | " | |
| 113-3 | " | " | " | |

TABLE 1-continued

Compounds of the Formulae (1), (2) and (3)
(see explanations on the nomenclature in the section above)

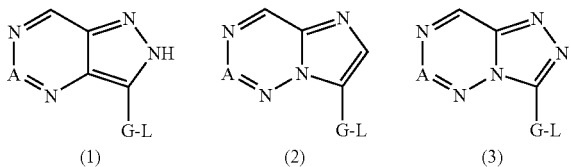

| No. | A | G—L | L | Phys. data |
|---|---|---|---|---|
| 114-1 | C—CN | OH, OH, —CH₂—CH₂—L (tetrahydrofuran), 4D-1,4-β-2,3-α | CO₂H | |
| 114-2 | " | " | " | |
| 114-3 | " | " | " | |
| 115-1 | C—OMe | OH, OH, —CH₂—CH₂—L (tetrahydrofuran), 4D-1,4-β-2,3-α | CO₂H | |
| 115-2 | " | " | " | |
| 115-3 | " | " | " | |
| 116-1 | CH | —CH₂CH₂—(naphthyl)—L | NHSO₂CF₃ | |
| 116-2 | " | " | " | |
| 116-3 | " | " | " | |
| 117-1 | CH | —CH₂CH₂—(naphthyl)—L | SO₂NHCOMe | |
| 117-2 | " | " | " | |
| 117-3 | " | " | " | |
| 118-1 | CNH₂ | —CH₂CH₂—(tetrahydronaphthyl, Br)—L | CO₂H | |
| 118-2 | " | " | " | |
| 118-3 | " | " | " | |
| 119-1 | N | " | CO₂H | |
| 119-2 | " | " | " | |
| 119-3 | " | " | " | |
| 120-1 | C—SH | " | CO₂H | |
| 121-2 | " | " | " | |

TABLE 1-continued

Compounds of the Formulae (1), (2) and (3)
(see explanations on the nomenclature in the section above)

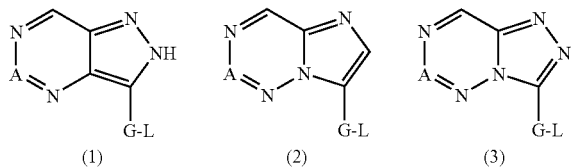

| No. | A | G—L | L | Phys. data |
|---|---|---|---|---|
| 121-3 | " | " | " | |
| 122-1 | C—OH | " | CO$_2$H | |
| 122-2 | " | " | " | |
| 122-3 | " | " | " | |
| 123-1 | C—Cl | " | CO$_2$H | |
| 123-2 | " | " | " | |
| 123-3 | " | " | " | |
| 124-1 | C—N$_3$ | " | CO$_2$H | |
| 124-2 | " | " | " | |
| 124-3 | " | " | " | |
| 125-1 | C—CN | " | CO$_2$H | |
| 125-2 | " | " | " | |
| 125-3 | " | " | " | |
| 126-1 | C—OMe | " | CO$_2$H | |
| 126-2 | " | " | " | |
| 126-3 | " | " | " | |
| 127-1 | CH | " | SO$_3$Na | |
| 127-2 | " | " | " | |
| 127-3 | " | " | " | |
| 128-1 | COH | " | SO$_3$Na | |
| 128-2 | " | " | " | |
| 128-3 | " | " | " | |
| 129-1 | CSH | " | SO$_3$Na | |
| 129-2 | " | " | " | |
| 129-3 | " | " | " | |
| 130-1 | COH | " | SO$_2$NH$_2$ | |
| 130-2 | " | " | " | |
| 130-3 | " | " | " | |
| 131-1 | CCN | " | SO$_2$NH$_2$ | |
| 131-2 | " | " | " | |
| 131-3 | " | " | " | |
| 132-1 | C—N$_3$ | " | SO$_2$NH$_2$ | |
| 132-2 | " | " | " | |
| 132-3 | " | " | " | |
| 133-1 | CCN | " | CO$_2$Na | |
| 133-2 | " | " | " | |
| 133-3 | " | " | " | |
| 134-1 | C—OMe | " | CO$_2$Na | |
| 134-2 | " | " | " | |
| 134-3 | " | " | " | |
| 135-1 | CH | —CH$_2$CH$_2$— (tetrahydronaphthalene)—L | NHSO$_2$CF$_3$ | |
| 135-2 | " | " | " | |
| 135-3 | " | " | " | |
| 136-1 | " | " | NHSO$_2$CH$_2$CN | |
| 136-2 | " | " | " | |
| 136-3 | " | " | " | |
| 137-1 | " | " | NHSO$_2$Me | |
| 137-2 | " | " | " | |
| 137-3 | " | " | " | |
| 138-1 | " | " | CO—NHSO$_2$Me | |
| 138-2 | " | " | " | |
| 138-3 | " | " | " | |
| 139-1 | " | " | CO—NMe$_2$ | |
| 139-2 | " | " | " | |

TABLE 1-continued

Compounds of the Formulae (1), (2) and (3)
(see explanations on the nomenclature in the section above)

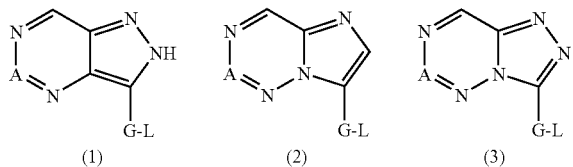

| No. | A | G—L | L | Phys. data |
|---|---|---|---|---|
| 139-3 | " | " | " | |
| 140-1 | " | " | PO(OPh)$_2$ | |
| 140-2 | " | " | " | |
| 140-3 | " | " | " | |
| 141-1 | " | " | P(=S)(OH)$_2$ | |
| 141-2 | " | " | " | |
| 141-3 | " | " | " | |
| 142-1 | " | " | CO$_2$Me | |
| 142-2 | " | " | " | |
| 142-3 | " | " | " | |
| 143-1 | C—NO$_2$ | AcO, OAc furanose ring with CH$_2$—L; 4D-1,4-β-2-3-α | OAc | |
| 143-2 | " | " | " | |
| 143-3 | " | " | " | |
| 144-1 | C—CF$_3$ | " | OAc | |
| 144-2 | " | " | " | |
| 144-3 | " | " | " | |
| 145-1 | CH | OH, OH furanose ring with CH$_2$—L; 4D-1,4-β-2,3-α | O—CO—Et | |
| 145-2 | " | " | " | |
| 145-3 | " | " | " | |
| 146-1 | " | EtCOO, OCOEt furanose ring with CH$_2$—L; 4D-1,4-β-2,3-α | " | |
| 146-2 | " | " | " | |
| 146-3 | " | " | " | |
| 147-1 | C—Me | —CH$_2$CH$_2$—(phenyl)—L | P(=O)(OH)$_2$ | |
| 147-2 | " | " | " | |
| 147-3 | " | " | " | |
| 148-1 | C—Et | " | " | |
| 148-2 | " | " | " | |
| 148-3 | " | " | " | |

TABLE 1-continued

Compounds of the Formulae (1), (2) and (3)
(see explanations on the nomenclature in the section above)

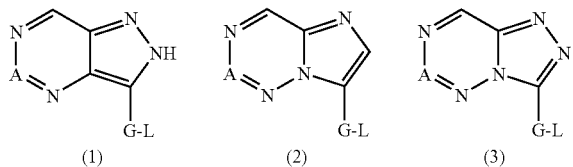

| No. | A | G—L | L | Phys. data |
|---|---|---|---|---|
| 149-1 | N | OH OH<br>![structure]<br>CH$_2$—L<br>4D-1,4-β-2,3-α | NHAc | |
| 149-2 | " | " | " | |
| 149-3 | " | " | " | |
| 150-1 | " | " | NHSO$_2$CH$_2$CN | |
| 150-2 | " | " | " | |
| 150-3 | " | " | " | |
| 151-1 | " | " | NHSO$_2$Me | |
| 151-2 | " | " | " | |
| 151-3 | " | " | " | |
| 152-1 | " | " | CONHSO$_2$Me | |
| 152-2 | " | " | " | |
| 152-3 | " | " | " | |
| 153-1 | " | " | CONMe$_2$ | |
| 153-2 | " | " | " | |
| 153-3 | " | " | " | |
| 154-1 | " | " | PO(OPh)$_2$ | |
| 154-2 | " | " | " | |
| 154-3 | " | " | " | |
| 155-1 | " | " | PO(O—n-Bu)$_2$ | |
| 155-2 | " | " | " | |
| 155-3 | " | " | " | |
| 156-1 | CH | ![structure with S, O, CH$_2$—L]<br>1,4-β | OH | |
| 156-2 | " | " | " | |
| 156-3 | " | " | " | |
| 157-1 | CH | —CH$_2$OCH$_2$CH$_2$—L | OAc | Oil |
| 157-2 | " | " | " | |
| 157-3 | " | " | " | |
| 158-1 | CH | ![furan structure]<br>CH$_2$CH$_2$—L<br>1,4-β | CO$_2$H | |
| 158-2 | " | " | " | |
| 158-3 | " | " | " | |
| 159-1 | CNH$_2$ | HO OH<br>![structure]<br>CH$_2$—L<br>4D-1,4-β-2,3-α | OH | |

TABLE 1-continued
Compounds of the Formulae (1), (2) and (3)
(see explanations on the nomenclature in the section above)
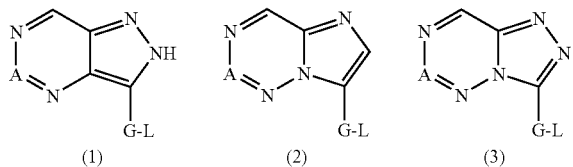
| No. | A | G—L | L | Phys. data |
|---|---|---|---|---|
| 159-2 | " | " | " | |
| 159-3 | " | " | " | NMR (see after Tab. 1) |
| 160-1 | C—SH | ![4D-1,4-β-2,3-α] | OH | |
| 160-2 | " | " | " | |
| 160-3 | " | " | " | |
| 161-1 | C—SH | ![4D-1,2,3,4-β] | OH | |
| 161-2 | " | " | " | |
| 161-3 | " | " | " | |
| 162-1 | C—SH | ![1,4-β-2,3-α] | OH | |
| 162-2 | " | " | " | |
| 162-3 | " | " | " | |
| 163-1 | C—SH | ![1,2,3,4-β] | OH | |
| 163-2 | " | " | " | |
| 163-3 | " | " | " | |
| 164-1 | C—SH | ![1,4-β-2,3-α] | OH | |
| 164-2 | " | " | " | |
| 164-3 | " | " | " | |

Regarding Example 159-3:

The compound was dissolved at room temperature in deuterium oxide, giving a solution of the mixture of compound 159-3 and its water addition product (I') in the ratio 5:95. $^1$H-NMR (D$_2$O, 300 MHz): δ [ppm]=6.35 (s, 1H, H-6), 5.15 (d, 1H, H-1); 4.70 (dd, 1H, H-2'), 4.35 (dd, 1H, H-3'), 4.20 (ddd, 1H, H-4'), 3.90-3.60 (dd, 2H, H-5', 5").

TABLE 2

Compounds of the Formulae (4), (5) and (6)
(for how the Table 2 is constructed, cf. analogous explanations for Table 1)

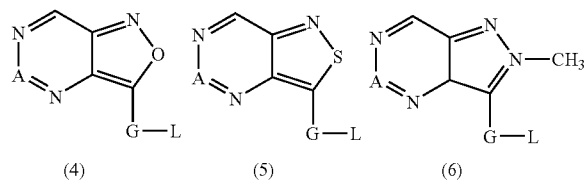

| No. | A | G—L | L | Phys. data |
|---|---|---|---|---|
| 1-4 | CH | —CH$_2$OCH$_2$CH$_2$—L | OH | |
| 1-5 | CH | —CH$_2$OCH$_2$CH$_2$—L | OH | |
| 1-6 | CH | —CH$_2$OCH$_2$CH$_2$—L | OH | |
| 2-4 | CH | —CH$_2$CH$_2$CH(OH)CH$_2$—L | OH | |
| 2-5 | CH | —CH$_2$CH$_2$CH(OH)CH$_2$—L | OH | |
| 2-6 | CH | —CH$_2$CH$_2$CH(OH)CH$_2$—L | OH | |
| 3-4 | CH | —CH$_2$OCH(CH$_2$OH)CH$_2$—L | OH | |
| 3-5 | CH | —CH$_2$OCH(CH$_2$OH)CH$_2$—L | OH | |
| 3-6 | CH | —CH$_2$OCH(CH$_2$OH)CH$_2$—L | OH | |
| 4-4 | CH | —CH$_2$CH$_2$CH(CH$_2$OH)CH$_2$—L | OH | |
| 4-5 | CH | —CH$_2$CH$_2$CH(CH$_2$OH)CH$_2$—L | OH | |
| 4-6 | CH | —CH$_2$CH$_2$CH(CH$_2$OH)CH$_2$—L | OH | |
| 5-4 | CH | —CH$_2$CH(CH$_2$OH)CH$_2$CH$_2$—L | OH | |
| 5-5 | CH | —CH$_2$CH(CH$_2$OH)CH$_2$CH$_2$—L | OH | |
| 5-6 | CH | —CH$_2$CH(CH$_2$OH)CH$_2$CH$_2$—L | OH | |
| 6-4 | CH | —CH$_2$-phenyl-L | OH | |
| 6-5 | CH | —CH$_2$-phenyl-L | OH | |
| 6-6 | CH | —CH$_2$-phenyl-L | OH | |
| 7-4 | CH | —CH$_2$CH$_2$-phenyl-L | OH | |
| 7-5 | CH | —CH$_2$CH$_2$-phenyl-L | OH | |
| 7-6 | CH | —CH$_2$CH$_2$-phenyl-L | OH | |
| 8-4 | CH | —CH$_2$CH$_2$-naphthyl-L | OH | |
| 8-5 | CH | —CH$_2$CH$_2$-naphthyl-L | OH | |
| 8-6 | CH | —CH$_2$CH$_2$-naphthyl-L | OH | |
| 9-4 | CH | tetrahydrofuran-CH$_2$—L, 1,4-β | OH | |
| 9-5 | CH | tetrahydrofuran-CH$_2$—L, 1,4-β | OH | |
| 9-6 | CH | tetrahydrofuran-CH$_2$—L, 1,4-β | OH | |
| 10-4 | CH | dihydrofuran-CH$_2$—L, 1,4-β | OH | |
| 10-5 | CH | dihydrofuran-CH$_2$—L, 1,4-β | OH | |
| 10-6 | CH | dihydrofuran-CH$_2$—L, 1,4-β | OH | |

TABLE 2-continued

Compounds of the Formulae (4), (5) and (6)
(for how the Table 2 is constructed, cf. analogous explanations for Table 1)

(4), (5), (6) [structures shown]

| No. | A | G—L | L | Phys. data |
|---|---|---|---|---|
| 11-4 | CH | 4D-1,4-β-3-α tetrahydrofuran with OH, CH₂—L | OH | |
| 11-5 | CH | 4D-1,4-β-3-α tetrahydrofuran with OH, CH₂—L | OH | |
| 11-6 | CH | 4D-1,4-β-3-α tetrahydrofuran with OH, CH₂—L | OH | |
| 12-4 | CH | 4D-1,4-β-2,3-α tetrahydrofuran with HO, OH, CH₂—L | OH | |
| 12-5 | CH | 4D-1,4-β-2,3-α tetrahydrofuran with HO, OH, CH₂—L | OH | |
| 12-6 | CH | 4D-1,4-β-2,3-α tetrahydrofuran with HO, OH, CH₂—L | OH | |
| 13-4 | CH | 1,3-β cyclopentane—CH₂—L | OH | |
| 13-5 | CH | 1,3-β cyclopentane—CH₂—L | OH | |
| 13-6 | CH | 1,3-β cyclopentane—CH₂—L | OH | |
| 14-4 | CH | 1,4-β cyclopentene—CH₂—L | OH | |
| 14-5 | CH | 1,4-β cyclopentene—CH₂—L | OH | |
| 14-6 | CH | 1,4-β cyclopentene—CH₂—L | OH | |
| 15-4 | CH | 1,4-β-2,3-α cyclopentane with HO, OH, CH₂—L | OH | |
| 15-5 | CH | 1,4-β-2,3-α cyclopentane with HO, OH, CH₂—L | OH | |
| 15-6 | CH | 1,4-β-2,3-α cyclopentane with HO, OH, CH₂—L | OH | |
| 16-4 | CH | 1,4-β-2,3-α 1,3-oxathiolane—CH₂—L | OH | |
| 16-5 | CH | 1,4-β-2,3-α 1,3-oxathiolane—CH₂—L | OH | |
| 16-6 | CH | 1,4-β-2,3-α 1,3-oxathiolane—CH₂—L | OH | |

TABLE 2-continued

Compounds of the Formulae (4), (5) and (6)
(for how the Table 2 is constructed, cf. analogous explanations for Table 1)

(4) / (5) / (6)

| No. | A | G—L | L | Phys. data |
|---|---|---|---|---|
| 17-4 | CH | —CH$_2$OCH$_2$CH$_2$—L | OAc | |
| 17-5 | CH | —CH$_2$OCH$_2$CH$_2$—L | OAc | |
| 17-6 | CH | —CH$_2$OCH$_2$CH$_2$—L | OAc | |
| 18-4 | CH | —CH$_2$CH$_2$CH(OAc)CH$_2$—L | OAc | |
| 18-5 | CH | —CH$_2$CH$_2$CH(OAc)CH$_2$—L | OAc | |
| 18-6 | CH | —CH$_2$CH$_2$CH(OAc)CH$_2$—L | OAc | |
| 19-4 | CH | 4D-1,4-β-2,3-α | OAc | |
| 19-5 | CH | 4D-1,4-β-2,3-α | OAc | |
| 19-6 | CH | 4D-1,4-β-2,3-α | OAc | |
| 20-4 | CH | 1,4-β-2,3-α | OAc | |
| 20-5 | CH | 1,4-β-2,3-α | OAc | |
| 20-6 | CH | 1,4-β-2,3-α | OAc | |
| 21-4 | N | —CH$_2$OCH$_2$CH$_2$—L | OH | |
| 21-5 | N | —CH$_2$OCH$_2$CH$_2$—L | OH | |
| 21-6 | N | —CH$_2$OCH$_2$CH$_2$—L | OH | |
| 22-4 | N | 4D-1,2,3,4-β | OAc | |
| 22-5 | N | 4D-1,2,3,4-β | OAc | |
| 22-6 | N | 4D-1,2,3,4-β | OAc | |
| 23-4 | N | 4D-1,2,3,4-β | OH | |
| 23-5 | N | 4D-1,2,3,4-β | OH | |
| 23-6 | N | 4D-1,2,3,4-β | OH | |
| 24-4 | N | 4D-1,4-β-2,3-α | OH | |
| 24-5 | N | 4D-1,4-β-2,3-α | OH | |

TABLE 2-continued

Compounds of the Formulae (4), (5) and (6)
(for how the Table 2 is constructed, cf. analogous explanations for Table 1)

(4), (5), (6) structures with G—L substituent

| No. | A | G—L | L | Phys. data |
|---|---|---|---|---|
| 24-6 | N | (sugar with HO, OH, CH₂—L; 4D-1,4-β-2,3-α) | OH | |
| 25-4 | N | (sugar with BzO, OBz, CH₂—L; 4D-1,4-β-2,3-α) | OBz | |
| 25-5 | N | (sugar with BzO, OBz, CH₂—L; 4D-1,4-β-2,3-α) | OBz | |
| 25-6 | N | (sugar with BzO, OBz, CH₂—L; 4D-1,4-β-2,3-α) | OBz | |
| 26-4 | N | (acetonide sugar with Me, Me, CH₂—L; 4D-1,4-β-2,3-α) | OH | |
| 26-5 | N | (acetonide sugar with Me, Me, CH₂—L; 4D-1,4-β-2,3-α) | OH | |
| 26-6 | N | (acetonide sugar with Me, Me, CH₂—L; 4D-1,4-β-2,3-α) | OH | |
| 27-4 | CH | —CH₂OCH₂CH₂—L | PO₃Na₂ | |
| 27-5 | CH | —CH₂OCH₂CH₂—L | PO₃Na₂ | |
| 27-6 | CH | —CH₂OCH₂CH₂—L | PO₃Na₂ | |
| 28-4 | CH | (sugar with OH, OH, CH₂—O—L; 4D-1,4-β-2,3-α) | PO₃Na₂ | |
| 28-5 | CH | (sugar with OH, OH, CH₂—O—L; 4D-1,4-β-2,3-α) | PO₃Na₂ | |
| 28-6 | CH | (sugar with OH, OH, CH₂—O—L; 4D-1,4-β-2,3-α) | PO₃Na₂ | |
| 29-4 | N | (sugar with HO, OH, CH₂—CH₂—L; 4D-1,4-β-2,3-α) | PO₃Na₂ | |
| 29-5 | N | (sugar with HO, OH, CH₂—CH₂—L; 4D-1,4-β-2,3-α) | PO₃Na₂ | |
| 29-6 | N | (sugar with HO, OH, CH₂—CH₂—L; 4D-1,4-β-2,3-α) | PO₃Na₂ | |

TABLE 2-continued

Compounds of the Formulae (4), (5) and (6)
(for how the Table 2 is constructed, cf. analogous explanations for Table 1)

|  |  |  |
|---|---|---|
| (4) | (5) | (6) |

| No. | A | G—L | L | Phys. data |
|---|---|---|---|---|
| 30-4 | CH | —CH₂OCH₂CH₂O—L | PO₃Na₂ | |
| 30-5 | CH | —CH₂OCH₂CH₂O—L | PO₃Na₂ | |
| 30-6 | CH | —CH₂OCH₂CH₂O—L | PO₃Na₂ | |
| 31-4 | CH | —CH₂CH₂CH₂CH₂CH₂—L | PO₃H₂ | |
| 31-5 | CH | —CH₂CH₂CH₂CH₂CH₂—L | PO₃H₂ | |
| 31-6 | CH | —CH₂CH₂CH₂CH₂CH₂—L | PO₃H₂ | |
| 32-4 | CH | —CH₂CH₂CH₂OCH₂—L | PO₃H₂ | |
| 32-5 | CH | —CH₂CH₂CH₂OCH₂—L | PO₃H₂ | |
| 32-6 | CH | —CH₂CH₂CH₂OCH₂—L | PO₃H₂ | |
| 33-4 | CH | —CH₂OCH₂CH₂OCH₂—L | PO₃H₂ | |
| 33-5 | CH | —CH₂OCH₂CH₂OCH₂—L | PO₃H₂ | |
| 33-6 | CH | —CH₂OCH₂CH₂OCH₂—L | PO₃H₂ | |
| 34-4 | CH | —CH₂OCH₂OCH₂—L | PO₃H₂ | |
| 34-5 | CH | —CH₂OCH₂OCH₂—L | PO₃H₂ | |
| 34-6 | CH | —CH₂OCH₂OCH₂—L | PO₃H₂ | |
| 35-4 | CH | —CH₂CH₂OCH₂—L | PO₃H₂ | |
| 35-5 | CH | —CH₂CH₂OCH₂—L | PO₃H₂ | |
| 35-6 | CH | —CH₂CH₂OCH₂—L | PO₃H₂ | |
| 36-4 | CH | —CH₂CH(Me)OCH₂—L | PO₃H₂ | |
| 36-5 | CH | —CH₂CH(Me)OCH₂—L | PO₃H₂ | |
| 36-6 | CH | —CH₂CH(Me)OCH₂—L | PO₃H₂ | |
| 37-4 | CH | —CH₂OCH(CH₂OH)CH₂CH₂—L | PO₃H₂ | |
| 37-5 | CH | —CH₂OCH(CH₂OH)CH₂CH₂—L | PO₃H₂ | |
| 37-6 | CH | —CH₂OCH(CH₂OH)CH₂CH₂—L | PO₃H₂ | |
| 38-4 | CH | —CH₂CH₂CH(CH₂OH)OCH₂—L | PO₃H₂ | |
| 38-5 | CH | —CH₂CH₂CH(CH₂OH)OCH₂—L | PO₃H₂ | |
| 38-6 | CH | —CH₂CH₂CH(CH₂OH)OCH₂—L | PO₃H₂ | |
| 39-4 | CH | —CH₂CH(CH₂OH)OCH₂—L | PO₃H₂ | |
| 39-5 | CH | —CH₂CH(CH₂OH)OCH₂—L | PO₃H₂ | |
| 39-6 | CH | —CH₂CH(CH₂OH)OCH₂—L | PO₃H₂ | |
| 40-4 | CH | —CH₂CH₂C(=CH₂)CH₂OCH₂—L | PO₃H₂ | |
| 40-5 | CH | —CH₂CH₂C(=CH₂)CH₂OCH₂—L | PO₃H₂ | |
| 40-6 | CH | —CH₂CH₂C(=CH₂)CH₂OCH₂—L | PO₃H₂ | |
| 41-4 | CH | —CH₂CH₂CH₂CH₂CH(CH₂Ph)—L | PO₃H₂ | |
| 41-5 | CH | —CH₂CH₂CH₂CH₂CH(CH₂Ph)—L | PO₃H₂ | |
| 41-6 | CH | —CH₂CH₂CH₂CH₂CH(CH₂Ph)—L | PO₃H₂ | |
| 42-4 | CH | —CH₂CH₂-(m-C₆H₄)-L | PO₃H₂ | |
| 42-5 | CH | —CH₂CH₂-(m-C₆H₄)-L | PO₃H₂ | |
| 42-6 | CH | —CH₂CH₂-(m-C₆H₄)-L | PO₃H₂ | |
| 43-4 | CH | —CH₂CH₂-(tetrahydronaphthyl)-L | PO₃H₂ | |
| 43-5 | CH | —CH₂CH₂-(tetrahydronaphthyl)-L | PO₃H₂ | |
| 43-6 | CH | —CH₂CH₂-(tetrahydronaphthyl)-L | PO₃H₂ | |
| 44-4 | CH | -(tetrahydrofuran-2,5-diyl)-CH₂CH₂-L, 1,4-β | PO₃H₂ | |
| 44-5 | CH | -(tetrahydrofuran-2,5-diyl)-CH₂CH₂-L, 1,4-β | PO₃H₂ | |
| 44-6 | CH | -(tetrahydrofuran-2,5-diyl)-CH₂CH₂-L, 1,4-β | PO₃H₂ | |
| 45-4 | CH | -(2,5-dihydrofuran-2,5-diyl)-CH₂CH₂-L, 1,4-β | PO₃H₂ | |
| 45-5 | CH | -(2,5-dihydrofuran-2,5-diyl)-CH₂CH₂-L, 1,4-β | PO₃H₂ | |
| 45-6 | CH | -(2,5-dihydrofuran-2,5-diyl)-CH₂CH₂-L, 1,4-β | PO₃H₂ | |
| 46-4 | CH | —CH₂CH₂CH₂CH₂CH₂—L | CO₂H | |
| 46-5 | CH | —CH₂CH₂CH₂CH₂CH₂—L | CO₂H | |
| 46-6 | CH | —CH₂CH₂CH₂CH₂CH₂—L | CO₂H | |
| 47-4 | CH | —CH₂OCH₂CH₂CH₂—L | CO₂H | |
| 47-5 | CH | —CH₂OCH₂CH₂CH₂—L | CO₂H | |
| 47-6 | CH | —CH₂OCH₂CH₂CH₂—L | CO₂H | |
| 48-4 | CH | —CH₂CH₂CH₂OCH₂—L | CO₂H | |
| 48-5 | CH | —CH₂CH₂CH₂OCH₂—L | CO₂H | |
| 48-6 | CH | —CH₂CH₂CH₂OCH₂—L | CO₂H | |
| 49-4 | CH | —CH₂OCH₂CH₂OCH₂—L | CO₂H | |

TABLE 2-continued

Compounds of the Formulae (4), (5) and (6)
(for how the Table 2 is constructed, cf. analogous explanations for Table 1)

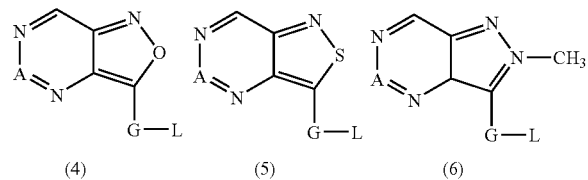

(4)   (5)   (6)

| No. | A | G—L | L | Phys. data |
|---|---|---|---|---|
| 49-5 | CH | —CH$_2$OCH$_2$CH$_2$OCH$_2$—L | CO$_2$H | |
| 49-6 | CH | —CH$_2$OCH$_2$CH$_2$OCH$_2$—L | CO$_2$H | |
| 50-4 | CH | —CH$_2$OCH$_2$OCH$_2$—L | CO$_2$H | |
| 50-5 | CH | —CH$_2$OCH$_2$OCH$_2$—L | CO$_2$H | |
| 50-6 | CH | —CH$_2$OCH$_2$OCH$_2$—L | CO$_2$H | |
| 51-4 | CH | —CH$_2$CH$_2$OCH$_2$—L | CO$_2$H | |
| 51-5 | CH | —CH$_2$CH$_2$OCH$_2$—L | CO$_2$H | |
| 51-6 | CH | —CH$_2$CH$_2$OCH$_2$—L | CO$_2$H | |
| 52-4 | CH | —CH$_2$CH(Me)OCH$_2$—L | CO$_2$H | |
| 52-5 | CH | —CH$_2$CH(Me)OCH$_2$—L | CO$_2$H | |
| 52-6 | CH | —CH$_2$CH(Me)OCH$_2$—L | CO$_2$H | |
| 53-4 | CH | —CH$_2$OCH(CH$_2$OH)CH$_2$CH$_2$—L | CO$_2$Na | |
| 53-5 | CH | —CH$_2$OCH(CH$_2$OH)CH$_2$CH$_2$—L | CO$_2$Na | |
| 53-6 | CH | —CH$_2$OCH(CH$_2$OH)CH$_2$CH$_2$—L | CO$_2$Na | |
| 54-4 | CH | —CH$_2$CH$_2$CH(CH$_2$OH)OCH$_2$—L | CO$_2$Na | |
| 54-5 | CH | —CH$_2$CH$_2$CH(CH$_2$OH)OCH$_2$—L | CO$_2$Na | |
| 54-6 | CH | —CH$_2$CH$_2$CH(CH$_2$OH)OCH$_2$—L | CO$_2$Na | |
| 55-4 | CH | —CH$_2$CH(CH$_2$OH)OCH$_2$—L | CO$_2$Na | |
| 55-5 | CH | —CH$_2$CH(CH$_2$OH)OCH$_2$—L | CO$_2$Na | |
| 55-6 | CH | —CH$_2$CH(CH$_2$OH)OCH$_2$—L | CO$_2$Na | |
| 56-4 | CH | —CH$_2$CH$_2$C(=CH$_2$)CH$_2$OCH$_2$—L | CO$_2$Na | |
| 56-5 | CH | —CH$_2$CH$_2$C(=CH$_2$)CH$_2$OCH$_2$—L | CO$_2$Na | |
| 56-6 | CH | —CH$_2$CH$_2$C(=CH$_2$)CH$_2$OCH$_2$—L | CO$_2$Na | |
| 56-4 | CH | —CH$_2$CH$_2$CH$_2$CH$_2$CH(CH$_2$Ph)—L | CO$_2$H | |
| 57-5 | CH | —CH$_2$CH$_2$CH$_2$CH$_2$CH(CH$_2$Ph)—L | CO$_2$H | |
| 57-6 | CH | —CH$_2$CH$_2$CH$_2$CH$_2$CH(CH$_2$Ph)—L | CO$_2$H | |
| 57-4 | CH | —CH$_2$CH$_2$—(3-phenylene)—L | CO$_2$H | |
| 57-5 | CH | —CH$_2$CH$_2$—(3-phenylene)—L | CO$_2$H | |
| 57-6 | CH | —CH$_2$CH$_2$—(3-phenylene)—L | CO$_2$H | |
| 58-4 | CH | —CH$_2$CH$_2$—(4-Me-phenylene)—L | CO$_2$H | |
| 58-5 | CH | —CH$_2$CH$_2$—(4-Me-phenylene)—L | CO$_2$H | |
| 58-6 | CH | —CH$_2$CH$_2$—(4-Me-phenylene)—L | CO$_2$H | |
| 59-4 | CH | —CH$_2$CH$_2$—(naphthyl)—L | CO$_2$H | |
| 59-5 | CH | —CH$_2$CH$_2$—(naphthyl)—L | CO$_2$H | |
| 59-6 | CH | —CH$_2$CH$_2$—(naphthyl)—L | CO$_2$H | |
| 60-4 | CH | —CH$_2$CH$_2$—(Br-tetrahydronaphthyl)—L | CO$_2$H | |
| 60-5 | CH | —CH$_2$CH$_2$—(Br-tetrahydronaphthyl)—L | CO$_2$H | |
| 60-6 | CH | —CH$_2$CH$_2$—(Br-tetrahydronaphthyl)—L | CO$_2$H | |
| 61-4 | CH | (tetrahydrofuran-2,5-diyl)—CH$_2$CH$_2$—L, 1,4-β | CO$_2$H | |
| 61-5 | CH | (tetrahydrofuran-2,5-diyl)—CH$_2$CH$_2$—L, 1,4-β | CO$_2$H | |

TABLE 2-continued

Compounds of the Formulae (4), (5) and (6)
(for how the Table 2 is constructed, cf. analogous explanations for Table 1)

| No. | A | G—L | L | Phys. data |
|---|---|---|---|---|
| 61-6 | CH | tetrahydrofuran-CH₂CH₂—L, 1,4-β | CO₂H | |
| 62-4 | CH | (OH, OH)-tetrahydrofuran-CH₂CH₂—L, 4D-1,4-β-2,3-α | CO₂Na | |
| 62-5 | CH | (OH, OH)-tetrahydrofuran-CH₂CH₂—L, 4D-1,4-β-2,3-α | CO₂Na | |
| 62-6 | CH | (OH, OH)-tetrahydrofuran-CH₂CH₂—L, 4D-1,4-β-2,3-α | CO₂Na | |
| 63-4 | N | (AcO, OAc)-tetrahydrofuran-CH₂—L, 4D-1,4-β-2,3-α | OAc | |
| 63-5 | N | (AcO, OAc)-tetrahydrofuran-CH₂—L, 4D-1,4-β-2,3-α | OAc | |
| 63-6 | N | (AcO, OAc)-tetrahydrofuran-CH₂—L, 4D-1,4-β-2,3-α | OAc | |
| 64-4 | C—SH | (HO, OH)-tetrahydrofuran-CH₂—L, 4D-1,4-β-2,3-α | OH | |
| 64-5 | C—SH | (HO, OH)-tetrahydrofuran-CH₂—L, 4D-1,4-β-2,3-α | OH | |
| 64-6 | C—SH | (HO, OH)-tetrahydrofuran-CH₂—L, 4D-1,4-β-2,3-α | OH | |
| 65-4 | C—SH | (HO, OH)-tetrahydrofuran-CH₂—L, 4D-1,2,3,4-β | OH | |
| 65-5 | C—SH | (HO, OH)-tetrahydrofuran-CH₂—L, 4D-1,2,3,4-β | OH | |
| 65-6 | C—SH | (HO, OH)-tetrahydrofuran-CH₂—L, 4D-1,2,3,4-β | OH | |
| 66-4 | C—SH | (HO, OH)-cyclopentane-CH₂—L, 1,4-β-2,3-α | OH | |
| 66-5 | C—SH | (HO, OH)-cyclopentane-CH₂—L, 1,4-β-2,3-α | OH | |
| 66-6 | C—SH | (HO, OH)-cyclopentane-CH₂—L, 1,4-β-2,3-α | OH | |

TABLE 2-continued

Compounds of the Formulae (4), (5) and (6)
(for how the Table 2 is constructed, cf. analogous explanations for Table 1)

| No. | A | G—L | L | Phys. data |
|---|---|---|---|---|
| 67-4 | C—SH | cyclopentane with HO, OH, OH and CH$_2$—L substituents; 1,2,3,4-β | OH | |
| 67-5 | C—SH | cyclopentane with HO, OH, OH and CH$_2$—L substituents; 1,2,3,4-β | OH | |
| 67-6 | C—SH | cyclopentane with HO, OH, OH and CH$_2$—L substituents; 1,2,3,4-β | OH | |
| 68-4 | C—SH | cyclopentane with HO, OH, OH and OCH$_2$—L substituents; 1,4-β-2,3-α | OH | |
| 68-5 | C—SH | cyclopentane with HO, OH, OH and OCH$_2$—L substituents; 1,4-β-2,3-α | OH | |
| 68-6 | C—SH | cyclopentane with HO, OH, OH and OCH$_2$—L substituents; 1,4-β-2,3-α | OH | |

B. FORMULATION EXAMPLES a) A dust is obtained by mixing 10 parts by weight of a compound (I) and 90 parts by weight of talc as inert substance and comminuting the mixture in a hammer mill.

b) A readily water-dispersible wettable powder is obtained by mixing 25 parts by weight of a compound (I), 64 parts by weight of kaolin-containing quartz as inert substance, 10 parts by weight of potassium ligninsulfonate and 1 part by weight of sodium oleoylmethyltaurinate as wetting agent and dispersant and grinding the mixture in a pinned-disk mill.

c) A readily water-dispersible dispersion concentrate is obtained by mixing 20 parts by weight of a compound (I) with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255 to more than 277° C.) and grinding the mixture in a bowl mill to a fineness of less than 5 microns.

d) An emulsifiable concentrate is obtained from 15 parts by weight of a compound (I), 75 parts by weight of cyclohexanone as solvent and 10 parts by weight of ethoxylated nonylphenol as emulsifier.

e) Water-dispersible granules are obtained by mixing
75 parts by weight of a compound (I),
10 parts by weight of calcium ligninsulfonate,
5 parts by weight of sodium lauryl sulfate,
3 parts by weight of polyvinyl alcohol and
7 parts by weight of kaolin,
grinding the mixture in a pinned-disk mill and granulating the powder in a fluidized bed by spraying on water as granulating liquid.

f) Water-dispersible granules are also obtained by homogenizing and precomminuting, in a colloid mill,
25 parts by weight of a compound (I),
5 parts by weight of 2,2'-dinaphthylmethane-6,6'-disulfonate,
2 parts by weight of sodium oleoylmethyltaurinate,
1 part by weight of polyvinyl alcohol,
17 parts by weight of potassium carbonate, and
50 parts by weight of water,
then grinding the mixture in a bead mill and atomizing and drying the resulting suspension in a spray tower by means of a single-substance nozzle.

C. BIOLOGICAL EXAMPLES

1. Spectral Photometric Enzyme Test

A) Test with AMPDA from Peas

In several experiments at different concentrations, the test substance was preincubated with in each case 0.01 enzyme units (U=units) of adenosine monophosphate deaminase (from peas) (J. Dancer et al., Plant Physiol., 114 (1997) 119) in 0.15 ml of an aqueous citrate buffer solution (0.06 M, pH 7.1 with 5 M NaOH), 0.01 g/ml of BSA (Bovine Serum Albumin, Albumin from bovine serum), 0.01 M KCl and 1 μM of diadenosine pentaphosphate. The enzyme reaction was started by adding an aqueous solution of 0.6 mM adenosine monophosphate and 1 mM adenosine triphosphate to the preincubated solution. After 60 min at 25° C., the reaction was terminated by addition of 100 μl of reagent 1 (=0.1 M phenol and 0.17 mM sodium nitrosylprussiate=Na$_2$-[Fe(CN)$_5$NO]) and 100 μl of reagent 2 (=0.125 M NaOH, 0.38 M Na$_2$HPO$_4$ and 5 ml HOCl in 500 ml of water). After 60 min at 55° C., the absorption at 625 nm was measured.

Comparison with the value which was obtained in the test without added test substance is an indication of the enzyme inhibition. In the test, compounds 28-1 and 44-1, for example, show at least 50% inhibition of the enzyme activity at a concentration of 500 μM.

B) Test with AMPDA from Calf Intestine

In several batches at different concentrations, the test substance was preincubated with in each case 0.04 enzyme units (U) of adenosine monophosphate deaminase (from calf intestine) in 2.1 ml of an aqueous citrate buffer solution (0.01 M, pH 6.1 with 2 M NaOH), 0.05 g/ml of BSA and 0.033 M KCl at 25° C. for 10 min. The enzyme reaction was started by adding 100 µl of an aqueous solution of 0.8 mM adenosine monophosphate to 700 µl of the preincubated solution. Spectrophotometric measurement of the absorption at 265 nm over a period of 2 min in comparison to a reference cuvette with 800 µl of the preincubated solution gave a value which, compared to the value obtained in the test without added test substance, was an indication of the enzyme inhibition. In the test, the compounds 28-1 and 44-1, for example, show at least 50% inhibition of the enzyme activity at a concentration of 500 µM.

C) Test with ADA from Rabbit Muscle

In several batches at different concentrations, the test substance was preincubated with in each case 0.04 enzyme units (U) of adenosine deaminase (from rabbit muscle) in 2.1 ml of an aqueous phosphate buffer solution (0.1 M, pH 7.5), at 25° C. for 10 min. The enzyme reaction was started by adding 100 µl of an aqueous solution of 0.8 mM adenosine to 700 µl of the preincubated solution. Spectrophotometric measurement of the absorption at 265 nm over a period of 2 min in comparison to a reference cuvette with 800 µl of the preincubated solution gave a value which, compared to the value obtained in the test without added test substance, was an indication of the enzyme inhibition. In the test, the compounds 1-1, 12-1, 21-3, 22-2 and 159-3, for example, show at least 50% inhibition of the enzyme activity at a concentration of 500 µM.

2. Pre-Emergence Effect on Weeds

Seeds or rhizome pieces of monocotyledonous and dicotyledonous weed plants are placed in sandy loam soil in plastic pots and covered with soil. The compounds (I), formulated in the form of wettable powders or emulsion concentrates, are then applied to the surface of the soil cover as an aqueous suspension or emulsion at an application rate of 600 to 800 l of water/ha (converted), in various dosages.

After the treatment, the pots are placed in a greenhouse and kept under good growth conditions for the weeds. After the test plants have emerged, the damage to the plants or the negative effects on the emergence are scored visually after a test period of 3 to 1 weeks by comparison with untreated controls. As shown by the test results, the compounds (I) have good herbicidal pre-emergence activity against a broad spectrum of weed grasses and broad-leaved weeds. In the test, the compound No. 17-1 (see Table 1), for example, shows good herbicidal activity against harmful plants such as Galium aparine, Matricaria inodora and Elymus repens (=*Agropyron repens*) in the pre-emergence method at an application rate of 3 kg or less of active substance per hectare. Similar results are obtained with other compounds from Tables 1 and 2, for example with compounds Nos. 1-1, 12-1, 21-3, 22-2, 28-1, 44-1 and 159-3.

3. Post-Emergence Effect on Weeds

Seeds or rhizome pieces of monocotyledonous and dicotyledonous weeds are placed in sandy loam soil in plastic pots, covered with soil and grown in a greenhouse under good growth conditions. Three weeks after sowing, the test plants are treated at the three-leaf stage. The compounds (I), formulated as wettable powders or as emulsion concentrates, are sprayed, at various dosages, onto the green parts of the plant at an application rate of 600 to 800 l of water/ha (converted). After the test plants have been in the greenhouse for about 3 to 1 weeks under optimum growth conditions, the effect of the preparations is scored visually by comparison with untreated controls. The compounds (I) also have good herbicidal post-emergence activity against a broad spectrum of economically important weed grasses and broad-leaved weeds. In the test, the compound No. 17-1 (see Table 1), for example, shows good herbicidal activity against harmful plants such as Echinochloa crus-galli, Stellaria media, Amaranthus retroflexus, Xanium orientale, Setaria viridis, Avena fatua, Matricaria inodora and Pharbitis purpurea when applied by the post-emergence method at an application rate of 3 kg or less of active substance per hectare. Similar results are obtained with other compounds from Tables 1 and 2, for example with the compounds Nos. 1-1, 12-1, 21-3, 22-2, 28-1, 44-1 and 159-3.

4. Action on Harmful Plants in Rice

Transplanted and sown rice and also typical rice weeds (gramineous and broad-leaved) are grown in closed plastic pots in a greenhouse to the three-leaf stage (*Echinochloa crus-galli* 1.5-leaf) under paddy rice conditions (depth of the water: 2-3 cm). This is followed by treatment with the compounds (I). For this purpose the formulated active compounds are suspended, dissolved or emulsified in water and applied by pouring them into the water around the test plants in different dosages.

After this treatment, the test plants are placed in a greenhouse under optimum growth conditions and are maintained under these conditions throughout the entire test period.

About three weeks after application, evaluation is carried out by visual scoring of the damage to the plants by comparison with untreated controls. The compounds (I) have very good herbicidal activity against harmful plants.

5. Tolerance by Crop Plants

In further greenhouse experiments, seeds of a relatively large number of crop plants and weeds are placed in sandy loam soil and covered with soil. Some of the pots are treated immediately as described under section 1, while the remainder are placed in the greenhouse until the plants have developed two to three true leaves, and then sprayed with various dosages of the compounds (I), as described in section 2. Four to five weeks after the application, and after the plants have remained in the greenhouse, visual scoring shows that the compounds according to the invention leave dicotyledonous crops such as, for example, soya, cotton, oilseed rape, sugarbeet and potatoes undamaged when employed pre- and post-emergence, even when high dosages of active compounds are used. Moreover, some substances also leave gramineous crops, for example barley, wheat, rye, sorghum species, corn or rice, unharmed. Some compounds (I) display high selectivity and are therefore suitable for controlling undesirable vegetation in agricultural crops.

What is claimed is:

1. A compound of the formula (I),

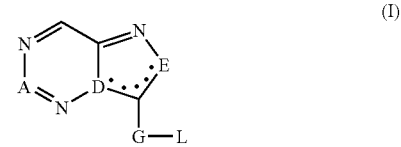

wherein:

A is a group of the formula C—R, where R is as defined further below,

D is a carbon atom or a nitrogen atom,

E a) when D is a nitrogen atom; E is also a nitrogen atom or a group of the formula C—R°, where R° is as defined further below, or
b) when D is a carbon atom, E is a group of the formula N—R°,
the line of dots (•••••) from D via an adjacent ring carbon atom to E is a double bond between the ring carbon atom and E if D is a nitrogen atom (case a), or
is a double bond between the ring carbon atom and D if D is a carbon atom (case b),
R is a hydrogen atom, amino, hydroxyl, mercapto, cyano, halogen, azido, nitro, $SF_5$, unsubstituted or substituted aminosulfonyl, acyl, acylamino, acyloxy, acylthio, mono- or di($C_1$-$C_4$)alkylamino, mono- or di($C_3$-$C_9$)cycloalkylamino, ($C_1$-$C_4$)alkylthio, ($C_2$-$C_4$)alkenylthio, $C_2$-$C_4$)alkynylthio, ($C_3$-$C_9$)cycloalkylthio, ($C_5$-$C_9$)cycloalkenylthio, ($C_1$-$C_4$)alkylsulfinyl, ($C_1$-$C_4$)alkylsulfonyl, ($C_1$-$C_4$)alkoxy, ($C_2$-$C_4$)alkenyloxy, ($C_2$-$C_4$)alkynyloxy, ($C_3$-$C_9$)cycloalkoxy, ($C_5$-$C_9$)cycloalkenyloxy, ($C_1$-$C_4$)alkyl, ($C_2$-$C_4$)alkenyl, ($C_2$-$C_4$)alkynyl, ($C_3$-$C_9$) cycloalkyl, ($C_5$-$C_9$)cycloalkenyl, ($C_1$-$C_4$)alkylaminosulfonyl or di(($C_1$-$C_4$)alkyl)aminosulfonyl, where each of the 23 last-mentioned radicals is unsubstituted or substituted in the hydrocarbon moiety by one or more radicals selected from the group consisting of halogen, hydroxyl, amino, nitro, formyl, carboxy, cyano, thiocyanato, ($C_1$-$C_4$)alkoxy, ($C_3$-$C_9$)cycloalkoxy, ($C_1$-$C_4$)haloalkoxy, ($C_1$-$C_4$)alkylthio, ($C_1$-$C_4$)haloalkylthio, mono($C_1$-$C_4$)alkylamino, di($C_1$-$C_4$)alkylamino, ($C_3$-$C_9$)cycloalkyl, ($C_3$-$C_9$)cycloalkylamino, (($C_1$-$C_4$)alkyl)carbonyl (($C_1$-$C_4$)alkoxy)carbonyl, aminocarbonyl, mono($C_1$-$C_4$)alkylaminocarbonyl and di($C_1$-$C_4$)alkylaminocarbonyl,
R° for the formula C—R° is a hydrogen atom, amino, hydroxyl, mercapto, cyano, halogen azido, nitro, $SF_5$, unsubstituted or substituted aminosulfonyl, acyl, acylamino, acyloxy, acylthio, mono- or di($C_1$-$C_4$)alkylamino, mono- or di($C_1$-$C_9$)cycloalkylamino, ($C_1$-$C_4$)alkylthio, ($C_1$-$C_4$)alkenylthio, $C_1$-$C_4$)alkynylthio, ($C_3$-$C_9$)cycloalkylthio, ($C_5$-$C_9$)cycloalkenylthio, ($C_1$-$C_4$)alkylsulfinyl, ($C_1$-$C_4$)alkylsulfonyl, ($C_1$-$C_4$)alkoxy, ($C_2$-$C_4$)alkenyloxy, ($C_2$-$C_4$)alkynyloxy, ($C_3$-$C_9$)cycloalkoxy, ($C_5$-$C_9$)cycloalkenyloxy, ($C_1C_4$)alkyl, ($C_2$-$C_4$)alkenyl, ($C_2$-$C_4$)alkynyl, ($C_3$-$C_9$) cycloalkyl, ($C_5$-$C_9$)cycloalkenyl ($C_1$-$C_4$)alkylaminosulfonyl or di(($C_1$-$C_4$)alkyl)aminosulfonyl, where each of the 23 last-mentioned radicals is unsubstituted or substituted in the hydrocarbon moiety by one or more radicals selected from the group consisting of halogen, hydroxyl, amino, nitro, formyl, carboxy, cyano, thiocyanato, ($C_1$-$C_4$)alkoxy, ($C_3$-$C_9$)cycloalkoxy—($C_1$-$C_4$)haloalkoxy, ($C_1$-$C_4$)alkylthio, ($C_1$-$C_4$)haloalkylthio, mono($C_1$-$C_4$)alkylamino, di($C_1$-$C_4$)alkylamino, ($C_3$-$C_9$)cycloalkyl, ($C_3$-$C_9$)cycloalkylamino, (($C_1$-$C_4$)alkyl)carbonyl, (($C_1$-$C_4$)alkoxy)carbonyl, aminocarbonyl, mono($C_1$-$C_4$)alkylaminocarbonyl and di($C_1C_4$)alkylaminocarbonyl,
R° for the formula N—R° is a hydrogen atom, amino, hydroxyl, mercapto, unsubstituted or substituted aminosulfonyl, acyl, acylamino, acyloxy, acylthio, mono- or di($C_1$-$C_4$)alkylamino, mono- or di($C_3$-$C_9$)cycloalkylamino, ($C_1$-$C_4$)alkylthio, ($C_2$-$C_4$)alkenylthio, $C_2$-$C_4$)alkynylthio, ($C_3$-$C_9$)cycloalkylthio, ($C_1$-$C_9$)cycloalkenylthio, ($C_1$-$C_4$)alkylsulfinyl, ($C_1$-$C_4$)alkylsulfonyl, ($C_1$-$C_4$)alkoxy, ($C_1$-$C_4$)alkenyloxy, ($C_2$-$C_4$)alkynyloxy, ($C_3$-$C_9$)cycloalkoxy, ($C_3$-$C_9$)cycloalkenyloxy, ($C_1$-$C_4$)alkyl, ($C_2$-$C_4$)alkenyl, ($C_2$-$C_4$)alkynyl ($C_3$-$C_9$)cycloalkyl, ($C_5$-$C_9$)cycloalkenyl, ($C_1$-$C_4$)alkylaminosulfonyl or di(($C_1$-$C_4$)alkyl)aminosulfonyl, where each of the 18 last-mentioned radicals is unsubstituted or substituted in the hydrocarbon moiety by one or more radicals selected from the group consisting of halogen, hydroxyl, amino, nitro, formyl, carboxy, cyano, thiocyanato, ($C_1$-$C_4$)alkoxy, ($C_3$-$C_9$)cycloalkoxy, ($C_1$-$C_4$)haloalkoxy, ($C_1$-$C_4$)alkylthio, ($C_1$-$C_4$)haloalkylthio, mono($C_1$-$C_4$)alkylamino, di($C_1$-$C_4$)alkylamino, ($C_3$-$C_9$)cycloalkyl, ($C_3$-$C_9$)cycloalkylamino, (($C_1$-$C_4$)alkyl)carbonyl, (($C_1$-$C_4$)alkoxy)carbonyl, aminocarbonyl, mono($C_1$-$C_4$)alkylaminocarbonyl and di($C_1$-$C_4$)alkylaminocarbonyl,
G is a divalent straight-chain saturated or unsaturated hydrocarbon linking bridge moiety having 4 to 6 carbon atoms in the chain, in which one or more chain carbons, in each case independently of one another, can be replaced by —O—, —S—, —NH—, ($C_1$-$C_4$)alkyl-N or acyl-N or, in the unsaturated case, one or more CH groups can in each case be replaced by a nitrogen atom, where the bridge in question is unsubstituted or
(a) is substituted by one or more identical or different radicals selected from the group consisting of halogen, nitro, radicals of the formula $R^1$ which are different from hydrogen, radicals of the formula $R^2R^3C=$ and radicals of the formula L*, where $R^1$, $R^2$, $R^3$ and L* are as defined further below,
(b) carries two or four substituents defined by the radical of formula $R^1$, of which in each case two together with the linking bridge moiety form a carbocyclic or heterocyclic ring having 3 to 7 ring atoms, where in the case of a heterocycle the number of heteroatoms is from 1 to 3 heteroatoms and are selected from the group consisting of O and S and where the ring in question may also have fused-on rings and is otherwise unsubstituted or substituted by one or more identical or different radicals selected from the group consisting of halogen, nitro, radicals of the formula $R^1$ which are different from hydrogen, radicals of the formula L* and oxo, where $R^1$ and L* are as defined further below,
(c) is linked cyclically with L via a second direct bond or via a heteroatom selected from the group consisting of O and S,
(d) has two or more substituents from the above groups (a) to (c) together,
L, L* independently or one another are each $OR^4$, $SR^4$, CN, $C(OR^5)(OR^6)OR^7$), —O—$Z^2$ or —NH-$Z^2$, where $R^4$, $R^5$, $R^6$, $R^7$ and $Z^2$ are as defined further below and where L may be attached to the bridge G via a second direct bond or via a heteroatom selected from the group consisting of O and S to form a ring,
$Z^2$ is a radical of the formula $COOR^8$, CS—$OR^8$, CO—$SR^8$, CS—$SR^8$, CO—$NR^9$—$SO_2$—$R^8$, CO—$NR^{10}R^{11}$, CS—$NR^{10}R^{11}$, CO—$R^{12}$, CS—$R^{12}$, SO—$R^{12}$,$SO_2R^{12}$, $SO_3R^8$, $SO_2NR^{10}R^{11}$, $SO_2NR^9COR^{12}$, $SO_2NR^9COOR^{12}$, P(=O)($OR^{13}$)($OR^{14}$), P(=S)($OR^{13}$)($OR^{14}$), or P(=O)($R^{11}$)($O^{14}$), P(=O)($OR^{13}$)($NR^{10}OR^{11}$), P(=O)($R^{10}R^{11}$)-($NR^{16}R^{17}$), P(=S)($OR^{13}$)($NR^{10}R^{11}$) or P(=S)($NR^{10}R^{11}$)($NR^{16}R^{17}$),
$R^1$ to $R^{17}$ independently of one another are each a hydrogen atom, ($C_1$-$C_6$)alkyl, ($C_2$-$C_6$)alkenyl, ($C_2$-$C_6$)alkynyl, ($C_3$-$C_9$)cycloalkyl, ($C_5$-$C_9$)cycloalkenyl, phenyl, where each of the last-mentioned carbon-containing radicals is unsubstituted or substituted by one or more radicals selected from the group consisting of amino, hydroxyl, mercapto, cyano, halogen, azido, nitro, $SF_5$, aminosulfonyl, acyl, acylamino, acyloxy, acylthio, (($C_1$-$C_4$)alkoxy)carbonyl, mono($C_1$-$C_4$)alkylamino, mono($C_3$-$C_9$)cycloalkylamino, di($C_1$-$C_4$)alkylamino, ($C_1$-$C_4$)alkylthio, ($C_2$-$C_4$)alkenylthio, ($C_2$-$C_4$)alkynylthio, ($C_3$-$C_9$)cycloalkylthio, ($C_5$-$C_9$)cycloalkenylthio, ($C_1$-$C_4$)alkylsulfinyl, ($C_1$-$C_4$)alkylsulfonyl, ($C_1$-$C_4$)alkoxy, ($C_2$-$C_4$)alkenyloxy, ($C_2$-$C_4$)alkynyloxy, ($C_3$-$C_9$)cycloalkoxy, ($C_5$-$C_9$)cycloalkenyloxy, ($C_3$-$C_9$)cycloalkyl, ($C_5$-$C_9$)cycloalkenyl, phenyl, substituted phenyl, and, in the case of cyclic radicals, also by ($C_1$-$C_4$)alkyl, ($C_2$-$C_4$)alkenyl, ($C_2$-$C_4$)alkynyl, ($C_1$-$C_4$) haloalkyl, ($C_2$-$C_4$)haloalkenyl, ($C_2$-$C_4$)haloalkynyl, ($C_1$-$C_4$)hydroxyalkyl and ($C_1$-$C_4$)alkoxy($C_1$-$C_4$)alkyl, its tautomers, its salts or its water addition product, except for the compound of the formula (I) in which A=CH, D=C, E=NH and G—L=β-D-ribofuranosyl.

2. The compound as claimed in claim 1, wherein:

A is a group of the formula C—R, where R is as defined further below,

D is a carbon atom or a nitrogen atom,

E a) when D is a nitrogen atom; E is also a nitrogen atom or a group of the formula C—R°, where R° is as defined further below, or b) when D is a carbon atom, E is a group of the formula N—R°, the line of dots (•••••) from D via an adjacent ring carbon atom to E is a double bond between the ring carbon atom and E if D is a nitrogen atom (case a), or is a double bond between the ring carbon atom and D if D is a carbon atom (case b), R is a hydrogen atom, amino, hydroxyl, mercapto, cyano, halogen, mono- or di($C_1$-$C_4$)alkylamino, ($C_1$-$C_4$)alkylthio, or ($C_1$-$C_4$)alkyl, R° for the formula C—R° is a hydrogen atom, amino, hydroxyl, mercapto, cyano, halogen, mono- or di($C_1$-$C_4$)alkylamino, ($C_1$-$C_4$)alkylthio, or ($C_1$-$C_4$)alkyl, R° for the formula N—R° is a hydrogen atom, amino, hydroxyl, mercapto, mono- or di($C_1$-$C_4$)alkylamino, ($C_1$-$C_4$)alkylthio, or ($C_1$-$C_4$)alkyl, G is a divalent straight-chain saturated hydrocarbon bridge having 4 to 6 carbon atoms in the chain, in which one or more chain carbons, in each case independently of one another, can be replaced by O, where the bridge in question is unsubstituted or (a) is substituted by one or more identical or different radicals of the formula $R^1$ which are different from hydrogen, (b) carries two or four substituents defined by the radical of formula $R^1$ or L*, of which in each case two together with the linking bridge moiety form a heterocyclic ring having 5 ring atoms and contains one oxygen heteroatom, L is $OR^4$, $SR^4$, —O—$Z^2$ or —NH—$Z^2$, L* is —$OR^4$, —$SR^4$, —O—$Z^2$ or —NH—$Z^2$, $Z^2$ is a radical of the formula $COOR^8$, $P(=O)(OR^{13})(OR^{14})$, or $P(=O)(R^{15})(O^{14})$, $R^1$, $R^4$, $R^8$, $R^{13}$, $R^{14}$ and $R^{14}$ are independently selected from a hydrogen atom or ($C_1$-$C_6$)alkyl which is optionally substituted with hydroxyl, its tautomers, its salts or its water addition product, except for the compound of the formula (I) in which A=CH, D=C, E=NH and G—L=β-D-ribofuranosyl.

3. The compound as claimed in claim 2, wherein in the compound of formula (I)

G is a divalent straight-chain saturated hydrocarbon bridge having 4 to 6 carbon atoms in the chain, in which one or more chain carbons, in each case independently of one another, can be replaced by —O— where the bridge in question is unsubstituted or (a) is substituted by one or more identical or different radicals of the formula $R^1$ which are different from hydrogen.

4. The compound as claimed in claim 2, wherein

G is a divalent straight-chain saturated hydrocarbon bridge having 4 to 6 carbon atoms in the chain, in which one or more chain carbons, in each case independently of one another, can be replaced by —O— where the bridge in question is unsubstituted or (b) carries two or four substituents defined by the radical of formula $R^1$, of which in each case two together with the linking bridge moiety form a heterocyclic ring having 5 ring atoms and contains one oxygen heteroatom.

5. The compound as claimed in claim 2, wherein

L is —$OR^4$ or —O—$Z^2$;

L* is —$OR^4$ or —O—$Z^2$.

6. The compound of claim 1, wherein:

G is a divalent straight-chain saturated or unsaturated hydrocarbon linking bridge moiety having 4 to 6 carbon atoms in the chain, in which one or more chain carbons, in each case independently of one another, can be replaced by —O—, —S—, —NH—, ($C_1$-$C_4$) alkyl-N or acyl-N or, in the unsaturated case, one or more CH groups can in each case be replaced by a nitrogen atom, where the bridge in question is unsubstituted or (a) is substituted by one or more identical or different radicals selected from the group consisting of halogen, nitro, radicals of the formula $R^1$ which are different from hydrogen, radicals of the formula $R^2R^3C=$ and radicals of the formula L*, (b) carries two or four substituents defined by the radical of formula $R^1$, of which in each case two together with the linking bridge moiety form a carbocyclic or heterocyclic ring having 3 to 7 ring atoms, where in the case of a heterocycle the number of heteroatoms is from 1 to 3 heteroatoms and are selected from the group consisting of O and S and is otherwise unsubstituted or substituted by one or more identical or different radicals selected from the group consisting of halogen, nitro, radicals of the formula $R^1$ which are different from hydrogen, radicals of the formula L* and oxo.

7. The compound of claim 6, wherein:

G is a divalent straight-chain saturated or unsaturated hydrocarbon linking bridge moiety having 4 to 6 carbon atoms in the chain, in which one or more chain carbons, in each case independently of one another, can be replaced by —O—, —S—, —NH—, ($C_1$-$C_4$) alkyl-N or acyl-N or, in the unsaturated case, one or more CH groups can in each case be replaced by a nitrogen atom, where the bridge in question is unsubstituted or (a) is substituted by one or more identical or different radicals selected from the group consisting of halogen, nitro, radicals of the formula $R^1$ which are different from hydrogen and radicals of the formula L*, (b) carries two or four substituents defined by the radical of formula $R^1$, of which in each case two together with the linking bridge moiety form a carbocyclic or heterocyclic ring having 5 to 6 ring atoms, where in the case of a heterocycle the number of heteroatoms is 1 heteroatom and is selected from the group consisting of O and S and is otherwise unsubstituted or substituted by one or more identical or different radicals selected from the group consisting of halogen, nitro, radicals of the formula $R^1$ which are different from hydrogen, radicals of the formula L* and oxo.

8. A herbicidal or plant-growth-regulating composition, comprising one or more compounds of the formula (I), their salts, their tautomers or their water addition products as set forth in claim 1 and formulation auxiliaries which are customary in crop protection.

9. A method of making a composition for controlling harmful plants and for regulating the growth of plants which comprises mixing an effective amount of a compound of the formula (I), its salt, its tautomer or its water addition product as set forth in claim 1 as herbicide or plant growth regulator with a herbicidally acceptable carrier.

10. The method as claimed in claim 9, wherein the compound of the formula (I), its salt, its tautomer or its water addition product is employed for controlling harmful plants or for regulating the growth of crop plants or ornamental plants.

11. The method as claimed in claim 10, wherein the crop plants are transgenic crop plants.

12. A method for inhibiting adenosine monophosphate deaminase (AMPDA) or adenosine deaminase (ADA) of plants to provide herbicidal effects which comprises applying compound of the formula (I), its tautomer, its salt or its water addition product,

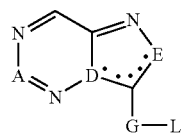

(I)

where in formula (I)

A is a group of the formula C—R, where R is as defined further below,

D is a carbon atom or a nitrogen atom,

E a) when D is a nitrogen atom, E is also a nitrogen atom or a group of the formula C—R°, where R° is as defined further below, or b) when D is a carbon atom, E is a group of the formula N—R° the line of dots (•••••) from D via an adjacent ring carbon atom to E is a double bond between the ring carbon atom and E if D is a nitrogen atom (case a), or is a double bond between the ring carbon atom and D if D is a carbon atom (case b), R is a hydrogen atom, amino, hydroxyl, mercapto, cyano, halogen, azido, nitro, $SF_5$, unsubstituted or substituted aminosulfonyl, acyl, acylamino, acyloxy, acylthio, mono- or di($C_1$-$C_4$)alkylamino, mono- or di($C_3$-$C_9$)cycloalkylamino, ($C_1$-$C_4$)alkylthio, ($C_2$-$C_4$)alkenylthio, $C_2$-$C_4$)alkynylthio, ($C_3$-$C_9$)cycloalkylthio, ($C_5$-$C_9$)cycloalkenylthio, ($C_1$-$C_4$)alkylsulfinyl, ($C_1$-$C_4$)alkylsulfonyl, ($C_1$-$C_4$)alkoxy, ($C_2$-$C_4$)alkenyloxy, ($C_2$-$C_4$)alkynyloxy, ($C_3$-$C_9$)cycloalkoxy, ($C_5$-$C_9$)cycloalkenyloxy, ($C_1$-$C_4$)alkyl, ($C_2$-$C_4$)alkenyl, ($C_2$-$C_4$)alkynyl, ($C_3$-$C_9$) cycloalkyl, ($C_5$-$C_9$)cycloalkenyl, ($C_1$-$C_4$)alkylaminosulfonyl or di(($C_1$-$C_4$)alkyl)aminosulfonyl, where each of the 23 last-mentioned radicals is unsubstituted or substituted in the hydrocarbon moiety by one or more radicals selected from the group consisting of halogen, hydroxyl, amino, nitro, formyl, carboxy, cyano, thiocyanato, ($C_1$-$C_4$)alkoxy, ($C_3$-$C_9$)cycloalkoxy, ($C_1$-$C_4$)haloalkoxy, ($C_1$-$C_4$)alkylthio, ($C_1$-$C_4$)haloalkylthio, mono($C_1$-$C_4$)alkylamino, di($C_1$-$C_4$)alkylamino, ($C_3$-$C_9$)cycloalkyl, ($C_3$-$C_9$)cycloalkylamino, (($C_1$-$C_4$)alkyl)carbonyl, (($C_1$-$C_4$) alkoxy)carbonyl, aminocarbonyl, mono($C_1$-$C_4$)alkylaminocarbonyl and di($C_1$-$C_4$)alkylaminocarbonyl, R° for the formula C—R° is a hydrogen atom, amino, hydroxyl, mercapto, cyano, halogen, azido, nitro, $SF_5$, unsubstituted or substituted aminosulfonyl, acyl, acylamino, acyloxy, acylthio, mono- or di($C_1$-$C_4$)alkylamino, mono- or di($C_3$-$C_9$)cycloalkylamino, ($C_1$-$C_4$) alkylthio, ($C_2$-$C_4$)alkenylthio, $C_2$-$C_4$)alkynylthio, ($C_3$-$C_9$)cycloalkylthio, ($C_5$-$C_9$)cycloalkenylthio, ($C_1$-$C_4$) alkylsulfinyl, ($C_{1-4}$)alkylsulfonyl, ($C_1$C—$C_4$)alkoxy, $C_2$-$C_4$)alkenyloxy, ($C_2$-$C_4$)alkynyloxy, ($C_3$-$C_9$)cycloalkoxy, ($C_5$-$C_9$)cycloalkenyloxy, ($C_1$-$C_4$)alkyl, ($C_2$-$C_4$)alkenyl, ($C_3$-$C_9$) cycloalkyl, ($C_5$-$C_9$)cycloalkenyl ($C_1$-$C_4$)alkylaminosulfonyl or di(($C_1$-$C_4$)alkyl)aminosulfonyl, where each of the 23 last-mentioned radicals is unsubstituted or substituted in the hydrocarbon moiety by one or more radicals selected from the group consisting of halogen, hydroxyl, amino, nitro, formyl, carboxy, cyano, thiocyanato, ($C_1$-$C_4$)alkoxy, ($C_3$$C_9$) cycloalkoxy, ($C_1$-$C_4$)haloalkoxy, ($C_1$-$C_4$)alkylthio, ($C_1$-$C_4$)haloalkylthio, mono($C_1$-$C_4$)alkylamino, di($C_1$-$C_4$)alkylamino, ($C_3$-$C_9$)cycloalkyl, ($C_3$-$C_9$)cycloalkylamino, (($C_1$-$C_4$)alkyl)carbonyl, (($C_1$-$C_4$)alkoxy)carbonyl, aminocarbonyl, mono($C_1$-$C_4$)alkylaminocarbonyl and di($C_1$-$C_4$)alkylaminocarbonyl, R° for the formula N—R° is a hydrogen atom, amino, hydroxyl, mercapto, unsubstituted or substituted aminosulfonyl, acyl, acylamino, acyloxy, acylthio, mono- or di($C_1$-$C_4$)alkylamino, mono- or di($C_3$-$C_9$)cycloalkylamino, ($C_1$-$C_4$)alkylthio, ($C_2$-$C_4$)alkenylthio, $C_2$-$C_4$) alkynylthio, ($C_3$-$C_9$)cycloalkylthio, ($C_5$-$C_9$)cycloalkenylthio, ($C_1$-$C_4$)alkylsulfinyl, ($C_1$-$C_4$)alkylsulfonyl, ($C_1$-$C_4$)alkoxy, ($C_2$-$C_4$)alkenyloxy, ($C_2$-$C_4$)alkynyloxy, ($C_3$-$C_9$)cycloalkoxy ($C_5$-$C_9$)cycloalkenyloxy ($C_1$-$C_4$) alkyl, ($C_2$-$C_4$)alkenyl, ($C_2$-$C_4$)alkynyl, ($C_3$-$C_9$)cycloalkyl, ($C_5$-$C_9$)cycloalkenyl, ($C_1$-$C_4$)alkylaminosulfonyl or di(($C_1$-$C_4$)alkyl)aminosulfonyl, where each of the 18 last-mentioned radicals is unsubstituted or substituted in the hydrocarbon moiety by one or more radicals selected from the group consisting of halogen, hydroxyl, amino, nitro, formyl, carboxy, cyano, thiocyanato, ($C_1$-$C_4$)alkoxy ($C_3$-$C_9$)cycloalkoxy ($C_1$-$C_4$) haloalkoxy, ($C_1$-$C_4$)alkylthio, ($C_{1-4}$)haloalkylthio, mono($C_1$-$C_4$)alkylamino, di($C_1$-$C_4$)alkylamino, ($C_1$-$C_4$)cycloalkyl, ($C_{3-9}$)cycloalkylamino, (($C_1$-$C_4$)alkyl) carbonyl, (($C_1$-$C_4$)alkoxy)carbonyl, aminocarbonyl mono($C_1$-$C_4$)alkylaminocarbonyl and di($C_1$-$C_4$)alkylaminocarbonyl, G is a divalent straight-chain saturated or unsaturated hydrocarbon linking bridge moiety having 4 to 6 carbon atoms in the chain, in which one or more chain carbons, in each case independently of one another, can be replaced by —O—, —S—, —NH—, ($C_1$-$C_4$) alkyl-N or acyl-N or, in the unsaturated case, one or more CH groups can in each case be replaced by a nitrogen atom, where the bridge in question is unsubstituted or (a) is substituted by one or more identical or different radicals selected from the group consisting of halogen, nitro, radicals of the formula $R^1$ which are different from hydrogen, radicals of the formula R²R³C= and radicals of the formula L*, where R¹, R², R³ and L* are as defined further below,
(b) carries two or four substituents defined by the radical of formula R¹, of which in each case two together with the linking bridge moiety form a carbocyclic or heterocyclic ring having 3 to 7 ring atoms, where in the case of a heterocycle the number of heteroatoms is from 1 to 3 heteroatoms and are selected from the group consisting of O and S and where the ring in question may also have fused-on rings and is otherwise unsubstituted or substituted by one or more identical or different radicals selected from the group consisting of halogen, nitro, radicals of the formula R¹ which are different from hydrogen, radicals of the formula L* and oxo, where R¹ and L* are as defined further below,
(c) is linked cyclically with L via a second direct bond or via a heteroatom selected from the group consisting of O and S,
(d) has two or more substituents from the above groups (a) to (c) together,
L, L* independently or one another are each OR⁴, SR⁴, CN, C(OR⁵)(OR⁶)OR⁷, —O—Z² or —NH—Z², where R⁴, R⁵, R⁶, R⁷ and Z² are as defined further below and where L may be attached to the bridge G via a second direct bond or via a heteroatom selected from the group consisting of O and S to form a ring,
Z² is a radical of the formula COOR⁸, CS—OR⁸, CO—SR⁸, CS—SR⁸, CO—NR⁹—SO₂—R⁸, CO—NR¹⁰R¹¹, CS—NR¹⁰R¹¹, CO—R¹², CS—R¹², SO—R¹², SO₂R¹², SO₃R⁸, SO₂NR¹⁰R¹¹, SO₂NR⁹COR¹², SO₂NR⁹COOR¹², P(=O)(OR¹³)(OR¹⁴), P(=S)(OR¹³)(OR¹⁴), P(=O)(R¹⁵)(OR¹⁴), P(=O)(OR¹³)(NR¹⁰R¹¹), P(=O)(R¹⁰R¹¹)-(NR¹⁶R¹⁷), P(=S)(OR¹³)(NR¹⁰R¹¹) or P(=S)(NR¹⁰R¹¹)(NR¹⁶R¹⁷),
R¹ to R¹⁷ independently of one another are each a hydrogen atom, (C₁-C₆)alkyl, (C₂-C₆)alkenyl, (C₂-C₆)alkynyl, (C₃-C₉)cycloalkyl, (C₅-C₉)cycloalkenyl, or phenyl, where each of the last-mentioned carbon-containing radicals is unsubstituted or substituted by one or more radicals selected from the group consisting of amino, hydroxyl, mercapto, cyano, halogen, azido, nitro, SF₅, aminosulfonyl, acyl, acylamino, acyloxy, acylthio, C₁-C₄alkoxy)carbonyl, mono(C₁-C₄)alkylamino, mono(C₃-C₉)cycloalkylamino, di(C₁-C₄)alkylamino, (C₁-C₄)alkylthio, (C₂-C₄)alkenylthio, (C₂-C₄)alkynylthio, (C₃-C₉)cycloalkylthio, (C₅-C₉)cycloalkenylthio, (C₁-C₄)alkylsulfinyl, (C₁-C₄)alkylsulfonyl, (C₁-C₄)alkoxy, (C₂-C₄)alkenyloxy, (C₂-C₄)alkynyloxy, (C₃-C₉)cycloalkoxy, (C₅-C₉)cycloalkenyloxy, (C₃-C₉)cycloalkyl, (C₅-C₉)cycloalkenyl, phenyl, substituted phenyl, and, in the case of cyclic radicals, also by (C₁-C₄)alkyl, (C₂-C₄)alkenyl, (C₂-C₄)alkynyl, (C₁-C₄)haloalkyl, (C₂-C₄)haloalkenyl, (C₂-C₄)haloalkynyl, (C₁-C₄)hydroxyalkyl and (C₁-C₄)alkoxy(C₁-C₄)alkyl,
to the enzyme AMPDA of plants or enzyme ADA of plants.

13. A method for controlling harmful plants or for regulating the growth of plants, which comprises applying an effective amount of one or more compounds of the formula (I), their salts, their tautomers or their water addition products as set forth in claim 12 onto the plants, parts of plants, plant seeds or the area under cultivation.

14. The method of claim 12, wherein:
G is a divalent straight-chain saturated or unsaturated hydrocarbon linking bridge moiety having 4 to 6 carbon atoms in the chain, in which one or more chain carbons, in each case independently of one another, can be replaced by —O—, —S—, —NH—, (C₁-C₄)alkyl-N or acyl-N or, in the unsaturated case, one or more CH groups can in each case be replaced by a nitrogen atom, where the bridge in question is unsubstituted or
(a) is substituted by one or more identical or different radicals selected from the group consisting of halogen, nitro, radicals of the formula R¹ which are different from hydrogen, radicals of the formula R²R³C= and radicals of the formula L*,
(b) carries two or four substituents defined by the radical of formula R¹, of which in each case two together with the linking bridge moiety form a carbocyclic or heterocyclic ring having 3 to 7 ring atoms, where in the case of a heterocycle the number of heteroatoms is from 1 to 3 heteroatoms and are selected from the group consisting of O and S and is otherwise unsubstituted or substituted by one or more identical or different radicals selected from the group consisting of halogen, nitro, radicals of the formula R¹ which are different from hydrogen, radicals of the formula L* and oxo.

15. The method of claim 14, wherein:
G is a divalent straight-chain saturated or unsaturated hydrocarbon linking bridge moiety having 4 to 6 carbon atoms in the chain, in which one or more chain carbons, in each case independently of one another, can be replaced by —O—, —S—, —NH—, (C₁-C₄)alkyl-N or acyl-N or, in the unsaturated case, one or more CH groups can in each case be replaced by a nitrogen atom, where the bridge in question is unsubstituted or
(a) is substituted by one or more identical or different radicals selected from the group consisting of halogen, nitro, radicals of the formula R¹ which are different from hydrogen and radicals of the formula L*,
(b) carries two or four substituents defined by the radical of formula R¹, of which in each case two together with the linking bridge moiety form a carbocyclic or heterocyclic ring having 5 to 6 ring atoms, where in the case of a heterocycle the number of heteroatoms is 1 heteroatom and is selected from the group consisting of O and S and is otherwise unsubstituted or substituted by one or more identical or different radicals selected from the group consisting of halogen, nitro, radicals of the formula R¹ which are different from hydrogen, radicals of the formula L* and oxo.

16. A method for inhibiting adenosine monophosphate deaminase (AMPDA) or adenosine deaminase (ADA) of plants to provide herbicidal effects which comprises administering to plants a compound of the formula (I), its tautomer, its salt or its water addition product,

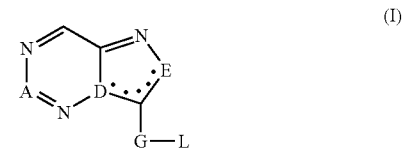

where in formula (I)
A is a group of the formula C—R, where R is as defined further below,
D is a carbon atom or a nitrogen atom, E a) when D is a nitrogen atom; E is also a nitrogen atom or a group of the formula C—R°, where R° is as defined further below, or b) when D is a carbon atom, E is a group of the formula N—R° the line of dots (•••••) from D via an adjacent ring carbon atom to E is a double bond between the ring carbon atom and E if D is a nitrogen atom (case a), or is a double bond between the ring carbon atom and D if D is a carbon atom (case b), R is a hydrogen atom, amino, hydroxyl, mercapto, cyano, halogen, mono- or di($C_1$-$C_4$)alkylamino, ($C_1$-$C_4$)alkylthio, or ($C_1$-$C_4$)alkyl, R° for the formula C—R° is a hydrogen atom, amino, hydroxyl, mercapto, cyano, halogen, mono- or di($C_1$-$C_4$)alkylamino, ($C_{1-4}$)alkylthio, or ($C_1C$-$C_4$)alkl, R° for the formula N—R° is a hydrogen atom, amino, hydroxyl, mercapto, mono- or di($C_1$-$C_4$)alkylamino, ($C_1$-$C_4$)alkylthio, or ($C_1$-$C_4$)alkyl, G is a divalent straight-chain saturated hydrocarbon linking bridge moiety having 4 to 6 carbon atoms in the chain, in which one or more chain carbons, in each case independently of one another, can be replaced by —O— where the bridge in question is unsubstituted or (a) is substituted by one or more identical or different radicals of the formula $R^1$ which are different from hydrogen, (b) carries two or four substituents defined by the radical of formula $R^1$ or L*, of which in each case two together with the linking bridge moiety form a heterocyclic ring having 5 ring atoms and contains one oxygen heteroatom, L is —$OR^4$, —$SR^4$, —O—$Z^2$ or —NH—$Z^2$, L* is —$OR^4$, —$SR^4$, —$OZ^2$ or —NH-$Z^2$, $Z^2$ is a radical of the formula $COOR^8$, $P(=O)(OR^{13})(OR^{14})$, or $P(=O)(R^{15})(OR^{14})$ $R^1$, $R^4$, $R^8$, $R^{13}$, $R^{14}$ and $R^{15}$ are independently selected from a hydrogen atom or ($C_1$-$C_6$)alkyl which is optionally substituted with hydroxyl, to inhibit the enzyme AMPDA of plants or the enzyme ADA of plants.

17. The method as claimed in claim 16, wherein in the compound of formula (1)

G is a divalent straight-chain saturated hydrocarbon bridge having 4 to 6 carbon atoms in the chain, in which one or more chain carbons, in each case independently of one another, can be replaced by —O— where the bridge in question is unsubstituted or (a) is substituted by one or more identical or different radicals of the formula $R^1$ which are different from hydrogen.

18. The method as claimed in claim 16, wherein

G is a divalent straight-chain saturated hydrocarbon bridge having 4 to 6 carbon atoms in the chain, in which one or more chain carbons, in each case independently of one another, can be replaced by —O— where the bridge in question is unsubstituted or (b) carries two or four substituents defined by the radical of formula L*, of which in each case two together with the linking bridge moiety form a heterocyclic ring having 5 ring atoms and contains one oxygen heteroatom.

19. The method as claimed in claim 16, wherein

L is —$OR^4$ or —O—$Z^2$;

L* is —$OR^4$ or —O—$Z^2$.

* * * * *